US011530298B2

United States Patent
DeRosa et al.

(10) Patent No.: US 11,530,298 B2
(45) Date of Patent: Dec. 20, 2022

(54) POLY(PHOSPHOESTERS) FOR DELIVERY OF NUCLEIC ACIDS

(71) Applicant: TRANSLATE BIO, INC., Lexington, MA (US)

(72) Inventors: Frank DeRosa, Lexington, MA (US); Michael Heartlein, Lexington, MA (US); Shrirang Karve, Lexington, MA (US); Yi Zhang, Lexington, MA (US)

(73) Assignee: Translate Bio, Inc., Lexington, MA (US)

( * ) Notice: Subject to any disclaimer, the term of this patent is extended or adjusted under 35 U.S.C. 154(b) by 400 days.

(21) Appl. No.: 16/621,045

(22) PCT Filed: Jun. 11, 2018

(86) PCT No.: PCT/US2018/036920
§ 371 (c)(1),
(2) Date: Dec. 10, 2019

(87) PCT Pub. No.: WO2018/231709
PCT Pub. Date: Dec. 20, 2018

(65) Prior Publication Data
US 2020/0277446 A1 Sep. 3, 2020

Related U.S. Application Data

(60) Provisional application No. 62/518,313, filed on Jun. 12, 2017.

(51) Int. Cl.
| | |
|---|---|
| C08G 79/04 | (2006.01) |
| A61K 38/53 | (2006.01) |
| A61K 47/34 | (2017.01) |
| C08F 293/00 | (2006.01) |
| A61K 31/7088 | (2006.01) |

(52) U.S. Cl.
CPC .............. *C08G 79/04* (2013.01); *A61K 38/53* (2013.01); *A61K 47/34* (2013.01); *C08F 293/00* (2013.01); *A61K 31/7088* (2013.01)

(58) Field of Classification Search
CPC .................................. C08G 79/04; A61K 47/34
See application file for complete search history.

(56) References Cited

FOREIGN PATENT DOCUMENTS

| WO | WO 1996/040672 A1 | 12/1996 |
|---|---|---|
| WO | WO 2001/068052 A2 | 9/2001 |
| WO | WO 2002/092667 A1 | 11/2002 |
| WO | WO 2019/207060 | 10/2019 |

OTHER PUBLICATIONS

"Effect of Side-chain structures on Gene Transfer Efficiency of Biodegradable Cationic Phosphoesters" authored by Wang et al. and published in the International Journal of Pharmaceutics (2003) 265, 75-84.*
"Thermoresponsive Polyphosphoesters Bearing Enzyme-cleavable Side Chains" authored by Iwasaki et al. and published in Chemistry Letters (2009) 38 (11) 1054-1055.*
"Biomedical Applications of Phosphorus-containing Polymers" authored by Wentrup-Byrne et al. and published in RSC Polymer Chemistry Series No. 11, p. 167-209.*
"Main-chain Phosphorus-containing Polymers for Therapeutic Applications" authored by Strasser et al., and published in Molecules (2020) 25, 1716.*
"High Definition Polyphosphoesters:between Nuclein Acids and Plastics" authored by Appukutti et al. and published in Polymer Chemistry (2018) 9, 2210.*
Alton et al., A randomised, double-blind, placebo-controlled trial of repeated nebulisation of non-viral cystic fibrosis transmembrane conductance regulator (CFTR) gene therapy in patients with cystic fibrosis, National Institute for Health Research, vol. 3, Issue 5 (2016).
International Search Report and Written Opinion of PCT/US18/36920, dated Dec. 20, 2018.

\* cited by examiner

*Primary Examiner* — Marc S Zimmer
(74) *Attorney, Agent, or Firm* — Proskauer Rose LLP; Fangli Chen

(57) ABSTRACT

Disclosed are polymers comprising the moiety A, which is a moiety of formula I: and pharmaceutically acceptable salts thereof, wherein R, $R^1$, $R^2$, L, n1 and n2 are as defined herein. These polymers are useful for delivering nucleic acids to subject. These polymers and pharmaceutically acceptable compositions comprising such polymers and nucleic acids can be useful for treating various diseases, disorders and conditions.

22 Claims, No Drawings
Specification includes a Sequence Listing.

SEQUENCE LISTING

<160> NUMBER OF SEQ ID NOS: 4

<210> SEQ ID NO 1
<211> LENGTH: 1239
<212> TYPE: RNA
<213> ORGANISM: Artificial Sequence
<220> FEATURE:
<223> OTHER INFORMATION: Chemically synthesized oligonucleotides

<400> SEQUENCE: 1
augagcagca agggcagcgu ggugcuggcc uacagcggcg gccuggacac cagcugcauc      60 cuggugugc ugaaggagca gggcuacgac gugaucgccu accuggccaa caucggccag     120
aaggaggacu ucgaggaggc ccgcaagaag gcccugaagc ugggcgccaa gaagguguuc     180
aucgaggacg ugagccgcga guucguggag gaguucaucu ggcccgccau ccagagcagc     240
gcccuguacg aggaccgcua ccugcugggc accagccugg cccgccccug caucgcccgc     300
aagcaggugg agaucgccca gcgcgagggc gccaaguacg ugagccacgg cgccaccggc     360
aagggcaacg accaggugcg cuucgagcug agcugcuaca gccuggcccc ccagaucaag     420
gugaucgccc ccuggcgcau gcccgaguuc uacaaccgcu ucaagggccg caacgaccug     480
auggaguacg ccaagcagca cggcauccc auccccguga ccccaagaa ccccuggagc     540 auggacgaga accugaugca caucagcuac gaggccggca uccuggagaa ccccaagaac     600

```
caggcccccc ccggccugua caccaagacc caggaccccg ccaaggcccc caacacccccc    660 gacauccugg agaucgaguu caagaagggc gugcccguga aggugaccaa cgugaaggac    720
ggcaccaccc accagaccag ccuggagcug uucauguacc ugaacgaggu ggccggcaag    780
cacggcgugg gccgcaucga caucguggag aaccgcuuca ucggcaugaa gagccgcggc    840
aucuacgaga ccccgccgg caccauccug uaccacgccc accuggacau cgaggccuuc    900
accauggacc gcgaggugcg caagaucaag cagggccugg gccugaaguu cgccgagcug    960
guguacaccg gcuucuggca cagccccgag ugcgaguucg ugcgccacug caucgccaag   1020
agccaggagc gcguggaggg caaggugcag gugagcgugc ugaagggcca ggugacauc    1080 cugggccgcg agagccccu gagccuguac aacgaggagc uggugagcau gaacgugcag   1140
ggcgacuacg agcccaccga cgccaccggc uucaucaaca ucaacagccu gcgccugaag   1200
gaguaccacc gccugcagag caaggugacc gccaaguga                         1239

<210> SEQ ID NO 2
<211> LENGTH: 140
<212> TYPE: RNA
<213> ORGANISM: Artificial Sequence
<220> FEATURE:
<223> OTHER INFORMATION: Chemically synthesized oligonucleotides

<400> SEQUENCE: 2
ggacagaucg ccuggagacg ccauccacgc uguuugacc uccauagaag acaccgggac      60
cgauccagcc uccgcggccg ggaacggugc auuggaacgc ggauucccg ugccaagagu    120 gacucaccgu ccuugacacg                                                140

<210> SEQ ID NO 3
<211> LENGTH: 105
<212> TYPE: RNA
<213> ORGANISM: Artificial Sequence
<220> FEATURE:
<223> OTHER INFORMATION: Chemically synthesized oligonucleotides

<400> SEQUENCE: 3
cggguggcau cccugugacc ccucccagu gccucuccug gcccuggaag uugccacucc     60
agugcccacc agccuugucc uaauaaaauu aaguugcauc aagcu                   105

<210> SEQ ID NO 4
<211> LENGTH: 105
<212> TYPE: RNA
<213> ORGANISM: Artificial Sequence
<220> FEATURE:
<223> OTHER INFORMATION: Chemically synthesized oligonucleotides

<400> SEQUENCE: 4
ggguggcauc ccugugaccc cucccagug ccucuccugg cccuggaagu ugccacucca     60
gugcccacca gccuuguccu aauaaaauua aguugcauca aagcu                  105
```

POLY(PHOSPHOESTERS) FOR DELIVERY OF NUCLEIC ACIDS

CROSS-REFERENCE TO RELATED APPLICATIONS

The present application is a 35 U.S.C. § 371 National Stage Application of International Application No. PCT/US18/36920, filed Jun. 11, 2018, which claims benefit of U.S. Provisional Application No. 62/518,313, filed Jun. 12, 2017, which is hereby incorporated by reference in its entirety.

SEQUENCE LISTING

The present specification makes reference to a Sequence Listing provided in electronic form as an ASCII.txt file named "MRT-1248WO_ST25.txt" that was generated on Jun. 11, 2018, and is 3,013 bytes in size.

BACKGROUND

Nucleic acids have been explored as a potential therapeutic option for certain disease states. In particular, ribonucleic acid (RNA) interference (RNAi) using, for example, small interfering RNA (siRNA), short hairpin RNA (shRNA), and antisense RNA (aRNA) approaches have been the subject of significant research and clinical development, for example, for binding to messenger RNA (mRNA), long non-coding RNA (lncRNA), micro-RNA (miRNA) and other endogenous targets. More recently, administration of mRNA, multimeric coding nucleic acid (MCNA), polymeric coding nucleic acid (PCNA), guide RNA (gRNA) and CRISPR RNA (crRNA) have been investigated as possible treatments of various diseases. However, the delivery of nucleic acids as therapeutics remains a challenge.

SUMMARY

The present invention provides, among other things, polymers useful in delivering nucleic acids as a therapeutic. The invention is based, in part, on the surprising discovery that the polymers described herein provide safe and efficient delivery of nucleic acids, such as mRNA. In particular, the polymers of the present invention may provide one or more advantages over other polymers. For example, as described in more detail herein, the polymers of the present invention may provide enhanced endosomal release of the nucleic acid being delivered by the polymer. Additionally, the biodegradable nature of the polymer may provide greater patient tolerability than other polymeric delivery vehicles. Thus, the polymers of the present invention may provide more potent and/or safer nucleic acid delivery for the treatment of a variety of diseases.

In some aspects, the present invention provides a polymer comprising a repeating unit that is:

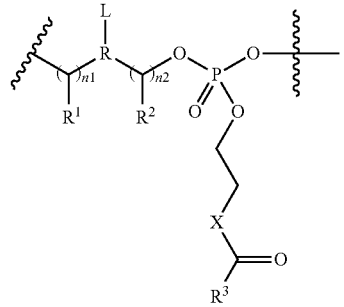

or a pharmaceutically acceptable salt thereof, wherein:
  each instance of $R^1$ independently is —H or a $C_1$-$C_{20}$ aliphatic group;
  each instance of $R^2$ independently is —H or a $C_1$-$C_{20}$ aliphatic group;
  each instance of $R^3$ independently is —H or a $C_1$-$C_{20}$ aliphatic group;
  X is independently S or O;
  n1 is an integer from 1 to 6;
  n2 is an integer from 1 to 6;
  R is N or CH; and
  L is $C_{1-6}$ alkyl or a protonatable group provided that when R is CH then L is a protonatable group, wherein the protonatable group comprises at least one 1° amino, 2° amino, 3° amino or imidazolyl group.

In some aspects, the present invention provides methods of preparing the polymers of the present invention.

In some aspects, the present invention provides a pharmaceutical composition (a "provided composition") comprising a polymer of the present invention and one or more nucleic acids or polynucleotides.

In some aspects, the present invention provides methods of treating a disease in a subject comprising administering to the subject a provided composition.

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference for all purposes.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amino acid: As used herein, the term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a modified amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "modified amino acid" encompasses a chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Biologically active: As used herein, the term "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" refers to delivery of a composition to an organism, including but not limited to an animal or human. For delivery to a multi-tissue organism, delivery encompasses both local and systemic delivery. For example, delivery of a nucleic acid such as mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end formation); (3) translation of an mRNA into a polypeptide or protein; and/or (4) post-translational modification of a polypeptide or protein. In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" or "mRNA" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems or plasmid-based expression systems or in vitro transcription (IVT) systems, and optionally purified and/or modified, or produced by chemical synthesis. In some embodiments, for example, for mRNA produced using recombinant or plasmid-based expression systems or produced by chemical synthesis, the mRNA coding region, the mRNA non-coding region, or both the mRNA coding and non-coding regions, can include a unique nucleic acid sequence (having modified or unmodified nucleic acids), i.e., that is different from natural and/or known nucleic acid sequences for that mRNA. For example, in some embodiments, the mRNA coding region can include one or more codons that have a different triplet nucleic acid sequence than the triplet nucleic acid sequence of the corresponding codons in the corresponding natural or known mRNA (referred to herein as a "codon-optimized" sequence). An mRNA sequence is presented in the 5' to 3' direction unless otherwise indicated. In some embodiments, "mRNA" can encompass both unmodified RNA and modified mRNA (mmRNA). The modifications in mmRNA can comprise nucleoside analogs such as analogs having one or more chemically modified bases or sugars, backbone modifications, or other modifications described herein. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses ribonucleic acids (RNA), including but not limited to any one or more of interference RNAs (RNAi), small interfering RNA (siRNA), short hairpin RNA (shRNA), antisense RNA (aRNA), messenger RNA (mRNA), modified messenger RNA (mmRNA), long non-coding RNA (lncRNA), micro-RNA (miRNA) multimeric coding nucleic acid (MCNA), polymeric coding nucleic acid (PCNA), guide RNA (gRNA) and CRISPR RNA (crRNA). In some embodiments, "nucleic acid" encompasses deoxyribonucleic acid (DNA), including but not limited to any one or more of single-stranded DNA (ssDNA), double-stranded DNA (dsDNA) and complementary DNA (cDNA). In some embodiments, "nucleic acid" encompasses both RNA and DNA. In embodiments, DNA may be in the form of antisense DNA, plasmid DNA, parts of a plasmid DNA, pre-condensed DNA, a product of a polymerase chain reaction (PCR), vectors (e.g., P1, PAC, BAC, YAC, artificial chromosomes), expression cassettes, chimeric sequences, chromosomal DNA, or derivatives of these groups. In embodiments, RNA may be in the form of messenger RNA (mRNA), ribosomal RNA (rRNA), signal recognition particle RNA (7 SL RNA or SRP RNA), transfer RNA (tRNA), transfer-messenger RNA (tmRNA), small nuclear RNA (snRNA), small nucleolar RNA (snoRNA), SmY RNA, small Cajal body-specific RNA (scaRNA), guide RNA (gRNA), ribonuclease P (RNase P), Y RNA, telomerase RNA component (TERC), spliced leader RNA (SL RNA), antisense RNA (aRNA or asRNA), cis-natural antisense transcript (cis-NAT), CRISPR RNA (crRNA), long noncoding RNA (lncRNA), micro-RNA (miRNA), piwi-interacting RNA (piRNA), small interfering RNA (siRNA), transacting siRNA (tasiRNA), repeat associated siRNA (rasiRNA), 73K RNA, retrotransposons, a viral genome, a viroid, satellite RNA, or derivatives of these groups. In some embodiments, a nucleic acid is a mRNA encoding a protein such as an enzyme.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable", as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect disparate compartments or tissues of the entire body or of an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Aliphatic: As used herein, the term aliphatic refers to both $C_1$-$C_{40}$ hydrocarbons and includes both saturated and unsaturated hydrocarbons. An aliphatic may be linear, branched, or cyclic. For example, $C_1$-$C_{20}$ aliphatics can include $C_1$-$C_{20}$ saturated alkyls (e.g., linear or branched $C_1$-$C_{20}$ saturated alkyls), $C_2$-$C_{20}$ alkenyls (e.g., linear or branched $C_4$-$C_{20}$ dienyls, linear or branched $C_6$-$C_{20}$ trienyls, and the like), and $C_2$-$C_{20}$ alkynyls (e.g., linear or branched $C_2$-$C_{20}$ alkynyls). aliphatics can include $C_3$-$C_{20}$ cyclic aliphatics (e.g., $C_3$-$C_{20}$ cycloalkyls, $C_4$-$C_{20}$ cycloalkenyls, or $C_8$-$C_{20}$ cycloalkynyls). The term "alkylene," as used herein, represents a saturated divalent straight or branched chain hydrocarbon group and is exemplified by methylene, ethylene, isopropylene and the like. In certain embodiments, the aliphatic may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. For example, an aliphatic may be substituted with one or more (e.g., 1, 2, 3, 4, 5, or 6 independently selected substituents) of halogen, —$CO_2R'$, —CN, —OH, —OR', —$NH_2$, —NHR', —N(R')$_2$, —SR' or —$SO_2R'$, wherein each instance of R' independently is $C_{1-3}$ alkyl. In certain embodiments, the aliphatic is unsubstituted. In certain embodiments, the aliphatic does not include any heteroatoms.

DETAILED DESCRIPTION OF CERTAIN EMBODIMENTS

Polymers—Moiety A

In some aspects, the present invention provides a polymer comprising a repeating unit that is:

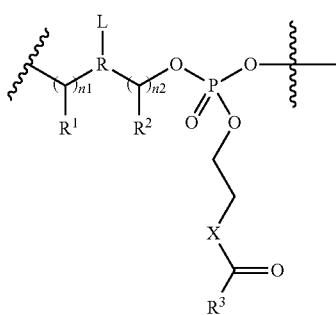

or a pharmaceutically acceptable salt thereof, wherein:
each instance of $R^1$ independently is —H or a $C_1$-$C_{20}$ aliphatic group;
each instance of $R^2$ independently is —H or a $C_1$-$C_{20}$ aliphatic group;
each instance of $R^3$ independently is —H or a $C_1$-$C_{20}$ aliphatic group;
X is independently S or O;
n1 is an integer from 1 to 6;
n2 is an integer from 1 to 6;
R is N or CH; and
L is $C_{1-6}$ alkyl or a protonatable group provided that when R is CH then L is a protonatable group, wherein the protonatable group comprises at least one 1° amino, 2° amino, 3° amino or imidazolyl group.

In some embodiments, $R^1$ independently is —H, —CH$_3$, or —CH$_2$CH$_3$.

In some embodiments, $R^2$ independently is —H, —CH$_3$, or —CH$_2$CH$_3$.

In some embodiments, $R^3$ independently is —H, —CH$_3$, —CH$_2$CH$_3$, —CH$_2$CH$_2$CH$_3$, CH(CH$_3$)$_2$, or C(CH$_3$)$_3$.

In some embodiments, each instance of $R^1$ and $R^2$ independently is —H or —CH$_3$. In some embodiments, each instance of $R^1$ and $R^2$ is —H, —CH$_3$ or —CH$_2$CH$_3$. In some embodiments, each instance of $R^1$ and $R^2$ is —CH$_3$. In some embodiments, each instance of $R^1$ and $R^2$ is —H.

In some embodiments, X is independently O.
In some embodiments, X is independently S.
In some embodiments, n1 is 1, 2 or 3; or n1 is 2, 3 or 4; or n1 is 3, 4 or 5; or n1 is 4, 5 or 6; or n1 is 1 or 2; or n1 is 2 or 3; or n1 is 3 or 4; or n1 is 4 or 5; or n1 is 5 or 6; or n1 is 1; or n1 is 2; or n1 is 3; or n1 is 4; or n1 is 5; or n1 is 6.

In some embodiments, n2 is 1, 2 or 3; or n2 is 2, 3 or 4; or n2 is 3, 4 or 5; or n2 is 4, 5 or 6; or n2 is 1 or 2; or n2 is 2 or 3; or n2 is 3 or 4; or n2 is 4 or 5; or n2 is 5 or 6; or n2 is 1; or n2 is 2; or n2 is 3; or n2 is 4; or n2 is 5; or n2 is 6.

In some embodiments,
n1 is 1, 2 or 3; or n1 is 2, 3 or 4; or n1 is 3, 4 or 5; or n1 is 4, 5 or 6; or n1 is 1 or 2; or n1 is 2 or 3; or n1 is 3 or 4; or n1 is 4 or 5; or n1 is 5 or 6; or n1 is 1; or n1 is 2; or n1 is 3; or n1 is 4; or n1 is 5; or n1 is 6;
n2 is 1, 2 or 3; or n2 is 2, 3 or 4; or n2 is 3, 4 or 5; or n2 is 4, 5 or 6; or n2 is 1 or 2; or n2 is 2 or 3; or n2 is 3 or 4; or n2 is 4 or 5; or n2 is 5 or 6; or n2 is 1; or n2 is 2; or n2 is 3; or n2 is 4; or n2 is 5; or n2 is 6; and
each instance of $R^1$ and $R^2$ independently is —H or —CH$_3$; or each instance of $R^1$ and $R^2$ is —H, —CH$_3$ or —CH$_2$CH$_3$; or each instance of $R^1$ and $R^2$ is —CH$_3$; or each instance of $R^1$ and $R^2$ is —H.

In some embodiments, R is CH.

In some embodiments, R is N.
In some embodiments, R is N and L is $C_{1-6}$ alkyl.
In some embodiments, L is a protonatable group. A suitable protonatable group does not significantly interfere with the delivery of nucleic acid using the polymer of the present invention. Generally, a suitable protonatable group is a $C_{1-10}$ hydrocarbon additionally containing at least one 1° amino, 2° amino, 3° amino or imidazolyl group. In some embodiments, non-protonatable linkages such as esters and ethers may also be present. In some embodiments, side-chains of the naturally occurring amino acids may also be present.

In some embodiments, L is a protonatable group such that at least one conjugate acid of L-H has a pKa in water of about 4.5 to about 11.5. In some embodiments, L is a protonatable group such that at least one conjugate acid of L-H has a pKa in water of about 5 to about 11. In some embodiments, L is a protonatable group such that at least one conjugate acid of L-H has a pKa in water of about 6 to about 10. In some embodiments, L is a protonatable group such that at least one conjugate acid of L-H has a pKa in water of about 7 to about 9. In some embodiments, L is a protonatable group such that at least one conjugate acid of L-H has a pKa in water of about 8. In some embodiments, L is a protonatable group such that at least one conjugate acid of L-H has a pKa in water of 10.

In some embodiments, L is a protonatable group such that at least one conjugate acid of L-H has a pKa in water of about 5 to about 7. In some embodiments, L is a protonatable group such that at least one conjugate acid of L-H has a pKa in water of about 6 or 7. In some embodiments, L is a protonatable group such that at least one conjugate acid of L-H has a pKa in water of about 8 to about 11. In some embodiments, L is a protonatable group such that at least one conjugate acid of L-H has a pKa in water of about 9 or 10. In some embodiments, L is a protonatable group such that at least one conjugate acid of L-H has a pKa in water of about 8.

In some embodiments, R is CH and L is a protonatable group. In some embodiments, R is N and L is a protonatable group.

In some embodiments, a repeating unit is

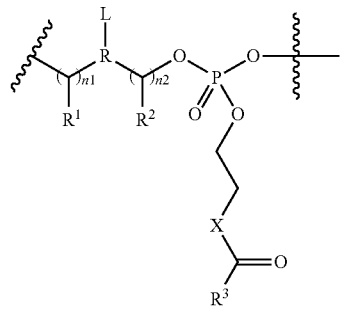

or a pharmaceutically acceptable salt thereof, wherein:
L is $C_{1-6}$ alkyl; and
each of R, $R^1$, $R^2$, $R^3$, X, n1 and n2 is as defined above, both singly and in combination.

In some embodiments, L is —CH$_3$, Et, Pr, $^i$Pr, Bu, sec-Bu, $^i$Bu, tert-Bu, pentyl, tert-pentyl, isopentyl, sec-pentyl, 3-pentyl or hexyl. In some embodiments, L is —CH$_3$, Et, Pr, $^i$Pr or Bu. In some embodiments, L is —CH$_3$, Et or Pr. In some embodiments, L is —CH$_3$. In some embodiments, L is Et. In some embodiments, L is Pr. In some embodiments, L is $^i$Pr. In some embodiments, L is Bu.

In some embodiments, a repeating unit is:

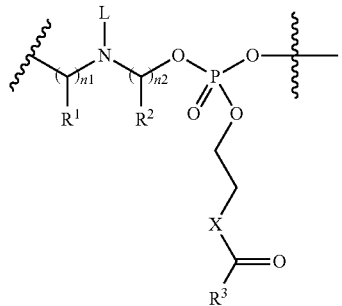

wherein each of $R^1$, $R^2$, $R^3$, X, L, n1 and n2 is as defined and described in embodiments above, both singly and in combination.

In some embodiments, the repeating unit is:

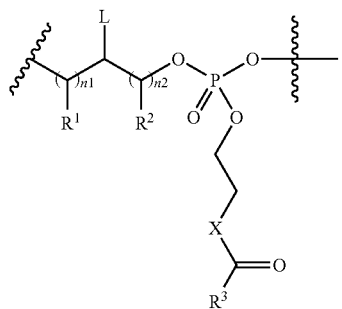

wherein each of $R^1$, $R^2$, $R^3$, X, L, n1 and n2 is as defined and described in embodiments above, both singly and in combination.

In some embodiments, a repeating unit is:

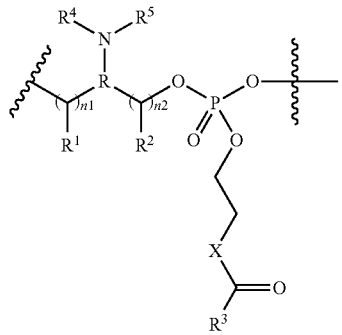

or a pharmaceutically acceptable salt thereof, wherein:
each of $R^4$ and $R^5$ independently is —H or a $C_1$-$C_{20}$ aliphatic group (e.g., a C1-6 alkyl); and
each of R, $R^1$, $R^2$, $R^3$, X, n1 and n2 is as defined above, both singly and in combination.

In some embodiments, $R^4$ independently is —H, —CH$_3$, Et, Pr, $^i$Pr, Bu, sec-Bu, $^i$Bu, tert-Bu, pentyl, tert-pentyl, isopentyl, sec-pentyl, 3-pentyl or hexyl; or $R^4$ is —H, —CH$_3$, Et, Pr, $^i$Pr or Bu; or $R^4$ is —CH$_3$, Et, Pr, $^i$Pr or Bu; or $R^4$ is —H, —CH$_3$, Et or Pr; or $R^4$ is —CH$_3$, Et or Pr; or $R^4$ is —CH$_3$; or $R^4$ is Et; or $R^4$ is Pr.

In some embodiments, $R^5$ independently is —H, —CH$_3$, Et, Pr, $^i$Pr, Bu, sec-Bu, $^i$Bu, tert-Bu, pentyl, tert-pentyl, isopentyl, sec-pentyl, 3-pentyl or hexyl; or $R^5$ is —CH$_3$, Et, Pr, $^i$Pr, Bu, sec-Bu, $^i$Bu, tert-Bu, pentyl, tert-pentyl, isopentyl, sec-pentyl, 3-pentyl or hexyl; or $R^5$ is —CH$_3$, Et, Pr, $^i$Pr or Bu; or $R^4$ is —CH$_3$, Et or Pr; or $R^5$ is —CH$_3$; or $R^5$ is Et; or $R^5$ is Pr.

In some embodiments, $R^4$ is —H, —CH$_3$, Et, Pr, $^i$Pr, Bu, sec-Bu, $^i$Bu, tert-Bu, pentyl, tert-pentyl, isopentyl, sec-pentyl, 3-pentyl or hexyl. In some embodiments, $R^4$ is —H, —CH$_3$, Et, Pr, $^i$Pr or Bu. In some embodiments, $R^4$ is —CH$_3$, Et, Pr, iPr or Bu. In some embodiments, $R^4$ is —H, —CH$_3$, Et or Pr. In some embodiments, $R^4$ is —CH$_3$, Et or Pr. In some embodiments, $R^4$ is —CH$_3$. In some embodiments, $R^4$ is Et. In some embodiments, $R^4$ is Pr.

In some embodiments, $R^5$ is —H, —CH$_3$, Et, Pr, $^i$Pr, Bu, sec-Bu, $^i$Bu, tert-Bu, pentyl, tert-pentyl, isopentyl, sec-pentyl, 3-pentyl or hexyl. In some embodiments, $R^5$ is —CH$_3$, Et, Pr, $^i$Pr or Bu. In some embodiments, $R^5$ is —CH$_3$, Et or Pr. In some embodiments, $R^5$ is —CH$_3$. In some embodiments, $R^5$ is Et. In some embodiments, $R^5$ is Pr.

In some embodiments, a repeating unit is:

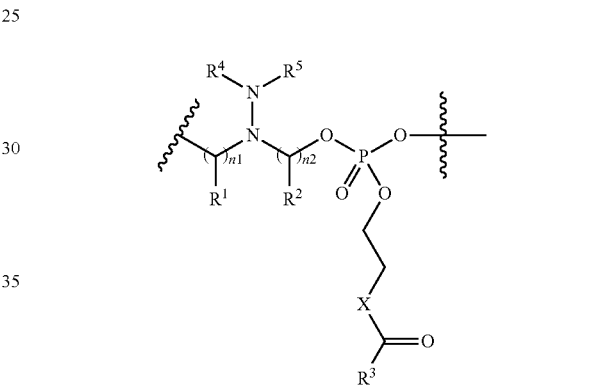

wherein each of $R^1$, $R^2$, $R^3$, $R^4$, $R^5$, X, n1 and n2 is as defined and described in embodiments above.

In some embodiments, a repeating unit is:

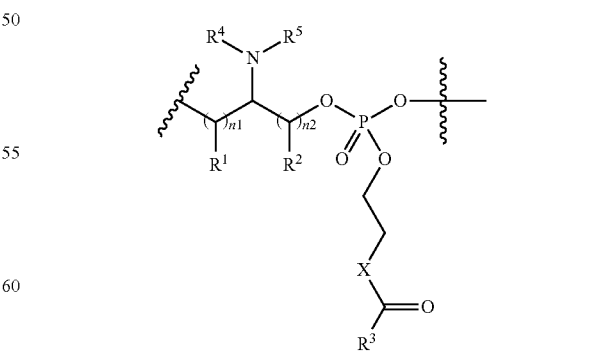

wherein each of $R^1$, $R^2$, $R^3$, $R^4$, $R^5$, X, n1 and n2 is as defined and described in embodiments above, both singly and in combination.

In some embodiments, a repeating unit is:

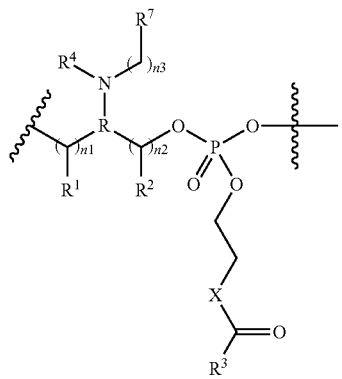

or a pharmaceutically acceptable salt thereof, wherein:

n3 is 1, 2, 3 or 4;

$R^7$ is halo, $C_{1-4}$ alkyl, $C_{1-4}$ haloalkyl, —OH, —OR$^{J1}$, —NH$_2$, —NHR$^{J1}$, —N(R$^{J1}$)$_2$, —C(O)R$^{J1}$, —CN or —NO$_2$, wherein each instance of R$^{J1}$ is independently $C_{1-3}$ alkyl;

$R^6$ is —H or a $C_1$-$C_{20}$ aliphatic group (e.g., a $C_{1-6}$ alkyl); and each of R, $R^1$, $R^2$, $R^3$, X, n1, and n2 is as defined above, both singly and in combination.

In some embodiments, $R^6$ is —H, —CH$_3$, Et, Pr, $^i$Pr, Bu, sec-butyl, $^i$Bu, tert-Bu, pentyl, tert-pentyl, isopentyl, sec-pentyl, 3-pentyl, or hexyl; or $R^6$ is —CH$_3$, Et, Pr, $^i$Pr, Bu, sec-butyl, $^i$Bu, tert-Bu, pentyl, tert-pentyl, isopentyl, sec-pentyl, 3-pentyl, or hexyl; or $R^6$ is —CH$_3$, Et, Pr, $^i$Pr, or Bu; or $R^6$ is —CH$_3$, Et, or Pr; or $R^6$ is —CH$_3$.

In some embodiments, $R^7$ is —H, —CH$_3$, Et, Pr, Bu, —NH$_2$, —NHMe, —NMe$_2$, —NHEt or —NEt$_2$; or $R^7$ is —H, —CH$_3$, Et, Pr, —NH$_2$, —NHMe or —NMe$_2$; or $R^7$ is —CH$_3$, Et or Pr; or $R^7$ is Pr.

In some embodiments, n3 is 1, 2 or 3; or n3 is 2, 3 or 4; or n3 is 2 or 3; or n3 is 2; or n3 is 3.

In some embodiments, $R^6$ is —H, —CH$_3$, Et, Pr, $^i$Pr, Bu, sec-butyl, $^i$Bu, tert-Bu, pentyl, tert-pentyl, isopentyl, sec-pentyl, 3-pentyl, or hexyl. In some embodiments, $R^6$ is —CH$_3$, Et, Pr, $^i$Pr, Bu, sec-butyl, $^i$Bu, tert-Bu, pentyl, tert-pentyl, isopentyl, sec-pentyl, 3-pentyl, or hexyl. In some embodiments, $R^6$ is —CH$_3$, Et, Pr, $^i$Pr, or Bu. In some embodiments, $R^6$ is —CH$_3$, Et, or Pr. In some embodiments, $R^6$ is —CH$_3$.

In some embodiments, $R^7$ is —H, —CH$_3$, Et, Pr, Bu, —NH$_2$, —NHMe, —NMe$_2$, —NHEt or —NEt$_2$. In some embodiments, $R^7$ is —H, —CH$_3$, Et, Pr, —NH$_2$, —NHMe or —NMe$_2$. In some embodiments, $R^7$ is —CH$_3$, Et or Pr. In some embodiments, $R^7$ is Pr.

In some embodiments, n3 is 1, 2 or 3. In some embodiments, n3 is 2, 3 or 4. In some embodiments, n3 is 2 or 3. In some embodiments, n3 is 2. In some embodiments, n3 is 3.

In some embodiments, a repeating unit is

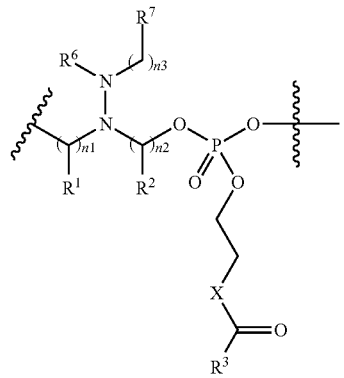

wherein each of $R^1$, $R^2$, $R^3$, $R^6$, $R^7$, X, n1, n2 and n3 is as defined and described in embodiments above, both singly and in combination.

In some embodiments, a repeating unit is

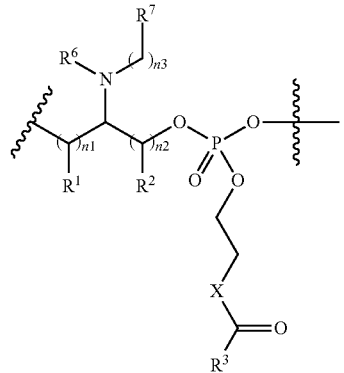

wherein each of $R^1$, $R^2$, $R^3$, $R^6$, $R^7$, X, n1, n2, and n3 is as defined and described in embodiments above, both singly and in combination.

In some embodiments, a repeating unit is:

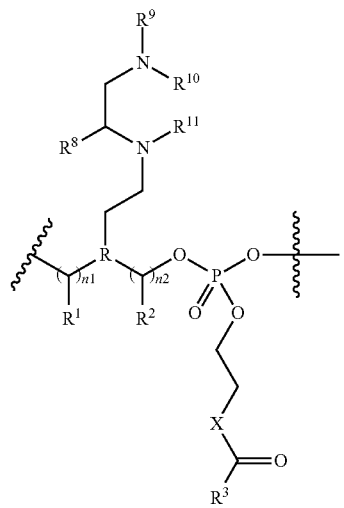

or a pharmaceutically acceptable salt thereof, wherein:

each of $R^8$, $R^9$, $R^{10}$ and $R^{11}$ independently is a $C_1$-$C_{20}$ aliphatic (e.g., a $C_{1-6}$ aliphatic, $C_{1-4}$ haloalkyl or $C_{3-6}$ cycloalkyl, each of which is optionally substituted with 1-4 occurrences of R*);

each instance of R* independently is halogen, —$CO_2R^{J1}$, —CN, —OH, —$OR^{J1}$, —$NH_2$, —$NHR^{J1}$, —$N(R^{J1})_2$, —$SR^{J1}$ or —$SO_2R^{J1}$, wherein each instance of $R^{J1}$ independently is $C_{1-3}$ alkyl; and each of $R^1$, $R^2$, $R^3$, X, n1 and n2 is as defined above for formula (I), both singly and in combination.

In some embodiments, $R^8$ is —H, —$CH_3$, Et, Pr, Bu, —$(CH_2)_3NH_2$, —$(CH_2)_4NH_2$ or —$(CH_2)_5NH_2$; or $R^8$ is —H, —$CH_3$, Et, —$(CH_2)_4NH_2$, or —$(CH_2)_5NH_2$; or $R^8$ is —H or —$(CH_2)_4NH_2$; or $R^8$ is —$(CH_2)_4NH_2$.

In some embodiments, $R^9$ is —H, —$CH_3$, Et, Pr, Bu, —$NH_2$, —NHMe, —$NMe_2$, —NHEt or —$NEt_2$; or $R^9$ is —H, —$CH_3$, Et, Pr, —$NH_2$, —NHMe or —$NMe_2$; or $R^9$ is —$CH_3$, Et or Pr; or $R^9$ is Pr.

In some embodiments, $R^{10}$ is —$CH_3$, Et, Pr, $^i$Pr, Bu, sec-butyl, $^i$Bu, tert-Bu, pentyl, tert-pentyl, isopentyl, sec-pentyl, 3-pentyl or hexyl; or $R^{10}$ is —$CH_3$, Et, Pr, $^i$Pr or Bu; or $R^{10}$ is —$CH_3$, Et or Pr; or $R^{10}$ is —$CH_3$.

In some embodiments, $R^{11}$ is —H, —$CH_3$, Et, Pr, $^i$Pr, Bu, hexyl, cyclopropyl, cyclobutyl, cyclopentyl or cyclohexyl; or $R^{11}$ is H, —$CH_3$, Et, Pr or cyclopropyl; or $R^{11}$ is H, —$CH_3$ or Et; or $R^{11}$ is —H.

In some embodiments, $R^8$ is —H, —$CH_3$, Et, Pr, Bu, —$(CH_2)_3NH_2$, —$(CH_2)_4NH_2$ or —$(CH_2)_5NH_2$. In some embodiments, $R^8$ is —H, —$CH_3$, Et, —$(CH_2)_4NH_2$, or —$(CH_2)_5NH_2$. In some embodiments, $R^8$ is —H or —$(CH_2)_4NH_2$. In some embodiments, $R^8$ is —$(CH_2)_4NH_2$.

In some embodiments, $R^9$ is —H, —$CH_3$, Et, Pr, Bu, —$NH_2$, —NHMe, —$NMe_2$, —NHEt or —$NEt_2$. In some embodiments, $R^9$ is —H, —$CH_3$, Et, Pr, —$NH_2$, —NHMe or —$NMe_2$. In some embodiments, $R^9$ is —$CH_3$, Et or Pr. In some embodiments, $R^9$ is Pr.

In some embodiments, $R^{10}$ is —$CH_3$, Et, Pr, $^i$Pr, Bu, sec-butyl, $^i$Bu, tert-Bu, pentyl, tert-pentyl, isopentyl, sec-pentyl, 3-pentyl or hexyl. In some embodiments, $R^{10}$ is —$CH_3$, Et, Pr, $^i$Pr or Bu. In some embodiments, $R^{10}$ is —$CH_3$, Et or Pr. In some embodiments, $R^{10}$ is —$CH_3$.

In some embodiments, $R^{11}$ is —H, —$CH_3$, Et, Pr, $^i$Pr, Bu, hexyl, cyclopropyl, cyclobutyl, cyclopentyl or cyclohexyl. In some embodiments, $R^{11}$ is H, —$CH_3$, Et, Pr or cyclopropyl. In some embodiments, $R^{11}$ is H, —$CH_3$ or Et. In some embodiments, $R^{11}$ is —H.

In some embodiments, a repeating unit is:

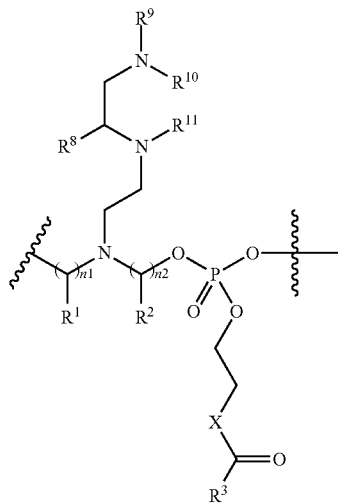

wherein each of $R^1$, $R^2$, $R^3$, $R^8$, $R^9$, $R^{10}$, $R^{11}$, X, n1 and n2 is as defined and described in embodiments above, both singly and in combination.

In some embodiments, a repeating unit is:

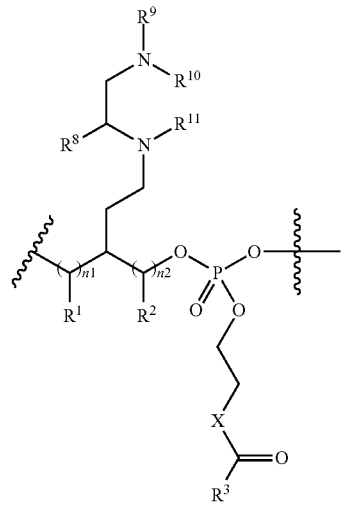

wherein each of $R^1$, $R^2$, $R^3$, $R^8$, $R^9$, $R^{10}$, $R^{11}$, X, n1 and n2 is as defined and described in embodiments above, both singly and in combination.

In some embodiments, a repeating unit is:

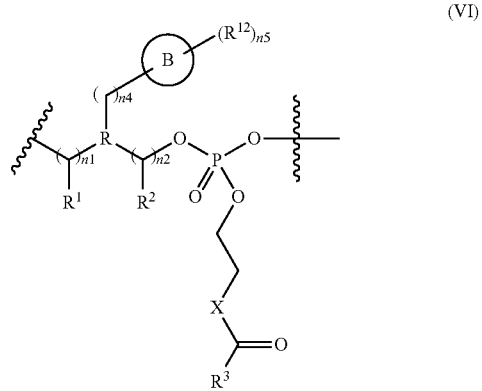

(VI)

or a pharmaceutically acceptable salt thereof, wherein:
B is a 5-membered heterocycle having 1 or 2 ring nitrogen atoms;
n4 is 1, 2, 3 or 4;
each instance of $R^{12}$ independently is selected from halo, $C_{1-4}$ alkyl, $C_{1-4}$ haloalkyl, —OH, —$OR^{J1}$, —$NH_2$, —$NHR^{J1}$, —$N(R^{J1})_2$, —$C(O)R^{J1}$, —CN and —$NO_2$;
wherein each instance of $R^{J1}$ is independently $C_{1-3}$ alkyl;
n5 is 0, 1, 2 or 3; and
each of R, $R^1$, $R^2$, $R^3$, X, n1 and n2 is as defined above, both singly and in combination.

In some embodiments, B is an aromatic heterocyclic ring.
In some embodiments, B is a non-aromatic heterocyclic ring.
In some embodiments, B is pyrazolyl, imidazolyl, pyrrolyl, triazolyl, or tertazolyl; or B is pyrazolyl or imidazolyl; or B is imidazolyl.

In some embodiments, $R^{12}$ is —$CH_3$, Et, Pr, Bu, $^i$Pr, —F, —Cl, —$CF_3$, —OMe, —OEt, —OPr, —$NH_2$, —$SO_2NH_2$, —CN or —NO$_2$; or R$^{12}$ is —CH$_3$, —F, —Cl, —CF$_3$, —OMe or —OEt; or R$^{12}$ is —F, —CH$_3$ or —Cl; or R$^{12}$ is —CH$_3$.

In some embodiments, n4 is 0, 1 or 2; or n4 is 0 or 1; or n4 is 0.

In some embodiments, n5 is 0, 1 or 2; or n5 is 0 or 1; or n5 is 0.

In some embodiments, B is pyrazolyl, imidazolyl, pyrrolyl, triazolyl, or tertazolyl. In some embodiments, B is pyrazolyl or imidazolyl. In some embodiments, B is imidazolyl.

In some embodiments, R$^{12}$ is —CH$_3$, Et, Pr, Bu, $^i$Pr, —F, —Cl, —CF$_3$, —OMe, —OEt, —OPr, —NH$_2$, —SO$_2$NH$_2$, —CN or —NO$_2$. In some embodiments, R$^{12}$ is —CH$_3$, —F, —Cl, —CF$_3$, —OMe or —OEt. In some embodiments, R$^{12}$ is —F, —CH$_3$ or —Cl. In some embodiments, R$^{12}$ is —CH$_3$.

In some embodiments, n4 is 0, 1 or 2. In some embodiments, n4 is 0 or 1. In some embodiments, n4 is 0.

In some embodiments, n5 is 0, 1 or 2. In some embodiments, n5 is 0 or 1. In some embodiments, n5 is 0.

In some embodiments, n5 is 0, 1, or 2; and R$^{12}$ is —F or —CH$_3$. In some embodiments, n5 is 1 and R$^{12}$ is —CH$_3$.

In some embodiments, a repeating unit is:

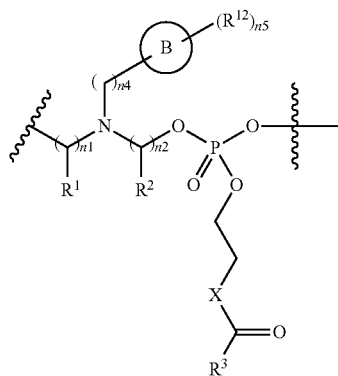

wherein each of R$^1$, R$^2$, R$^3$, R$^{12}$, B, X, n1, n2, n4 and n5 is as defined and described in embodiments above, both singly and in combination.

In some embodiments, a repeating unit is:

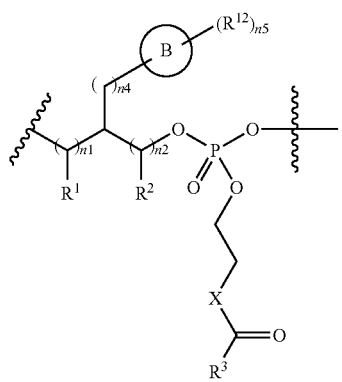

wherein each of R$^1$, R$^2$, R$^3$, R$^{12}$, X, B, n1, n2, n4 and n5 is as defined and described in embodiments above, both singly and in combination.

In some embodiments, a repeating unit is:

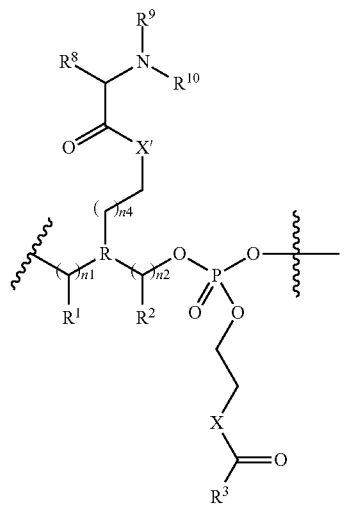

or a pharmaceutically acceptable salt thereof, wherein:
X' is —O— or —NR$^{13}$—, wherein
R$^{13}$ is —H or a C$_1$-C$_{20}$ aliphatic (e.g., a C$_{1-6}$ aliphatic or C$_{3-6}$ cycloalkyl);
n4 is 0, 1, 2 or 3;
each of R$^8$, R$^9$ and R$^{10}$ is —H or is a C$_1$-C$_{20}$ aliphatic (e.g., a C$_{1-6}$ aliphatic, C$_{1-4}$ haloalkyl or C$_{3-6}$ cycloalkyl, each of which is optionally substituted with 1-4 occurrences of R*);
each instance of R* independently is halogen, —CO$_2$R$^{J1}$, —CN, —OH, —OR$^{J1}$, —NH$_2$, —NHR$^{J1}$, —N(R$^{J1}$)$_2$, —S$^{J1}$ or —SO$_2$R$^{J1}$,
wherein each instance of R$^{J1}$ independently is C$_{1-3}$ alkyl; and
each of R, R$^1$, R$^2$, R$^3$, X, n1 and n2 is as defined above, both singly and in combination.

In some embodiments, X' is —NH— or —O—; or X' is —NR$^{13}$—; or X' is —NH—; or X' is —O—.

In some embodiments, n4 is 1, 2 or 3; or n4 is 1 or 2; or n4 is 2 or 3; or n4 is 1.

In some embodiments, R$^8$ is —H, —CH$_3$, Et, Pr, Bu, —NH$_2$, —NHMe, —NMe$_2$, —NHEt or —NEt$_2$; or R$^8$ is —H, —CH$_3$, Et, Pr, —NH$_2$, —NHMe or —NMe$_2$; or R$^8$ is —CH$_3$, Et or Pr; or R$^8$ is Pr.

In some embodiments, R$^9$ is —H, —CH$_3$, Et, Pr, $^i$Pr, Bu, sec-butyl, $^i$Bu, tert-Bu, pentyl, tert-pentyl, isopentyl, sec-pentyl, 3-pentyl or hexyl; or R$^9$ is —CH$_3$, Et, Pr, $^i$Pr, Bu, sec-butyl, $^i$Bu, tert-Bu, pentyl, tert-pentyl, isopentyl, sec-pentyl, 3-pentyl or hexyl; or R$^9$ is —CH$_3$, Et, Pr, $^i$Pr or Bu; or R$^9$ is —CH$_3$, Et or Pr; or R$^9$ is —CH$_3$.

In some embodiments, R$^{10}$ is —H, —CH$_3$, Et, Pr, Bu, —(CH$_2$)$_3$NH$_2$, —(CH$_2$)$_4$NH$_2$ or —(CH$_2$)$_5$NH$_2$; or R$^{19}$ is —H, —CH$_3$, Et, —(CH$_2$)$_4$NH$_2$ or —(CH$_2$)$_5$NH$_2$; or R$^{10}$ is —H or —(CH$_2$)$_4$NH$_2$; or R$^{10}$ is —(CH$_2$)$_4$NH$_2$.

In some embodiments, R$^{13}$ is —H, —CH$_3$, Et, Pr, $^i$Pr, Bu, hexyl, cyclopropyl, cyclobutyl, cyclopentyl or cyclohexyl; or R$^{13}$ is —H, —CH$_3$, Et, cyclopropyl or cyclobutyl; or R$^{13}$ is —H, —CH$_3$ or cyclopropyl; or R$^{13}$ is —H.

In some embodiments, X' is —NH— or —O—. In some embodiments, X' is —NR$^{13}$. In some embodiments, X' is —NH—. In some embodiments, X' is —O—.

In some embodiments, n4 is 1, 2 or 3. In some embodiments, n4 is 1 or 2. In some embodiments, n4 is 2 or 3. In some embodiments, n4 is 1.

In some embodiments, $R^8$ is —H, —CH$_3$, Et, Pr, Bu, —NH$_2$, —NHMe, —NMe$_2$, —NHEt or —NEt$_2$. In some embodiments, $R^8$ is —H, —CH$_3$, Et, Pr, —NH$_2$, —NHMe or —NMe$_2$. In some embodiments, $R^8$ is —CH$_3$, Et or Pr. In some embodiments, $R^8$ is Pr.

In some embodiments, $R^9$ is —H, —CH$_3$, Et, Pr, $^i$Pr, Bu, sec-butyl, $^i$Bu, tert-Bu, pentyl, tert-pentyl, isopentyl, sec-pentyl, 3-pentyl or hexyl. In some embodiments, $R^9$ is —CH$_3$, Et, Pr, $^i$Pr, Bu, sec-butyl, $^i$Bu, tert-Bu, pentyl, tert-pentyl, isopentyl, sec-pentyl, 3-pentyl or hexyl. In some embodiments, $R^9$ is —CH$_3$, Et, Pr, $^i$Pr or Bu. In some embodiments, $R^9$ is —CH$_3$, Et or Pr. In some embodiments, $R^9$ is —CH$_3$.

In some embodiments, $R^{10}$ is —H, —CH$_3$, Et, Pr, Bu, —(CH$_2$)$_3$NH$_2$, —(CH$_2$)$_4$NH$_2$ or —(CH$_2$)$_5$NH$_2$. In some embodiments, $R^{10}$ is —H, —CH$_3$, Et, —(CH$_2$)$_4$NH$_2$ or —(CH$_2$)$_5$NH$_2$. In some embodiments, $R^{10}$ is —H or —(CH$_2$)$_4$NH$_2$. In some embodiments, $R^{10}$ is —(CH$_2$)$_4$NH$_2$.

In some embodiments, $R^{13}$ is —H, —CH$_3$, Et, Pr, $^i$Pr, Bu, hexyl, cyclopropyl, cyclobutyl, cyclopentyl or cyclohexyl. In some embodiments, $R^{13}$ is —H, —CH$_3$, Et, cyclopropyl or cyclobutyl. In some embodiments, $R^{13}$ is —H, —CH$_3$ or cyclopropyl. In some embodiments, $R^{13}$ is —H.

In some embodiments, a repeating unit is:

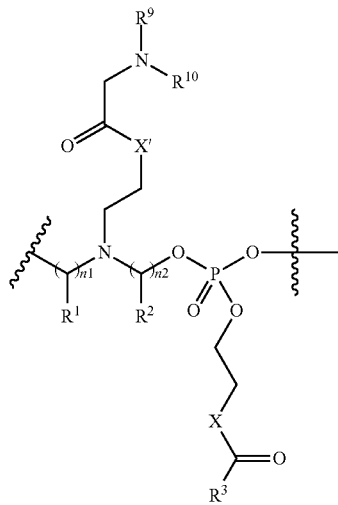

wherein each of $R^1$, $R^2$, $R^3$, $R^9$, $R^{10}$, n1, n2, X, and X' is as defined and described in embodiments above and below, both singly and in combination.

In some embodiments, $R^9$ is —H, —CH$_3$, Et, Pr, Bu, —NH$_2$, —NHMe, —NMe$_2$, —NHEt or —NEt$_2$. In some embodiments, $R^9$ is —H, —CH$_3$, Et, Pr, —NH$_2$, —NHMe or —NMe$_2$. In some embodiments, $R^9$ is —CH$_3$, Et or Pr. In some embodiments, $R^9$ is Pr.

In some embodiments, $R^{10}$ is —CH$_3$, Et, Pr, $^i$Pr, Bu, sec-butyl, $^i$Bu, tert-Bu, pentyl, tert-pentyl, isopentyl, sec-pentyl, 3-pentyl or hexyl. In some embodiments, $R^{10}$ is —CH$_3$, Et, Pr, $^i$Pr or Bu. In some embodiments, $R^{10}$ is —CH$_3$, Et, or Pr. In some embodiments, $R^{10}$ is —CH$_3$.

In some embodiments, a repeating unit is:

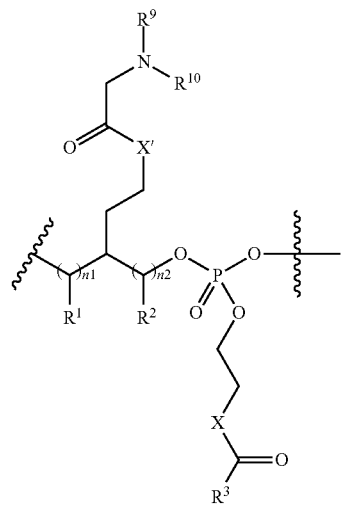

wherein each of $R^1$, $R^2$, $R^3$, $R^9$, $R^{10}$, n1, n2, X, and X' is as defined and described in embodiments above and below, both singly and in combination.

In some embodiments, $R^9$ is —H, —CH$_3$, Et, Pr, Bu, —NH$_2$, —NHMe, —NMe$_2$, —NHEt or —NEt$_2$. In some embodiments, $R^9$ is —H, —CH$_3$, Et, Pr, —NH$_2$, —NHMe or —NMe$_2$. In some embodiments, $R^9$ is —CH$_3$, Et or Pr. In some embodiments, $R^9$ is Pr.

In some embodiments, $R^{10}$ is —CH$_3$, Et, Pr, $^i$Pr, Bu, sec-butyl, $^i$Bu, tert-Bu, pentyl, tert-pentyl, isopentyl, sec-pentyl, 3-pentyl or hexyl. In some embodiments, $R^{10}$ is —CH$_3$, Et, Pr, $^i$Pr or Bu. In some embodiments, $R^{10}$ is —CH$_3$, Et, or Pr. In some embodiments, $R^{10}$ is —CH$_3$.

In some embodiments, a repeating unit is:

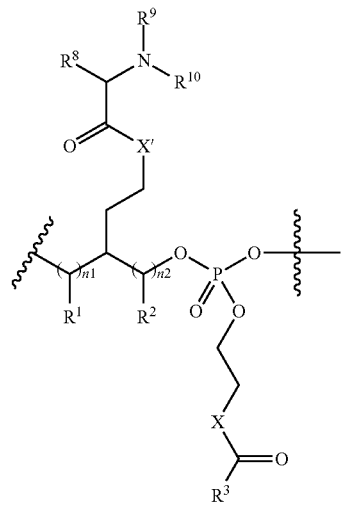

wherein each of $R^1$, $R^2$, $R^3$, $R^8$, $R^9$, $R^{10}$, n1, n2, X, and X' is as defined and described in embodiments above and below, both singly and in combination.

In some embodiments, $R^8$ is —H, —CH$_3$, Et, Pr, Bu, —NH$_2$, —NHMe, —NMe$_2$, —NHEt or —NEt$_2$. In some embodiments, $R^8$ is —H, —CH$_3$, Et, Pr, —NH$_2$, —NHMe or —NMe$_2$. In some embodiments, $R^8$ is —CH$_3$, Et or Pr. In some embodiments, $R^8$ is Pr.

In some embodiments, R⁹ is —H, —CH₃, Et, Pr, ⁱPr, Bu, sec-butyl, ⁱBu, tert-Bu, pentyl, tert-pentyl, isopentyl, sec-pentyl, 3-pentyl or hexyl. In some embodiments, R⁹ is —CH₃, Et, Pr, ⁱPr, Bu, sec-butyl, ⁱBu, tert-Bu, pentyl, tert-pentyl, isopentyl, sec-pentyl, 3-pentyl or hexyl. In some embodiments, R⁹ is —CH₃, Et, Pr, ⁱPr or Bu. In some embodiments, R⁹ is —CH₃, Et or Pr. In some embodiments, R⁹ is —CH₃.

In some embodiments, R¹⁰ is —H, —CH₃, Et, Pr, Bu, —(CH₂)₃NH₂, —(CH₂)₄NH₂ or —(CH₂)₅NH₂. In some embodiments, R¹⁰ is —H, —CH₃, Et, —(CH₂)₄NH₂ or —(CH₂)₅NH₂. In some embodiments, R¹⁰ is —H or —(CH₂)₄NH₂. In some embodiments, R¹⁰ is —(CH₂)₄NH₂.

In some embodiments, a repeating unit is:

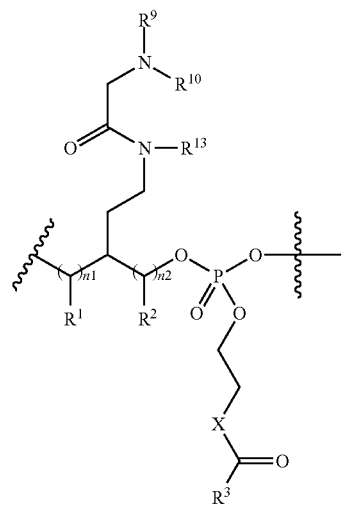

wherein each of R¹, R², R³, R⁹, R¹⁰, R¹³, X, n1, and n2 is as defined and described in embodiments of formula (VII), above, and in embodiments of formula (VIId), below, both singly and in combination.

In some embodiments, R⁹ is —H, —CH₃, Et, Pr, Bu, —NH₂, —NHMe, —NMe₂, —NHEt or —NEt₂. In some embodiments, R⁹ is —H, —CH₃, Et, Pr, —NH₂, —NHMe or —NMe₂. In some embodiments, R⁹ is —CH₃, Et or Pr. In some embodiments, R⁹ is Pr.

In some embodiments, R¹⁰ is —CH₃, Et, Pr, ⁱPr, Bu, sec-butyl, ⁱBu, tert-Bu, pentyl, tert-pentyl, isopentyl, sec-pentyl, 3-pentyl or hexyl. In some embodiments, R¹⁰ is —CH₃, Et, Pr, ⁱPr or Bu. In some embodiments, R¹⁰ is —CH₃, Et, or Pr. In some embodiments, R¹⁰ is —CH₃.

In some embodiments, R¹³ is —H, —CH₃, Et, Pr, ⁱPr, Bu, hexyl, cyclopropyl, cyclobutyl, cyclopentyl or cyclohexyl. In some embodiments, R¹³ is —H, —CH₃, Et, cyclopropyl or cyclobutyl. In some embodiments, R¹³ is —H, —CH₃ or cyclopropyl. In some embodiments, R¹³ is —H.

In some embodiments, a repeating unit is:

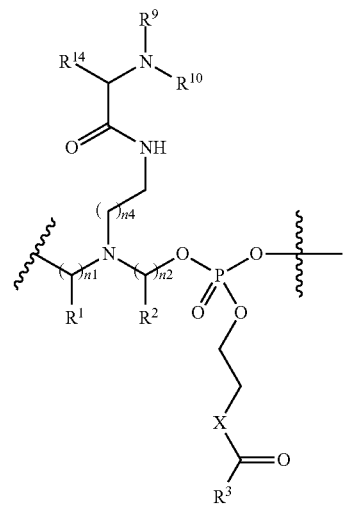

or a pharmaceutically acceptable salt thereof, wherein:
R¹⁴ is a side chain of an amino acid (e.g., a naturally-occurring amino acid);
n4 is 0, 1, 2 or 3;
each of R⁹ and R¹⁰ is —H or is a C₁-C₂₀ aliphatic (e.g., a C₁₋₆ aliphatic, C₁₋₄ haloalkyl or C₃₋₆ cycloalkyl, each of which is optionally substituted with 1-4 occurrences of R*).
each instance of R* independently is halogen, —CO₂R^{J1}, —CN, —OH, —OR^{J1}, —NH₂, —NHR^{J1}, —N(R^{J1})₂, —SR^{J1} or —SO₂R^{J1},
wherein each instance of R^{J1} independently is C₁₋₃ alkyl; and
each of R, R¹, R², R³, X, n1 and n2 is as defined above, both singly and in combination.

In some embodiments, n4 is 1, 2 or 3; or n4 is 1 or 2; or n4 is 2 or 3; or n4 is 1.

In some embodiments, R⁹ is —H, —CH₃, Et, Pr, Bu, —NH₂, —NHMe, —NMe₂, —NHEt, or —NEt₂; or R⁹ is —H, —CH₃, Et, Pr, —NH₂, —NHMe, or —NMe₂; or R⁹ is —CH₃, Et, or Pr; or R⁹ is Pr.

In some embodiments, R¹⁰ is —CH₃, Et, Pr, ⁱPr, Bu, sec-butyl, ⁱBu, tert-Bu, pentyl, tert-pentyl, isopentyl, sec-pentyl, 3-pentyl or hexyl; or R¹⁰ is —CH₃, Et, Pr, ⁱPr or Bu; or R¹⁰ is —CH₃, Et or Pr; or R¹⁰ is —CH₃.

In some embodiments, R¹⁴ is a side chain of alanine, valine, leucine, isoleucine, methionine, phenylalanine, tryptophan, proline, serine, threonine, cysteine, tyrosine, asparagine, lysine, arginine or histidine; or R¹⁴ is a side chain of tryptophan, proline, serine, threonine, cysteine, tyrosine, asparagine, lysine, arginine or histidine; or R¹⁴ is a side chain of lysine or histidine.

In some embodiments, n4 is 1, 2 or 3. In some embodiments, n4 is 1 or 2. In some embodiments, n4 is 2 or 3. In some embodiments, n4 is 1.

In some embodiments, R⁹ is —H, —CH₃, Et, Pr, Bu, —NH₂, —NHMe, —NMe₂, —NHEt, or —NEt₂. In some embodiments, R⁹ is —H, —CH₃, Et, Pr, —NH₂, —NHMe, or —NMe₂. In some embodiments, R⁹ is —CH₃, Et, or Pr. In some embodiments, R⁹ is Pr.

In some embodiments, R¹⁰ is —CH₃, Et, Pr, ⁱPr, Bu, sec-butyl, ⁱBu, tert-Bu, pentyl, tert-pentyl, isopentyl, sec-pentyl, 3-pentyl or hexyl. In some embodiments, R¹⁰ is —CH₃, Et, Pr, ⁱPr or Bu. In some embodiments, R¹⁰ is —CH₃, Et or Pr. In some embodiments, R¹⁰ is —CH₃.

In some embodiments, $R^{14}$ is a side chain of alanine, valine, leucine, isoleucine, methionine, phenylalanine, tryptophan, proline, serine, threonine, cysteine, tyrosine, asparagine, lysine, arginine or histidine. In some embodiments, $R^{14}$ is a side chain of tryptophan, proline, serine, threonine, cysteine, tyrosine, asparagine, lysine, arginine or histidine. In some embodiments, $R^{14}$ is a side chain of lysine or histidine.

In some embodiments, $R^{14}$ is —H, —$CH_3$, $^iPr$, $^iBu$, sec-butyl, —$CH_2OH$, —$CH_2SH$,

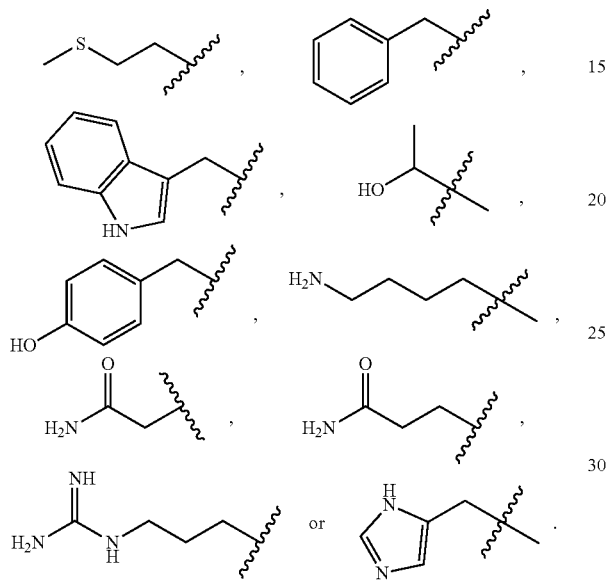

In some embodiments, $R^{14}$ is —$CH_2SH$, —$CH_2OH$,

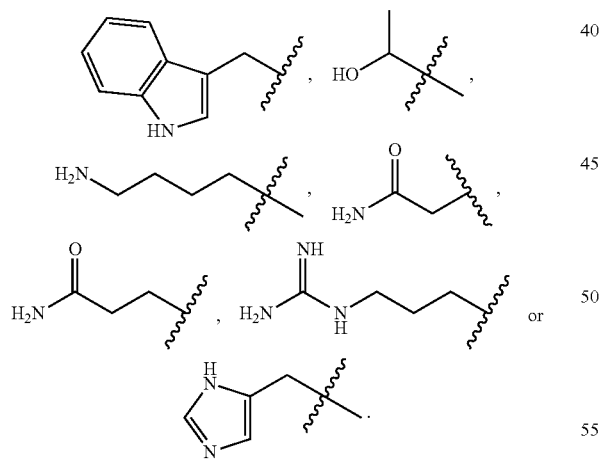

In some embodiments, $R^{14}$ is

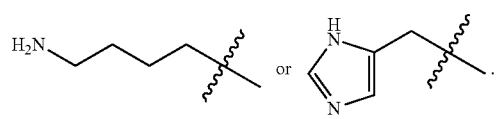 [SMILES: *CCCCN ; *Cc1cnc[nH]1]

In some embodiments, a repeating unit is:

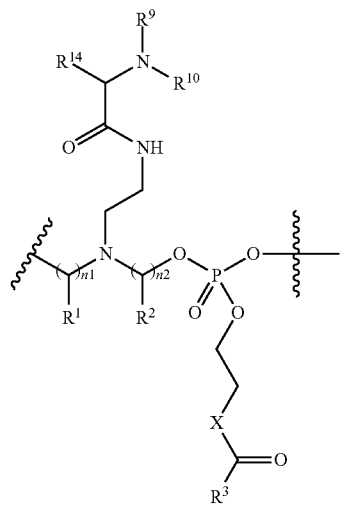

wherein each of $R^1$, $R^2$, $R^3$, $R^9$, $R^{10}$, $R^{14}$, X, n1, and n2 is as defined and described in embodiments above, both singly and in combination.

In some embodiments, a repeating unit is:

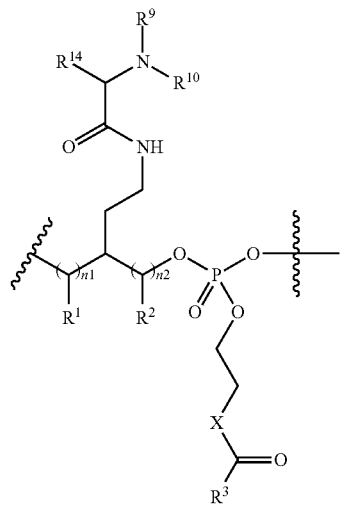

wherein each of $R^1$, $R^2$, $R^3$, $R^9$, $R^{10}$, $R^{14}$, X, n1, and n2 is as defined and described in embodiments above, both singly and in combination.

In some embodiments, a repeating unit is:

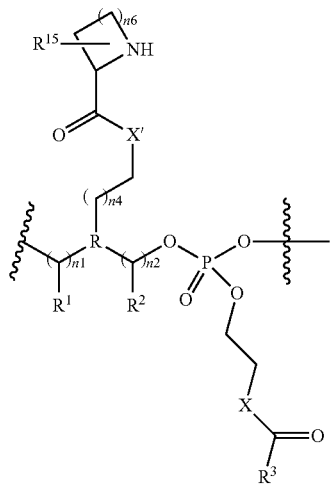

or a pharmaceutically acceptable salt thereof, wherein:
X' is —O— or —NR$^{13}$—, wherein
R$^{13}$ is —H, C$_{1-6}$ aliphatic or C$_{3-6}$ cycloalkyl;
n4 is 0, 1, 2 or 3;
n$^{15}$ is —H or C$_{1-6}$alkyl;
n6 is 1, 2, 3 or 4; and
each of R, R$^1$, R$^2$, R$^3$, X, n1 and n2 is as defined above, both singly and in combination.

In some embodiments, X is —O— or —NH—; or X is —O—; or X is —NH—.

In some embodiments, n4 is 1, 2 or 3; or n4 is 1 or 2; or n4 is 2 or 3; or n4 is 1.

In some embodiments, n6 is 1, 2, 3 or 4; or n6 is 2 or 3; or n6 is 2.

In some embodiments, R$^{15}$ is —H, —CH$_3$, Et, Pr, $^i$Pr, Bu, sec-butyl, $^i$Bu, tert-Bu, pentyl, tert-pentyl, isopentyl, sec-pentyl, 3-pentyl or hexyl; or R$^{15}$ is —H, —CH$_3$, Et, Pr, $^i$Pr, or Bu; or R$^{15}$ is —H, —CH$_3$, or Et, or Pr; or R$^{15}$ is —H.

In some embodiments, X is —O— or —NH—. In some embodiments, X is —O—. In some embodiments X is —NH—.

In some embodiments, n4 is 1, 2 or 3. In some embodiments, n4 is 1 or 2. In some embodiments, n4 is 2 or 3. In some embodiments, n4 is 1.

In some embodiments, n6 is 1, 2, 3 or 4. In some embodiments, n6 is 2 or 3. In some embodiments n6 is 2.

In some embodiments, R$^{15}$ is —H, —CH$_3$, Et, Pr, $^i$Pr, Bu, sec-butyl, $^i$Bu, tert-Bu, pentyl, tert-pentyl, isopentyl, sec-pentyl, 3-pentyl or hexyl. In some embodiments, R$^{15}$ is —H, —CH$_3$, Et, Pr, $^i$Pr, or Bu. In some embodiments, R$^{15}$ is —H, —CH$_3$, or Et, or Pr. In some embodiments, R$^{15}$ is —H.

In some embodiments, n6 is 2 or 3 and R$^{15}$ is —H, —CH$_3$, Et or Pr. In some embodiments, n6 is 2 and R$^{15}$ is —H or —CH$_3$. In some embodiments, n6 is 2 and R$^{15}$ is —H.

In some embodiments, a repeating unit is:

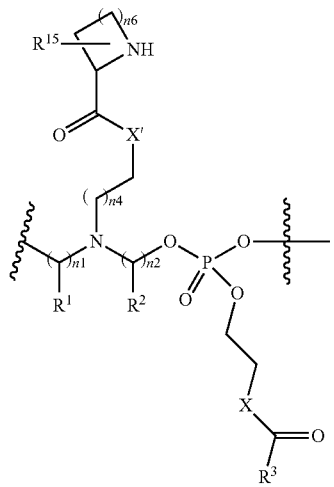

wherein each of R$^1$, R$^2$, R$^3$, R$^{15}$, X, n1, n2 and n6 is as defined and described in embodiments of above, both singly and in combination.

In some embodiments, a repeating unit is:

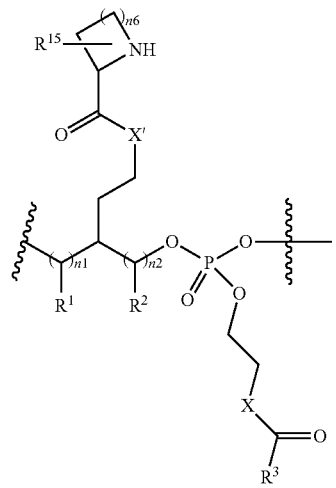

wherein each of R$^1$, R$^2$, R$^3$, R$^{15}$, X, n1, n2 and n6 is as defined and described in embodiments of formula (IX), above, both singly and in combination.

Examples of polymers of the present invention include those comprising
a repeating group that is

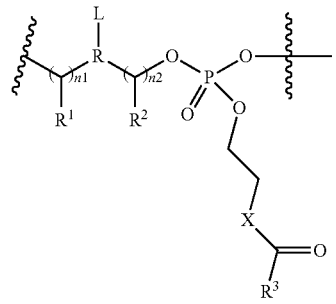

wherein:
   each instance of $R^1$ independently is —H or a $C_1$-$C_{20}$ aliphatic group;
   each instance of $R^2$ independently is —H or a $C_1$-$C_{20}$ aliphatic group;
   each instance of $R^3$ independently is —H or a $C_1$-$C_{20}$ aliphatic group;
   X is independently S or O;
   n1 is an integer from 1 to 6;
   n2 is an integer from 1 to 6; and
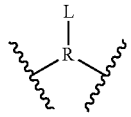
is any of the following:
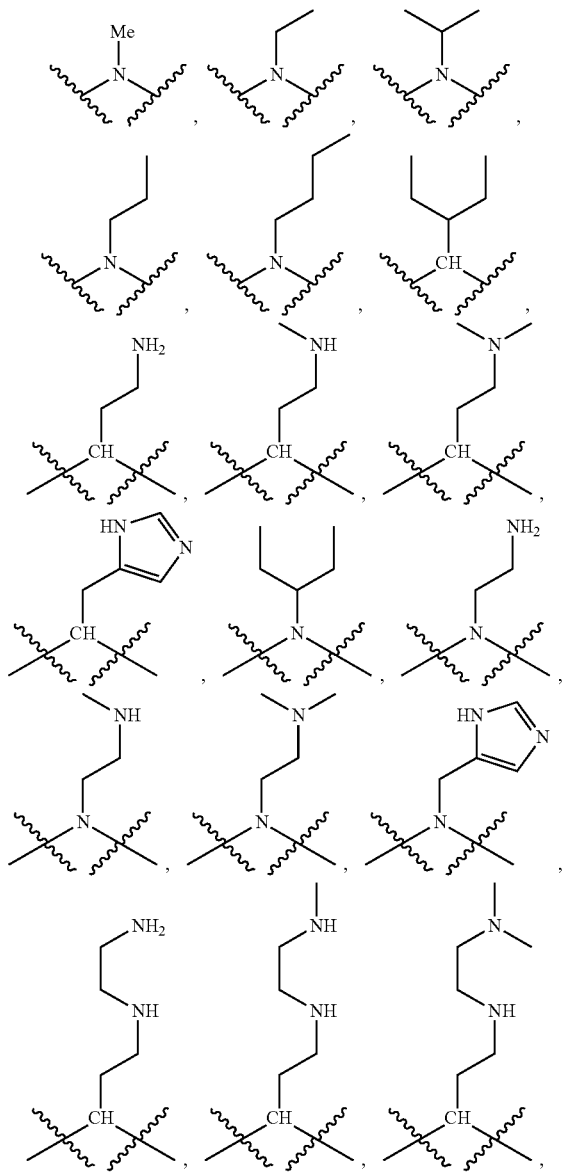
-continued
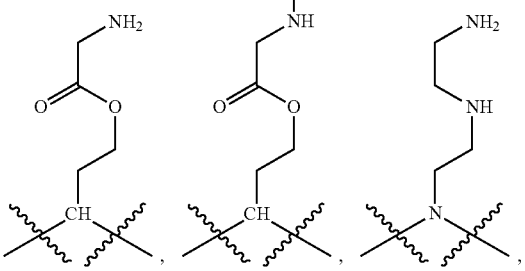
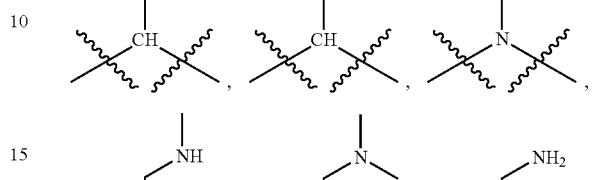
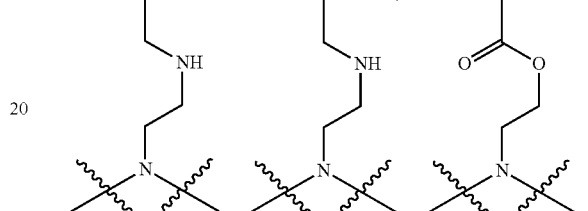
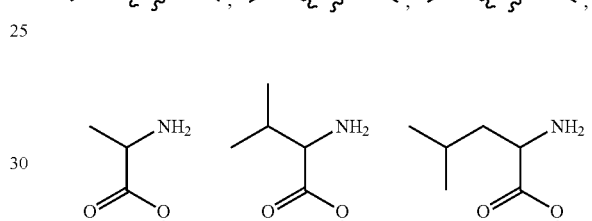
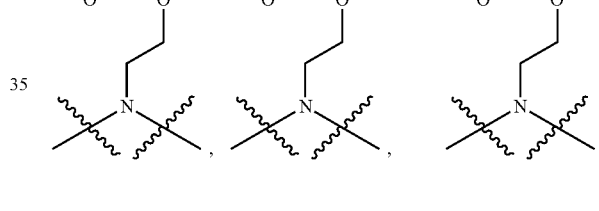
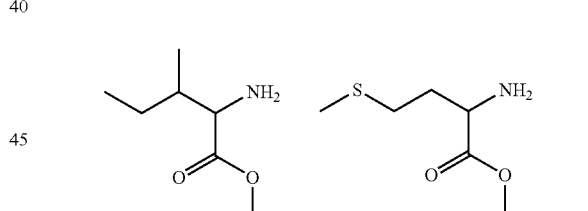
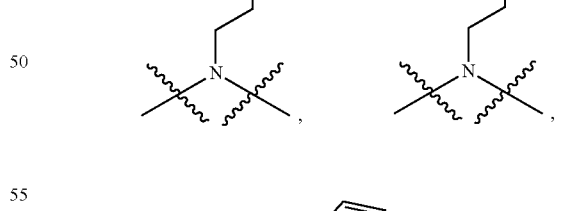
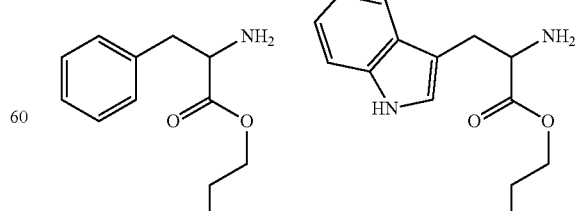

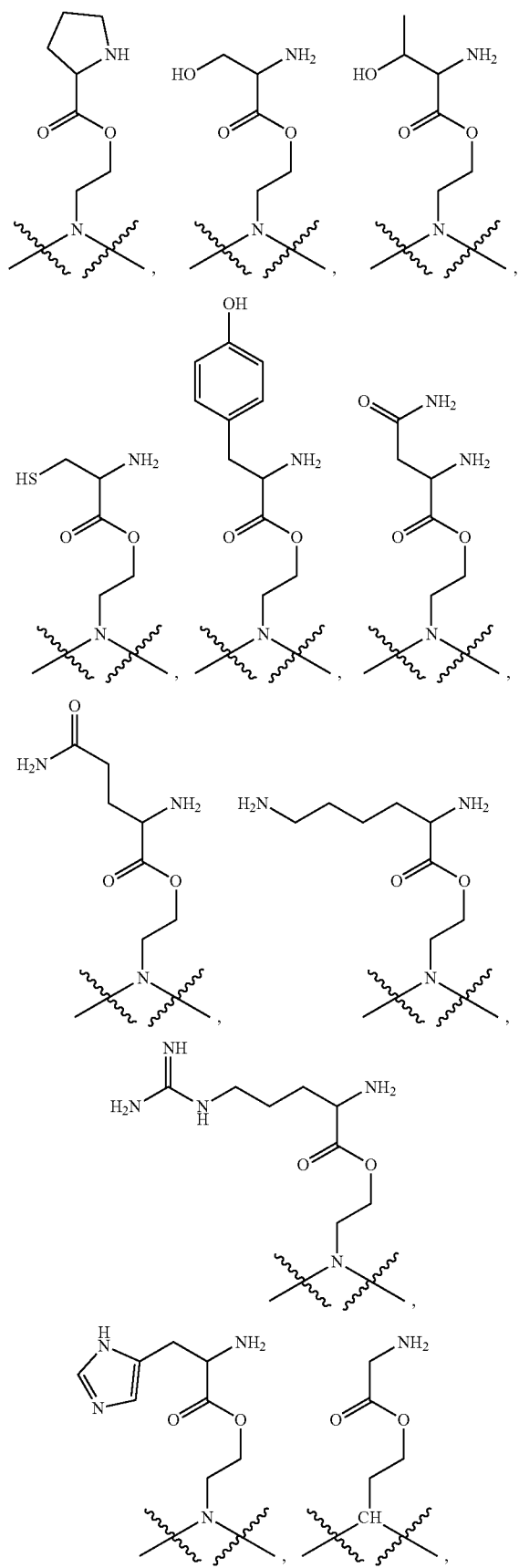
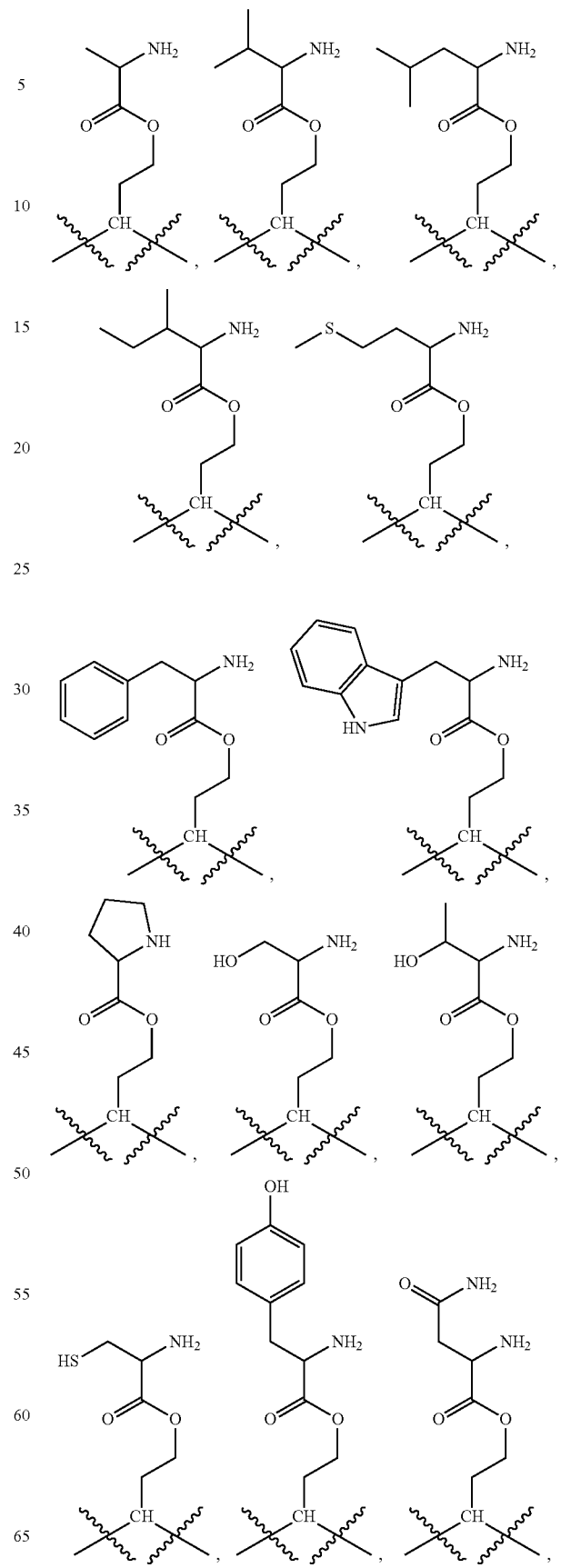

-continued

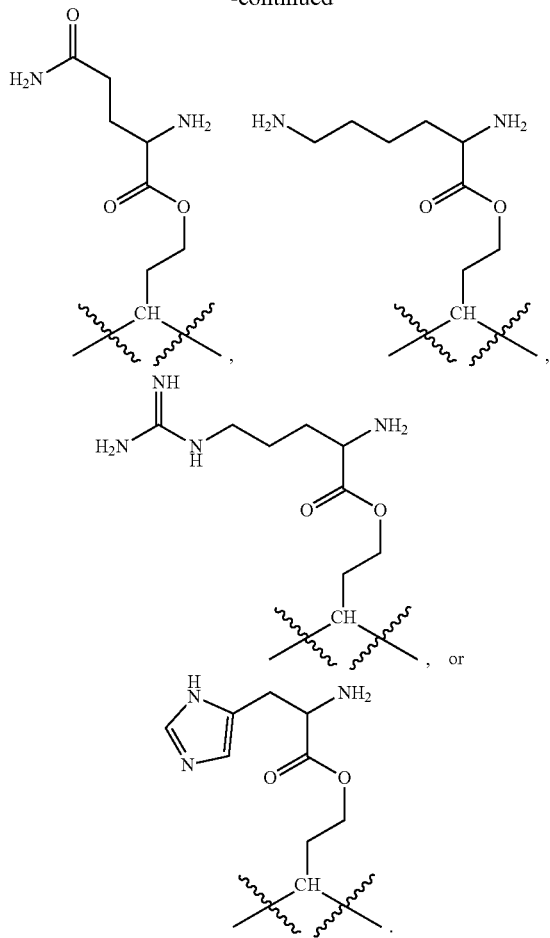

In some embodiments, $R^1$ independently is —H, —CH$_3$ or —CH$_2$CH$_3$.

In some embodiments, $R^2$ independently is —H, —CH$_3$ or —CH$_2$CH$_3$.

In some embodiments, $R^3$ independently is —H, —CH$_3$, —CH$_2$CH$_3$, —CH$_2$CH$_2$CH$_3$, CH(CH$_3$)$_2$, or C(CH$_3$)$_3$.

In some embodiments, X is independently O.

In some embodiments, X is independently S.

Polymers

In some aspects, the present invention provides a polymer comprising the moiety A: $-\!\!+\!\!A\!\!+\!\!-$, which is a repeating unit as defined above (a "provided polymer").

In some embodiments, a provided polymer is a homopolymer. In some embodiments, a provided homopolymer comprises the structure:

wherein m is an integer such that the weight average molecular weight (Mw) of the polymer is about 10 kDa to about 60 kDa.

In some embodiments, m is an integer such that $M_w$ is about 10 kDa to about 60 kDa, about 10 kDa to about 50 kDa, about 10 kDa to about 40 kDa, about 10 kDa to about 30 kDa about 15 kDa to about 60 kDa, about 15 kDa to about 50 kDa, about 15 kDa to about 40 kDa, or about 15 kDa to about 30 kDa.

In some embodiments, the moiety:

constitutes at least 10%, at least 20%, at least 30%, at least 40%, at least 50%, at least 60%, at least 65%, at least 70%, at least 75%, at least 80%, at least 85%, at least 90% or at least 95% of the total $M_w$ of the polymer.

In some embodiments, a provided polymer is a copolymer.

In some embodiments, a copolymer is a controlled di-block copolymer. In some embodiments, a copolymer is a controlled tri-block copolymer. In some embodiments, a copolymer is a mixed polymer. In some embodiments, a copolymer is an alternating copolymer. In some embodiments, a copolymer is a random copolymer. In some embodiments, a copolymer is a graft copolymer. In some embodiments, a copolymer is a periodic copolymer. In some embodiments, a copolymer is a statistical copolymer. In embodiments a copolymer is linear. In some embodiments, a copolymer is a linear copolymer. In some embodiments, a copolymer is a branched copolymer.

In some embodiments, a provided copolymer comprises two different segments:

$m_1$ instances of $-\!\!+\!\!A\!\!+\!\!-$ and $m_2$ instances of $-\!\!+\!\!B\!\!+\!\!-$, wherein:

A is a repeating unit as described above;

B is a structurally distinct repeating unit from A (e.g., B is a moiety of formula (I) as described above but different from A); and $m_1$ and $m_2$ are integers such that the weight average molecular weight ($M_w$) of the polymer is about 10 kDa to about 60 kDa.

In some embodiments, B is a repeating unit as described above but different from A.

In some embodiments, B does not comprise any ionizable group. In some embodiments, B is neutral. In some embodiments, B is uncharged. In some embodiments, B is negatively charged. In some embodiments, B is positively charged.

In some embodiments, B is a targeting group (e.g., a targeting group as described herein).

In some embodiments, B is biodegradable. In embodiments, B is non-biodegradable.

In some embodiments, B is a moiety that is a hydrocarbon (e.g., a saturated hydrocarbon or an unsaturated hydrocarbon).

In some embodiments, B is a moiety that is a lactide (e.g., L-lactide or D,L-lactide), glycolide, ethylene glycol, caprolactone, propylene fumarate, or a 2-oxazoline.

In some embodiments, $m_1$ and $m_2$ are integers such that $M_w$ is about 10 kDa to about 60 kDa, about 10 kDa to about 50 kDa, about 10 kDa to about 40 kDa, about 10 kDa to about 30 kDa about 15 kDa to about 60 kDa, about 15 kDa to about 50 kDa, about 15 kDa to about 40 kDa, or about 15 kDa to about 30 kDa.

In some embodiments, the $m_1$ instances of $-\!\!+\!\!A\!\!+\!\!-$ and $m_2$ instances of $-\!\!+\!\!B\!\!+\!\!-$ together constitute at least 10%, at least 20%, at least 30%, at least 40%, at least 50%, at least 60%, at least 65%, at least 70%, at least 75%, at least 80%, at least 85%, at least 90% or at least 95% of the total $M_w$ of the polymer.

In some embodiments, a provided copolymer is an alternating copolymer. In some embodiments, a provided alternating copolymer comprises the structure:

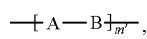

wherein m' is an integer such that the weight average molecular weight (Mw) of the polymer is about 10 kDa to about 60 kDa.

In some embodiments, m' is an integer such that $M_w$ is about 10 kDa to about 60 kDa, about 10 kDa to about 50 kDa, about 10 kDa to about 40 kDa, about 10 kDa to about 30 kDa about 15 kDa to about 60 kDa, about 15 kDa to about 50 kDa, about 15 kDa to about 40 kDa, or about 15 kDa to about 30 kDa.

In some embodiments, the moiety:

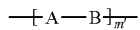

constitutes at least 10%, at least 20%, at least 30%, at least 40%, at least 50%, at least 60%, at least 65%, at least 70%, at least 75%, at least 80%, at least 85%, at least 90% or at least 95% of the total $M_w$ of the polymer.

In some embodiments, a provided copolymer is an block copolymer. In some embodiments, a provided block copolymer comprises the structure:

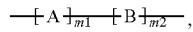

wherein $m_1$ and $m_2$ are integers such that the weight average molecular weight ($M_w$) of the polymer is about 10 kDa to about 60 kDa.

In some embodiments, $m_1$ and $m_2$ are integers such that $M_w$ is about 10 kDa to about 60 kDa, about 10 kDa to about 50 kDa, about 10 kDa to about 40 kDa, about 10 kDa to about 30 kDa about 15 kDa to about 60 kDa, about 15 kDa to about 50 kDa, about 15 kDa to about 40 kDa, or about 15 kDa to about 30 kDa.

In some embodiments, the moiety:

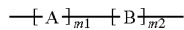

constitutes at least 10%, at least 20%, at least 30%, at least 40%, at least 50%, at least 60%, at least 65%, at least 70%, at least 75%, at least 80%, at least 85%, at least 90% or at least 95% of the total $M_w$ of the polymer.

In some embodiments, a provided polymer comprises the moiety: ─[A─]T,
wherein:
A is a repeating unit as described above; and
T is a targeting group.

In embodiments, a provided polymer has hydrogen endgroups.

In embodiments, a provided polymer has oxygen-containing endgroups (e.g., hydroxyl or a $C_{1-6}$ alkoxyl).

In embodiments, a provided polymer has alkyl-containing endgroups (e.g., a $C_{1-6}$ alkyl).

In some embodiments, the targeting group of a polymer is a moiety that may interact with a biological target of interest via a biological binding event, i.e., between complementary pairs of biological molecules. For example, a targeting group may comprise an entity such as biotin that specifically binds to a complementary entity, such as avidin or streptavidin. Other examples of interactions that occur between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair.

In some embodiments, the inclusion of a, S-acyl-2-thioethyl (SATE) protecting group is employed. Such a protecting group is readily cleavable through esterase enzymatic activity resulting in a liberated phosphate functional group (Scheme 1). Upon cleavage of the SATE group, the generation of a negatively charged phosphate moiety is realized. The resulting negative charge can counter-balance the cationic charge of the amino monomer moiety resulting in a zwitterionic region. Upon release of some SATE protecting groups, the polymer is partially neutralized, rendering its ability to bind nucleic acids diminished. Thus, partial release of the nucleic acid payload will occur. Upon release of all SATE protecting groups, the polymer is completely neutralized, rendering its ability to bind nucleic acids removed. Thus, full release of the nucleic acid payload will occur. In total, such a polymer allows for facile complexation with nucleic acids, efficient release of payload and biodegradability of itself.

Scheme 1

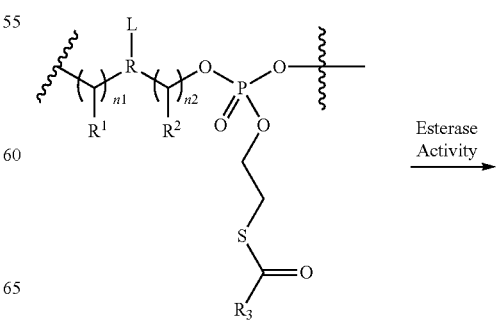

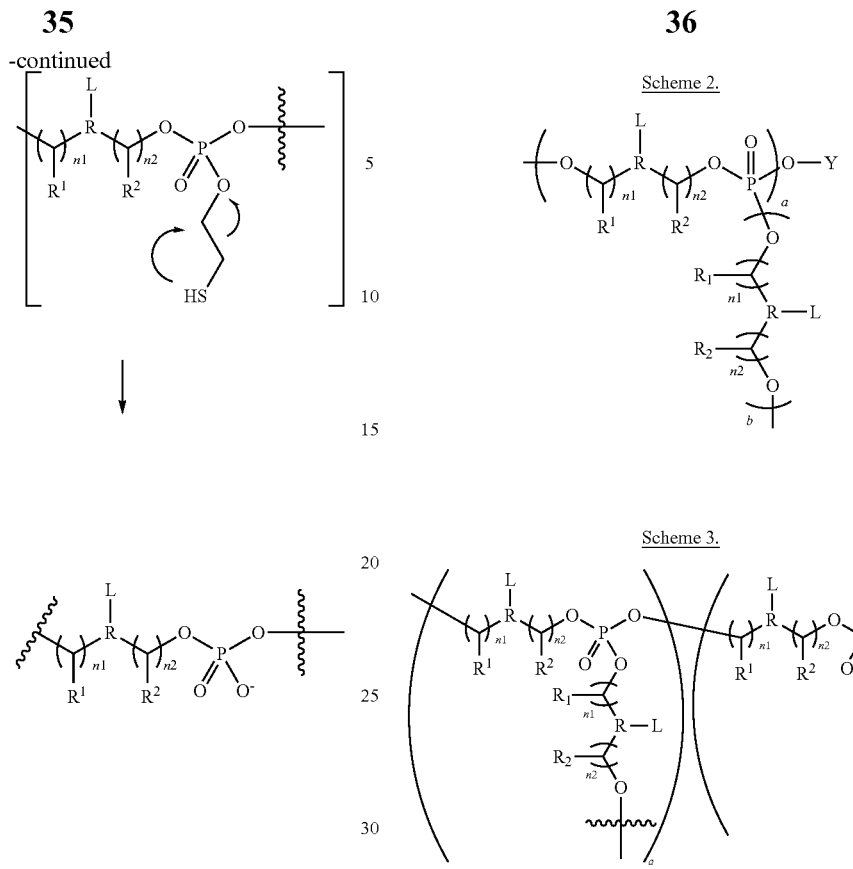

In some embodiments, a branched poly(phosphoester) can be produced via reaction with any diol monomer with a reactive phosphate moiety without inclusion of the S-acyl-thioethanol group (Scheme 2). Further, a mixed branched poly(phosphoester) polymer can be synthesized incorporating both the thioester functionality in selected ratios to afford partial branching (Scheme 3).

Synthetic Methods

In general, the polymers of the invention can be prepared by methods described herein or by other methods known to those skilled in the art. Exemplary preparations of the polymers of the invention are described below.

The following generic schemes and examples illustrate how to prepare the polymers of the present disclosure. For example, stoichiometry of the reagents may be varied in order to obtain the desired monomer or polymer.

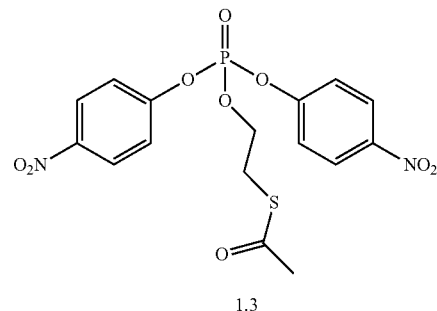

1.3

As shown in pathway A in Scheme 4, above, the intermediate phosphate triester 1.3 can be prepared, e.g., by treating p-nitrophenol with phosphoryl chloride (phosphorus oxychloride) in the presence of a suitable base such as triethylamine to produce intermediate phosphorochloridate 1.1, followed by treatment with S-(2-hydroxyethyl) ethanethioate in the presence of a suitable base such as triethylamine. Alternatively, as shown in pathway B, S-(2-hydroxyethyl) ethanethioate can first be treated with phosphoryl chloride in the presence of, e.g., a suitable base such as triethylamine to produce intermediate 1.2, followed by treatment with p-nitrophenol in the presence of a suitable base such as triethylamine to yield phosphate triester 1.3.

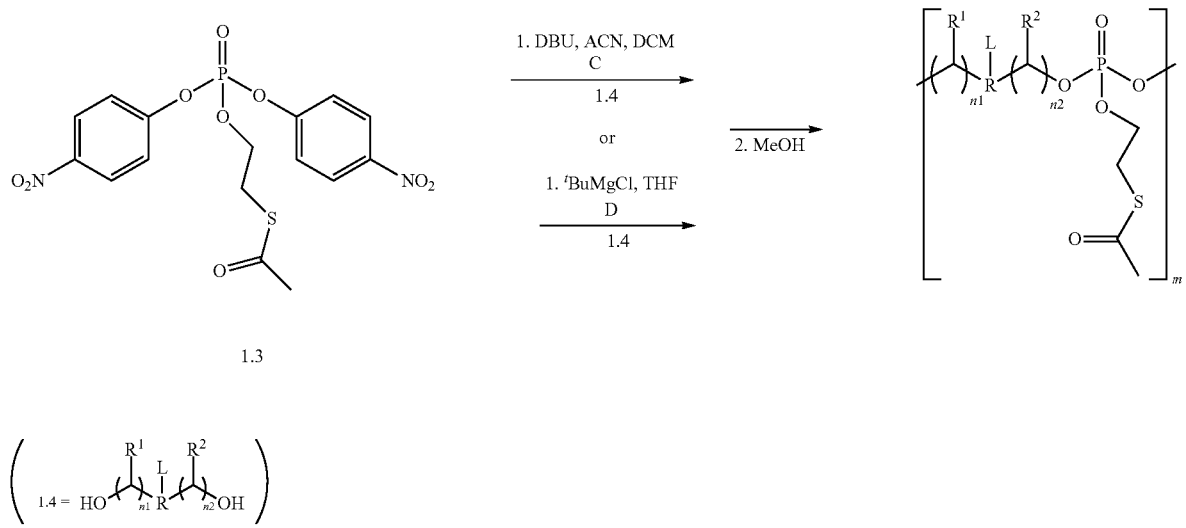

As shown in Scheme 5, above, the intermediate phosphate triester 1.3 can be converted to the moiety of Formula (I) by treatment with, e.g., an appropriately substituted diol 1.4 in the presence of (C) a suitable base such as 1,8-diazabicyclo[5.4.0]undec-7-ene in a suitable solvent or combination of solvents such as acetonitrile/dichloromethane or (D) a suitable Grignard reagent such as tert-butylmagnesium chloride in a suitable solvent such as tetrahydrofuran, followed by treatment with a suitable protic agent such as methanol.

Scheme 6

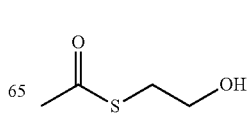

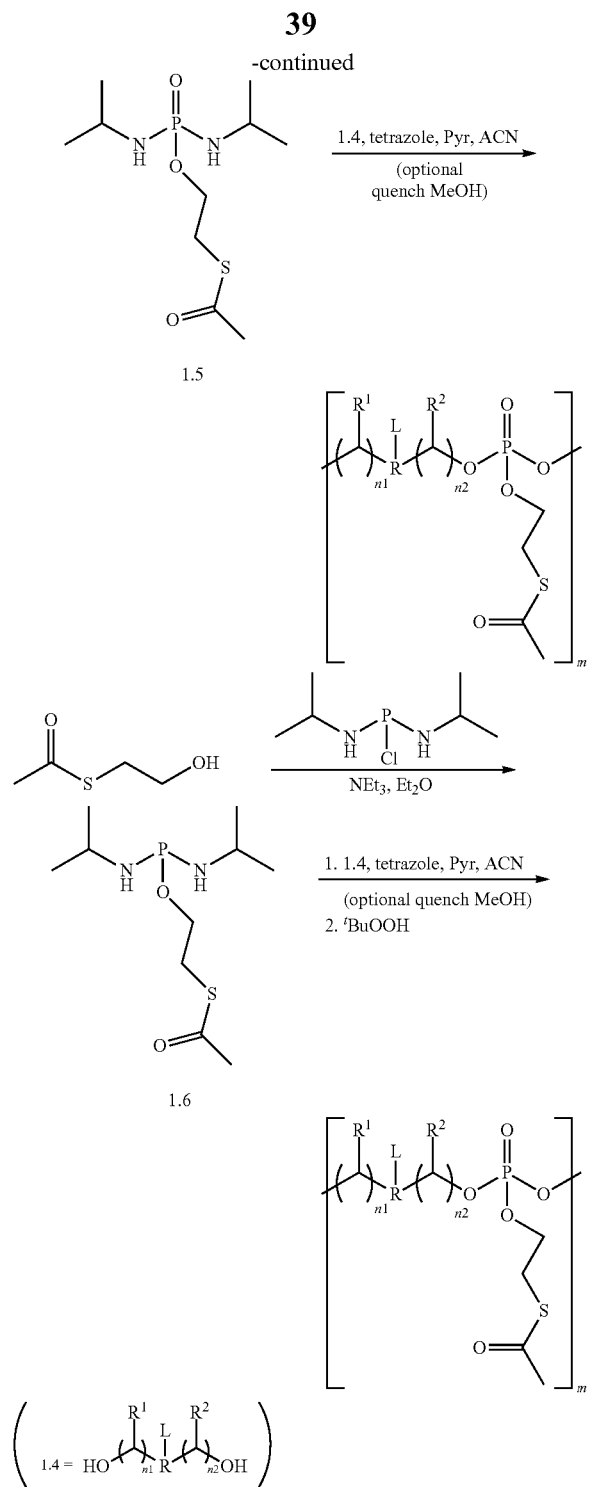

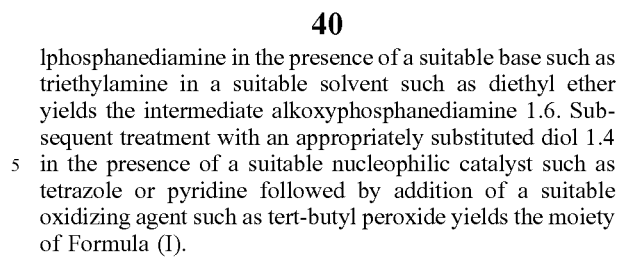

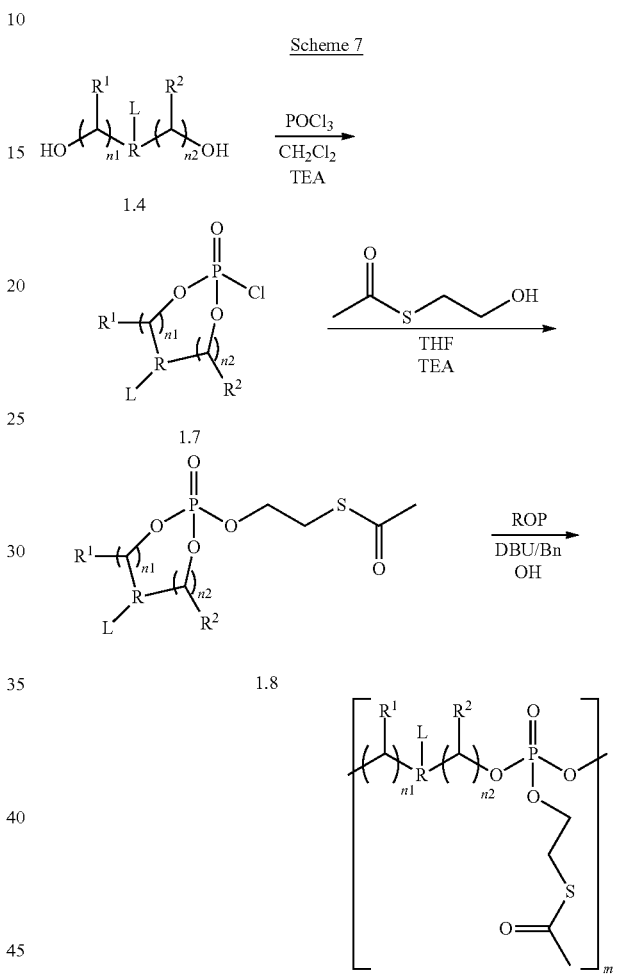

Scheme 6, above, illustrates alternative routes to the moiety of Formula (I). For example, treatment of S-(2-hydroxyethyl) ethanethioate with N,N'-diisopropylphosphorodiamidic chloride in the presence of a suitable base such as triethylamine in a suitable solvent such as diethyl ether yields the intermediate phosphorodiamidate 1.5. Subsequent treatment with an appropriately substituted diol 1.4 in the presence of a suitable base such as nucleophilic catalysts or combinations thereof (e.g., tetrazole and/or pyridine) yields the moiety of Formula (I). Alternatively, treatment of S-(2-hydroxyethyl) ethanethioate with 1-chloro-N,N'-diisopropylphosphanediamine in the presence of a suitable base such as triethylamine in a suitable solvent such as diethyl ether yields the intermediate alkoxyphosphanediamine 1.6. Subsequent treatment with an appropriately substituted diol 1.4 in the presence of a suitable nucleophilic catalyst such as tetrazole or pyridine followed by addition of a suitable oxidizing agent such as tert-butyl peroxide yields the moiety of Formula (I).

Scheme 7, above, illustrates another alternative route to the moiety of Formula (I). Treatment of an appropriately substituted diol 1.4 with phosphoryl chloride (phosphorus oxychloride) in a suitable solvent such as methylene chloride (dichloromethane) in the presence of a suitable base such as triethylamine yields intermediate phosphorochloridate 1.7. Subsequent treatment of 1.7 with of S-(2-hydroxyethyl) ethanethioate in a suitable solvent such as tetrahydrofuran in the presence of a suitable base such as triethylamine yields phosphate triester 1.8. Ring-opening polymerization (ROP) of 1.8 yields the moiety of Formula (I).

Specific examples of poly(phosphoester) preparation are described in the following paragraphs.

Nucleic Acids

Synthesis of Nucleic Acids

Nucleic acids according to the present invention may be synthesized according to any known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, mutated T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7, mutated T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified Nucleic Acids

Modified nucleic acids according to the present invention may be include modifications and be prepared according to any known modifications and methods. For example, in some embodiments, mRNA according to the present invention may be synthesized as unmodified RNA or as modified RNA in accordance with known modifications and methods. Typically, RNAs are modified to enhance stability. Modifications of RNA can include, for example, modifications of the nucleotides of the RNA. A modified RNA such as modified mRNA (mmRNA) according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, modified RNAs such as mmRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, modified RNAs such as mmRNAs may contain sugar modifications. A typical sugar modification is a chemical modification of the sugar of the nucleotides it contains including, but not limited to, sugar modifications chosen from the group consisting of 4'-thio-ribonucleotide (see, e.g., US Patent Application Publication No. US 2016/0031928, incorporated by reference herein), 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, modified RNAs such as mmRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs include a 3' poly(A) tail structure. A poly-A tail on the 3' terminus of mRNA typically includes about 10 to 300 adenosine nucleotides (SEQ ID NO: 4) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO: 5) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of synthetic dinucleotide cap used in in vitro translation experiments is the Anti-Reverse Cap Analog ("ARCA") or modified ARCA, which is generally a modified cap analog in which the 2' or 3' OH group is replaced with —$OCH_3$.

Additional cap analogs include, but are not limited to, a chemical structures selected from the group consisting of $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{7,2'd}GpppG$, $m^{7,3'Ome}GpppG$, $m^{7,3'd}GpppG$ and their tetra phosphate derivatives) (see, e.g., Jemielity, J. et al., "*Novel 'anti-reverse' cap analogs with superior translational properties*", RNA, 9: 1108-1122 (2003)).

In some embodiments, a suitable cap is a 7-methyl guanylate ("$m^7G$") linked via a triphosphate bridge to the 5'-end of the first transcribed nucleotide, resulting in $m^7G$ (5')ppp(5')N, where N is any nucleoside. A preferred embodiment of a $m^7G$ cap utilized in embodiments of the invention is $m^7G(5')ppp(5')G$.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of $m^7G$ cap analogs are known in the art, many of which are commercially available. These include the $m^7GpppG$ described above, as well as the ARCA 3'-$OCH_3$ and 2'-$OCH_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Pharmaceutical Formulations of Polymers and Nucleic Acids

Among other things, the present invention provides a pharmaceutical formulation comprising a provided polymer and one or more nucleic acids. As described below, such a polymer-based formulation for delivering nucleic acids can provide one or more advantages in delivering nucleic acids, such as mRNA, for providing a therapeutic benefit, such as producing encoded protein (where the nucleic acid is mRNA), over existing polymers.

In one aspect, the invention features a pharmaceutical composition comprising a polymer as described herein and one or more polynucleotides.

In embodiments, a polynucleotide comprises RNA (e.g., mRNA, siRNA, snoRNA, microRNA, gRNA, crRNA and combinations thereof).

In embodiments, an RNA is mRNA.

I mRNA encodes a peptide or polypeptide for use in the delivery to or treatment of the lung of a subject or a lung cell. In embodiments, an mRNA encodes cystic fibrosis transmembrane conductance regulator (CFTR) protein.

mRNA encodes a peptide or polypeptide for use in the delivery to or treatment of the liver of a subject or a liver cell. In embodiments, an mRNA encodes ornithine transcarbamylase (OTC) protein.

In embodiments, an mRNA encodes a peptide or polypeptide for use in vaccine. In embodiments, an mRNA encodes an antigen.

In general, the polymer and nucleic acids such as mRNA are first mixed in a solution, e.g., an aqueous solution. Typically, the polymer and nucleic acids such as mRNA form a complex when mixed. In some embodiments, the polymer and nucleic acids are complexed in a form of nanoparticles.

Various sized nanoparticles may be formed according to the present invention. In various embodiments, a nanoparticle is characterized with an average diameter based on volume diameter using dynamic light scattering. In some embodiments, nanoparticles have an average diameter between about 50 nm and about 250 nm. In some embodiments, nanoparticles have an average diameter between about 50 nm and about 200 nm. In some embodiments, nanoparticles have an average diameter between about 75 nm and about 225 nm. In some embodiments, nanoparticles have an average diameter between about 100 nm and about 200 nm. In some embodiments, nanoparticles have an average diameter between about 125 nm and about 175 nm. In some embodiments, nanoparticles have an average diameter between about 140 nm and about 160 nm. In some embodiments, nanoparticles have an average diameter between about 50 nm and about 150 nm. In some embodiments, nanoparticles have an average diameter between about 75 nm and about 125 nm. In some embodiments, nanoparticles have an average diameter between about 50 nm and about 250 nm. In some embodiments, nanoparticles have an average diameter between about 90 nm and about 110 nm. In some embodiments, nanoparticles have an average diameter between about 150 nm and about 250 nm. In some embodiments, nanoparticles have an average diameter between about 175 nm and about 225 nm. In some embodiments, nanoparticles have an average diameter between about 190 nm and about 210 nm.

Nanoparticles may have a range of sizes in a mixture. Typically, the nanoparticles have a polydispersity index (PDI) of less than about 0.5 (e.g., less than about 0.45, 0.4, 0.35, 0.3, 0.25, 0.2, 0.15, or 0.1). In some embodiment, the nanoparticles have a PDI between about 0.1 and about 0.4. In some embodiments nanoparticles have a PDI between about 0.1 and about 0.4. In some embodiments nanoparticles have a PDI between about 0.1 and about 0.2. In some embodiments nanoparticles have a PDI between about 0.2 and about 0.3. In some embodiments, nanoparticles have a PDI between about 0.3 and about 0.4.

Nanoparticles may have a range of surface charges as measured through zeta potential measurements. In some embodiments, nanoparticles have a zeta potential between 0 and about 50 mV. In some embodiments nanoparticles have a zeta potential between about 5 and about 45 mV. In some embodiments nanoparticles have a zeta potential between about 10 and about 40 mV. In some embodiments nanoparticles have a zeta potential between about 10 and about 30 mV. In some embodiments nanoparticles have a zeta potential between about 20 and about 30 mV.

Pharmaceutical Formulations and Therapeutic Uses

Pharmaceutical formulations containing provided polymer and nucleic acids provided by the present invention may be used for various therapeutic purposes. Provided polymer-based formulations for delivering nucleic acids can provide one or more advantages in delivering nucleic acids, such as mRNA, for providing a therapeutic benefit, such as producing encoded protein (where the nucleic acid is mRNA), over existing polymers.

Provided polymers are biodegradable. Biodegradable polymers can provide a higher level of tolerability than other polymeric and lipidic delivery vehicles.

Provided polymers are ionizable. The ionizability can be engendered by an amino functionality in the polymer backbone (e.g., R is N) and/or a protonatable group tethered from the backbone. The protonatable group will have at least one 1° amino, 2° amino, 3° amino or imidazolyl functionality. Such ionizable groups can provide a buffering effect and act as a "proton sponge" allowing for enhancement of endosomal release.

Provided polymers incorporate an S-acycl-2-thioethyl ("SATE") protecting group on the phosphate groups within the backbone. Such protection removes the negative charge from the phosphate groups, allowing for facile complexation of the ionizable positively charged polymer with nucleic acids. Upon cellular entry, the SATE protecting groups are biolabile and can be cleaved enzymatically by carboxylesterase. Such cleavage and results in a negatively charged phosphate moiety across the backbone of polymers. This, in effect, neutralizes the polymer charge and thus removes the electrostatic ability of the polymer to bind nucleic acids, e.g., mRNA. This can result in efficient release of the payload nucleic acid.

To facilitate delivery of nucleic acids in vivo, polymer/nucleic acids can be formulated in combination with one or more additional pharmaceutical carriers, targeting ligands or stabilizing reagents. Techniques for formulation and administration of drugs may be found in "Remington's Pharmaceutical Sciences," Mack Publishing Co., Easton, Pa., latest edition.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the nucleic acids to a muscle cell. In some embodiments the administration results in delivery of the nucleic acids to a hepatocyte (i.e., liver cell).

Alternatively or additionally, pharmaceutical formulations of the invention may be administered in a local rather than systemic manner, for example, via injection of the pharmaceutical formulation directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection.

The present invention provides methods for producing a composition enriched with full-length mRNA molecules which are greater than 500 nucleotides in length and encoding for a peptide or polypeptide of interest. The present invention also provides methods for producing a therapeutic composition enriched with full-length mRNA molecules encoding a peptide or polypeptide of interest for use in the delivery to or treatment of a subject, e.g., a human subject or a cell of a human subject or a cell that is treated and delivered to a human subject.

Accordingly, in certain embodiments the present invention provides a method for producing a therapeutic composition enriched with full-length mRNA that encodes a peptide or polypeptide for use in the delivery to or treatment of the lung of a subject or a lung cell. In certain embodiments the present invention provides a method for producing a therapeutic composition enriched with full-length mRNA that encodes for cystic fibrosis transmembrane conductance regulator (CFTR) protein. In certain embodiments the present invention provides a method for producing a therapeutic composition enriched with full-length mRNA that encodes for ATP-binding cassette sub-family A member 3 protein. In certain embodiments the present invention provides a method for producing a therapeutic composition enriched with full-length mRNA that encodes for dynein axonemal intermediate chain 1 protein. In certain embodiments the present invention provides a method for producing a therapeutic composition enriched with full-length mRNA that encodes for dynein axonemal heavy chain 5 (DNAH5) protein. In certain embodiments the present invention provides a method for producing a therapeutic composition enriched with full-length mRNA that encodes for alpha-1-antitrypsin protein. In certain embodiments the present invention provides a method for producing a therapeutic composition enriched with full-length mRNA that encodes for forkhead box P3 (FOXP3) protein. In certain embodiments the present invention provides a method for producing a therapeutic composition enriched with full-length mRNA that encodes one or more surfactant protein, e.g., one or more of surfactant A protein, surfactant B protein, surfactant C protein, and surfactant D protein.

In certain embodiments the present invention provides a method for producing a therapeutic composition enriched with full-length mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition enriched with full-length mRNA that encodes for a protein associated with a urea cycle disorder. In certain embodiments the present invention provides a method for producing a therapeutic composition enriched with full-length mRNA that encodes for ornithine transcarbamylase (OTC) protein. In certain embodiments the present invention provides a method for producing a therapeutic composition enriched with full-length mRNA that encodes for arginosuccinate synthetase 1 protein. In certain embodiments the present invention provides a method for producing a therapeutic composition enriched with full-length mRNA that encodes for carbamoyl phosphate synthetase I protein. In certain embodiments the present invention provides a method for producing a therapeutic composition enriched with full-length mRNA that encodes for arginosuccinate lyase protein. In certain embodiments the present invention provides a method for producing a therapeutic composition enriched with full-length mRNA that encodes for arginase protein.

In certain embodiments the present invention provides a method for producing a therapeutic composition enriched with full-length mRNA that encodes for a protein associated with a lysosomal storage disorder. In certain embodiments the present invention provides a method for producing a therapeutic composition enriched with full-length mRNA that encodes for alpha galactosidase protein. In certain embodiments the present invention provides a method for producing a therapeutic composition enriched with full-length mRNA that encodes for glucocerebrosidase protein. In certain embodiments the present invention provides a method for producing a therapeutic composition enriched with full-length mRNA that encodes for iduronate-2-sulfatase protein. In certain embodiments the present invention provides a method for producing a therapeutic composition enriched with full-length mRNA that encodes for iduronidase protein. In certain embodiments the present invention provides a method for producing a therapeutic composition enriched with full-length mRNA that encodes for N-acetyl-alpha-D-glucosaminidase protein. In certain embodiments the present invention provides a method for producing a therapeutic composition enriched with full-length mRNA that encodes for heparan N-sulfatase protein. In certain embodiments the present invention provides a method for producing a therapeutic composition enriched with full-length mRNA that encodes for galactosamine-6 sulfatase protein. In certain embodiments the present invention provides a method for producing a therapeutic composition enriched with full-length mRNA that encodes for beta-galactosidase protein. In certain embodiments the present invention provides a method for producing a therapeutic composition enriched with full-length mRNA that encodes for lysosomal lipase protein. In certain embodiments the present invention provides a method for producing a therapeutic composition enriched with full-length mRNA that encodes for arylsulfatase B (N-acetylgalactosamine-4-sulfatase) protein. In certain embodiments the present invention provides a method for producing a therapeutic composition enriched with full-length mRNA that encodes for transcription factor EB (TFEB).

In certain embodiments the present invention provides a method for producing a therapeutic composition enriched with full-length mRNA that encodes for a protein associated with a glycogen storage disorder. In certain embodiments the present invention provides a method for producing a therapeutic composition enriched with full-length mRNA that encodes for acid alpha-glucosidase protein. In certain embodiments the present invention provides a method for producing a therapeutic composition enriched with full-length mRNA that encodes for glucose-6-phosphatase (G6PC) protein. In certain embodiments the present invention provides a method for producing a therapeutic composition enriched with full-length mRNA that encodes for liver glycogen phosphorylase protein. In certain embodiments the present invention provides a method for producing a therapeutic composition enriched with full-length mRNA that encodes for muscle phosphoglycerate mutase protein. In certain embodiments the present invention provides a method for producing a therapeutic composition enriched with full-length mRNA that encodes for glycogen debranching enzyme.

In certain embodiments the present invention provides a method for producing a therapeutic composition enriched with full-length mRNA that encodes for a protein associated with amino acid metabolism. In certain embodiments the present invention provides a method for producing a therapeutic composition enriched with full-length mRNA that encodes for phenylalanine hydroxylase enzyme. In certain embodiments the present invention provides a method for producing a therapeutic composition enriched with full-length mRNA that encodes for glutaryl-CoA dehydrogenase enzyme. In certain embodiments the present invention provides a method for producing a therapeutic composition enriched with full-length mRNA that encodes for propionyl-CoA caboxylase enzyme. In certain embodiments the present invention provides a method for producing a therapeutic composition enriched with full-length mRNA that encodes for oxalase alanine-glyoxylate aminotransferase enzyme.

In certain embodiments the present invention provides a method for producing a therapeutic composition enriched with full-length mRNA that encodes for a protein associated with a lipid metabolism or fibrotic disorder. In certain embodiments the present invention provides a method for producing a therapeutic composition enriched with full-length mRNA that encodes for a mTOR inhibitor. In certain embodiments the present invention provides a method for producing a therapeutic composition enriched with full-length mRNA that encodes for ATPase phospholipid transporting 8B1 (ATP8B1) protein. In certain embodiments the present invention provides a method for producing a therapeutic composition enriched with full-length mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition enriched with full-length mRNA that encodes for PPAR-gamma protein or an active variant.

In certain embodiments the present invention provides a method for producing a therapeutic composition enriched with full-length mRNA that encodes for a protein associated with methylmalonic acidemia. For example, in certain embodiments the present invention provides a method for producing a therapeutic composition enriched with full-length mRNA that encodes for methylmalonyl CoA mutase protein. In certain embodiments the present invention provides a method for producing a therapeutic composition enriched with full-length mRNA that encodes for methylmalonyl CoA epimerase protein.

In certain embodiments the present invention provides a method for producing a therapeutic composition enriched with full-length mRNA for which delivery to or treatment of the liver can provide therapeutic benefit. In certain embodiments the present invention provides a method for producing a therapeutic composition enriched with full-length mRNA that encodes for ATP7B protein, also known as Wilson disease protein. In certain embodiments the present invention provides a method for producing a therapeutic composition enriched with full-length mRNA that encodes for porphobilinogen deaminase enzyme. In certain embodiments the present invention provides a method for producing a therapeutic composition enriched with full-length mRNA that encodes for one or clotting enzymes, such as Factor VIII, Factor IX, Factor VII, and Factor X. In certain embodiments the present invention provides a method for producing a therapeutic composition enriched with full-length mRNA that encodes for human hemochromatosis (HFE) protein.

In certain embodiments the present invention provides a method for producing a therapeutic composition enriched with full-length mRNA that encodes a peptide or polypeptide for use in the delivery to or treatment of the cardiovasculature of a subject or a cardiovascular cell. In certain embodiments the present invention provides a method for producing a therapeutic composition enriched with full-length mRNA that encodes for vascular endothelial growth factor A protein. In certain embodiments the present invention provides a method for producing a therapeutic composition enriched with full-length mRNA that encodes for relaxin protein. In certain embodiments the present invention provides a method for producing a therapeutic composition enriched with full-length mRNA that encodes for bone morphogenetic protein-9 protein. In certain embodiments the present invention provides a method for producing a therapeutic composition enriched with full-length mRNA that encodes for bone morphogenetic protein-2 receptor protein.

In certain embodiments the present invention provides a method for producing a therapeutic composition enriched with full-length mRNA that encodes a peptide or polypeptide for use in the delivery to or treatment of the muscle of a subject or a muscle cell. In certain embodiments the present invention provides a method for producing a therapeutic composition enriched with full-length mRNA that encodes for dystrophin protein. In certain embodiments the present invention provides a method for producing a therapeutic composition enriched with full-length mRNA that encodes for frataxin protein. In certain embodiments the present invention provides a method for producing a therapeutic composition enriched with full-length mRNA that encodes a peptide or polypeptide for use in the delivery to or treatment of the cardiac muscle of a subject or a cardiac muscle cell. In certain embodiments the present invention provides a method for producing a therapeutic composition enriched with full-length mRNA that encodes for a protein that modulates one or both of a potassium channel and a sodium channel in muscle tissue or in a muscle cell. In certain embodiments the present invention provides a method for producing a therapeutic composition enriched with full-length mRNA that encodes for a protein that modulates a Kv7.1 channel in muscle tissue or in a muscle cell. In certain embodiments the present invention provides a method for producing a therapeutic composition enriched with full-length mRNA that encodes for a protein that modulates a Nav1.5 channel in muscle tissue or in a muscle cell.

In certain embodiments the present invention provides a method for producing a therapeutic composition enriched with full-length mRNA that encodes a peptide or polypeptide for use in the delivery to or treatment of the nervous system of a subject or a nervous system cell. For example, in certain embodiments the present invention provides a method for producing a therapeutic composition enriched with full-length mRNA that encodes for survival motor neuron 1 protein. For example, in certain embodiments the present invention provides a method for producing a therapeutic composition enriched with full-length mRNA that encodes for survival motor neuron 2 protein. In certain embodiments the present invention provides a method for producing a therapeutic composition enriched with full-length mRNA that encodes for frataxin protein. In certain embodiments the present invention provides a method for producing a therapeutic composition enriched with full-length mRNA that encodes for ATP binding cassette sub-family D member 1 (ABCD1) protein. In certain embodiments the present invention provides a method for producing a therapeutic composition enriched with full-length mRNA that encodes for CLN3 protein.

In certain embodiments the present invention provides a method for producing a therapeutic composition enriched with full-length mRNA that encodes a peptide or polypeptide for use in the delivery to or treatment of the blood or bone marrow of a subject or a blood or bone marrow cell. In certain embodiments the present invention provides a method for producing a therapeutic composition enriched with full-length mRNA that encodes for beta globin protein. In certain embodiments the present invention provides a method for producing a therapeutic composition enriched with full-length mRNA that encodes for Bruton's tyrosine kinase protein. In certain embodiments the present invention provides a method for producing a therapeutic composition enriched with full-length mRNA that encodes for one or clotting enzymes, such as Factor VIII, Factor IX, Factor VII, and Factor X.

In certain embodiments the present invention provides a method for producing a therapeutic composition enriched with full-length mRNA that encodes a peptide or polypeptide for use in the delivery to or treatment of the kidney of a subject or a kidney cell. In certain embodiments the present invention provides a method for producing a therapeutic composition enriched with full-length mRNA that encodes for collagen type IV alpha 5 chain (COL4A5) protein.

In certain embodiments the present invention provides a method for producing a therapeutic composition enriched with full-length mRNA that encodes a peptide or polypeptide for use in the delivery to or treatment of the eye of a subject or an eye cell. In certain embodiments the present invention provides a method for producing a therapeutic composition enriched with full-length mRNA that encodes for ATP-binding cassette sub-family A member 4 (ABCA4) protein. In certain embodiments the present invention provides a method for producing a therapeutic composition enriched with full-length mRNA that encodes for retinoschisin protein. In certain embodiments the present invention provides a method for producing a therapeutic composition enriched with full-length mRNA that encodes for retinal pigment epithelium-specific 65 kDa (RPE65) protein. In certain embodiments the present invention provides a method for producing a therapeutic composition enriched with full-length mRNA that encodes for centrosomal protein of 290 kDa (CEP290).

In certain embodiments the present invention provides a method for producing a therapeutic composition enriched with full-length mRNA that encodes a peptide or polypeptide for use in the delivery of or treatment with a vaccine for a subject or a cell of a subject. For example, in certain embodiments the present invention provides a method for producing a therapeutic composition enriched with full-length mRNA that encodes for an antigen from an infectious agent, such as a virus. In certain embodiments the present invention provides a method for producing a therapeutic composition enriched with full-length mRNA that encodes for an antigen from influenza virus. In certain embodiments the present invention provides a method for producing a therapeutic composition enriched with full-length mRNA that encodes for an antigen from respiratory syncytial virus. In certain embodiments the present invention provides a method for producing a therapeutic composition enriched with full-length mRNA that encodes for an antigen from rabies virus. In certain embodiments the present invention provides a method for producing a therapeutic composition enriched with full-length mRNA that encodes for an antigen from cytomegalovirus. In certain embodiments the present invention provides a method for producing a therapeutic composition enriched with full-length mRNA that encodes for an antigen from rotavirus. In certain embodiments the present invention provides a method for producing a therapeutic composition enriched with full-length mRNA that encodes for an antigen from a hepatitis virus, such as hepatitis A virus, hepatitis B virus, or hepatis C virus. In certain embodiments the present invention provides a method for producing a therapeutic composition enriched with full-length mRNA that encodes for an antigen from human papillomavirus. In certain embodiments the present invention provides a method for producing a therapeutic composition enriched with full-length mRNA that encodes for an antigen from a herpes simplex virus, such as herpes simplex virus 1 or herpes simplex virus 2. In certain embodiments the present invention provides a method for producing a therapeutic composition enriched with full-length mRNA that encodes for an antigen from a human immunodeficiency virus, such as human immunodeficiency virus type 1 or human immunodeficiency virus type 2. In certain embodiments the present invention provides a method for producing a therapeutic composition enriched with full-length mRNA that encodes for an antigen from a human metapneumovirus. In certain embodiments the present invention provides a method for producing a therapeutic composition enriched with full-length mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition enriched with full-length mRNA that encodes for an antigen from malaria virus. In certain embodiments the present invention provides a method for producing a therapeutic composition enriched with full-length mRNA that encodes for an antigen from zika virus. In certain embodiments the present invention provides a method for producing a therapeutic composition enriched with full-length mRNA that encodes for an antigen from chikungunya virus.

In certain embodiments the present invention provides a method for producing a therapeutic composition enriched with full-length mRNA that encodes for an antigen associated with a cancer of a subject or identified from a cancer cell of a subject. In certain embodiments the present invention provides a method for producing a therapeutic composition enriched with full-length mRNA that encodes for an antigen determined from a subject's own cancer cell, i.e., to provide a personalized cancer vaccine. In certain embodiments the present invention provides a method for producing a therapeutic composition enriched with full-length mRNA that encodes for an antigen expressed from a mutant KRAS gene.

In certain embodiments the present invention provides a method for producing a therapeutic composition enriched with full-length mRNA that encodes for an antibody. In certain embodiments, the antibody can be a bi-specific antibody. In certain embodiments, the antibody can be part of a fusion protein. In certain embodiments the present invention provides a method for producing a therapeutic composition enriched with full-length mRNA that encodes for an antibody to OX40. In certain embodiments the present invention provides a method for producing a therapeutic composition enriched with full-length mRNA that encodes for an antibody to VEGF. In certain embodiments the present invention provides a method for producing a therapeutic composition enriched with full-length mRNA that encodes for an antibody to tissue necrosis factor alpha. In certain embodiments the present invention provides a method for producing a therapeutic composition enriched with full-length mRNA that encodes for an antibody to CD3. In certain embodiments the present invention provides a method for producing a therapeutic composition enriched with full-length mRNA that encodes for an antibody to CD19.

In certain embodiments the present invention provides a method for producing a therapeutic composition enriched with full-length mRNA that encodes for an immunomodulator. In certain embodiments the present invention provides a method for producing a therapeutic composition enriched with full-length mRNA that encodes for Interleukin 12. In certain embodiments the present invention provides a method for producing a therapeutic composition enriched with full-length mRNA that encodes for Interleukin 23. In certain embodiments the present invention provides a method for producing a therapeutic composition enriched with full-length mRNA that encodes for Interleukin 36 gamma. In certain embodiments the present invention provides a method for producing a therapeutic composition enriched with full-length mRNA that encodes for a constitutively active variant of one or more stimulator of interferon genes (STING) proteins.

In certain embodiments the present invention provides a method for producing a therapeutic composition enriched with full-length mRNA that encodes for an endonuclease. In certain embodiments the present invention provides a method for producing a therapeutic composition enriched with full-length mRNA that encodes for an RNA-guided DNA endonuclease protein, such as Cas 9 protein. In certain embodiments the present invention provides a method for producing a therapeutic composition enriched with full-length mRNA that encodes for a meganuclease protein. In certain embodiments the present invention provides a method for producing a therapeutic composition enriched with full-length mRNA that encodes for a transcription activator-like effector nuclease protein. In certain embodiments the present invention provides a method for producing a therapeutic composition enriched with full-length mRNA that encodes for a zinc finger nuclease protein.

In embodiments, exemplary therapeutic uses result from the delivery of mRNA encoding a secreted protein. Accordingly, in embodiments, the compositions and methods of the invention provide for delivery of mRNA encoding a secreted protein. In some embodiments, the compositions and methods of the invention provide for delivery of mRNA encoding one or more secreted proteins listed in Table 1; thus, compositions of the invention may comprise an mRNA encoding a protein listed in Table 1 (or a homolog thereof) along with other components set out herein, and methods of the invention may comprise preparing and/or administering a composition comprising an mRNA encoding a protein listed in Table 1 (or a homolog thereof) along with other components set out herein.

In some embodiments, compositions and methods of the invention provide for the delivery of one or more nucleic acids that bind to or otherwise act on an endogenous nucleic acid, such as endogenous mRNA or DNA, that alter the transcription, translation, secretion, or action of one or more proteins or genes listed in Table 1 (or a homolog thereof). For example, various RNAi nucleic acids bind to endogenous mRNA, miRNA, or other RNAs, while guide RNA (gRNA) and CRISPR RNA (crRNA) respectively bind to DNA and act on DNA in the nucleus. Accordingly, in embodiments, the compositions and methods of the invention provide for delivery of nucleic acids including one or more of RNAi nucleic acids, gRNA and crRNA that interfere with the transcription, translation, secretion, or action of one or more genes or proteins listed in Table 1 (or homologs thereof) along with other components set out herein.

TABLE 1

| Secreted Proteins | | |
|---|---|---|
| Uniprot ID | Protein Name | Gene Name |
| A1E959 | Odontogenic ameloblast-associated protein | ODAM |
| A1KZ92 | Peroxidasin-like protein | PXDNL |
| A1L453 | Serine protease 38 | PRSS38 |
| A1L4H1 | Soluble scavenger receptor cysteine-rich domain-containing protein SSC5D | SSC5D |
| A2RUU4 | Colipase-like protein 1 | CLPSL1 |
| A2VDF0 | Fucose mutarotase | FUOM |
| A2VEC9 | SCO-spondin | SSPO |
| A3KMH1 | von Willebrand factor A domain-containing protein 8 | VWA8 |
| A4D0S4 | Laminin subunit beta-4 | LAMB4 |
| A4D1T9 | Probable inactive serine protease 37 | PRSS37 |
| A5D8T8 | C-type lectin domain family 18 member A | CLEC18A |
| A6NC86 | phospholipase A2 inhibitor and Ly6/PLAUR domain-containing protein | PINLYP |
| A6NCI4 | von Willebrand factor A domain-containing protein 3A | VWA3A |
| A6ND01 | Probable folate receptor delta | FOLR4 |
| A6NDD2 | Beta-defensin 108B-like | |
| A6NE02 | BTB/POZ domain-containing protein 17 | BTBD17 |
| A6NEF6 | Growth hormone 1 | GH1 |
| A6NF02 | NPIP-like protein LOC730153 | |
| A6NFB4 | HCG1749481, isoform CRA_k | CSH1 |
| A6NFZ4 | Protein FAM24A | FAM24A |
| A6NG13 | Glycosyltransferase 54 domain-containing protein | |
| A6NGN9 | IgLON family member 5 | IGLON5 |
| A6NHN0 | Otolin-1 | OTOL1 |
| A6NHN6 | Nuclear pore complex-interacting protein-like 2 | NPIPL2 |
| A6NI73 | Leukocyte immunoglobulin-like receptor subfamily A member 5 | LILRA5 |
| A6NIT4 | Chorionic somatomammotropin hormone 2 isoform 2 | CSH2 |
| A6NJ69 | IgA-inducing protein homolog | IGIP |
| A6NKQ9 | Choriogonadotropin subunit beta variant 1 | CGB1 |
| A6NMZ7 | Collagen alpha-6(VI) chain | COL6A6 |
| A6NNS2 | Dehydrogenase/reductase SDR family member 7C | DHRS7C |
| A6XGL2 | Insulin A chain | INS |
| A8K0G1 | Protein Wnt | WNT7B |
| A8K2U0 | Alpha-2-macroglobulin-like protein 1 | A2ML1 |
| A8K7I4 | Calcium-activated chloride channel regulator 1 | CLCA1 |
| A8MTL9 | Serpin-like protein HMSD | HMSD |
| A8MV23 | Serpin E3 | SERPINE3 |
| A8MZH6 | Oocyte-secreted protein 1 homolog | OOSP1 |
| A8TX70 | Collagen alpha-5(VI) chain | COL6A5 |
| B0ZBE8 | Natriuretic peptide | NPPA |
| B1A4G9 | Somatotropin | GH1 |
| B1A4H2 | HCG1749481, isoform CRA_d | CSH1 |
| B1A4H9 | Chorionic somatomammotropin hormone | CSH2 |
| B1AJZ6 | Protein Wnt | WNT4 |
| B1AKI9 | Isthmin-1 | ISM1 |
| B2RNN3 | Complement C1q and tumor necrosis factor-related protein 9B | C1QTNF9B |
| B2RUY7 | von Willebrand factor C domain-containing protein 2-like | VWC2L |
| B3GLJ2 | Prostate and testis expressed protein 3 | PATE3 |
| B4DI03 | SEC11-like 3 (S. cerevisiae), isoform CRA_a | SEC11L3 |
| B4DJF9 | Protein Wnt | WNT4 |
| B4DUL4 | SEC11-like 1 (S. cerevisiae), isoform CRA_d | SEC11L1 |
| B5MCC8 | Protein Wnt | WNT10B |
| B8A595 | Protein Wnt | WNT7B |
| B8A597 | Protein Wnt | WNT7B |
| B8A598 | Protein Wnt | WNT7B |
| B9A064 | Immunoglobulin lambda-like polypeptide 5 | IGLL5 |
| C9J3H3 | Protein Wnt | WNT10B |
| C9J8I8 | Protein Wnt | WNT5A |
| C9JAF2 | Insulin-like growth factor II Ala-25 Del | IGF2 |
| C9JCI2 | Protein Wnt | WNT10B |
| C9JL84 | HERV-H LTR-associating protein 1 | HHLA1 |
| C9JNR5 | Insulin A chain | INS |
| C9JUI2 | Protein Wnt | WNT2 |
| D6RF47 | Protein Wnt | WNT8A |

TABLE 1-continued

Secreted Proteins

| Uniprot ID | Protein Name | Gene Name |
|---|---|---|
| D6RF94 | Protein Wnt | WNT8A |
| E2RYF7 | Protein PBMUCL2 | HCG22 |
| E5RFR1 | PENK(114-133) | PENK |
| E7EML9 | Serine protease 44 | PRSS44 |
| E7EPC3 | Protein Wnt | WNT9B |
| E7EVP0 | Nociceptin | PNOC |
| E9PD02 | Insulin-like growth factor I | IGF1 |
| E9PH60 | Protein Wnt | WNT16 |
| E9PJL6 | Protein Wnt | WNT11 |
| F5GYM2 | Protein Wnt | WNT5B |
| F5H034 | Protein Wnt | WNT5B |
| F5H364 | Protein Wnt | WNT5B |
| F5H7Q6 | Protein Wnt | WNT5B |
| F8WCM5 | Protein INS-IGF2 | INS-IGF2 |
| F8WDR1 | Protein Wnt | WNT2 |
| H0Y663 | Protein Wnt | WNT4 |
| H0YK72 | Signal peptidase complex catalytic subunit SEC11A | SEC11A |
| H0YK83 | Signal peptidase complex catalytic subunit SEC11A | SEC11A |
| H0YM39 | Chorionic somatomammotropin hormone | CSH2 |
| H0YMT7 | Chorionic somatomammotropin hormone | CSH1 |
| H0YN17 | Chorionic somatomammotropin hormone | CSH2 |
| H0YNA5 | Signal peptidase complex catalytic subunit SEC11A | SEC11A |
| H0YNG3 | Signal peptidase complex catalytic subunit SEC11A | SEC11A |
| H0YNX5 | Signal peptidase complex catalytic subunit SEC11A | SEC11A |
| H7BZB8 | Protein Wnt | WNT10A |
| H9KV56 | Choriogonadotropin subunit beta variant 2 | CGB2 |
| I3L0L8 | Protein Wnt | WNT9B |
| J3KNZ1 | Choriogonadotropin subunit beta variant 1 | CGB1 |
| J3KP00 | Choriogonadotropin subunit beta | CGB7 |
| J3QT02 | Choriogonadotropin subunit beta variant 1 | CGB1 |
| O00175 | C-C motif chemokine 24 | CCL24 |
| O00182 | Galectin-9 | LGALS9 |
| O00187 | Mannan-binding lectin serine protease 2 | MASP2 |
| O00230 | Cortistatin | CORT |
| O00253 | Agouti-related protein | AGRP |
| O00270 | 12-(S)-hydroxy-5,8,10,14-eicosatetraenoic acid receptor | GPR31 |
| O00292 | Left-right determination factor 2 | LEFTY2 |
| O00294 | Tubby-related protein 1 | TULP1 |
| O00295 | Tubby-related protein 2 | TULP2 |
| O00300 | Tumor necrosis factor receptor superfamily member 11B | TNFRSF11B |
| O00339 | Matrilin-2 | MATN2 |
| O00391 | Sulfhydryl oxidase 1 | QSOX1 |
| O00468 | Agrin | AGRN |
| O00515 | Ladinin-1 | LAD1 |
| O00533 | Processed neural cell adhesion molecule L1-like protein | CHL1 |
| O00584 | Ribonuclease T2 | RNASET2 |
| O00585 | C-C motif chemokine 21 | CCL21 |
| O00602 | Ficolin-1 | FCN1 |
| O00622 | Protein CYR61 | CYR61 |
| O00626 | MDC(5-69) | CCL22 |
| O00634 | Netrin-3 | NTN3 |
| O00744 | Protein Wnt-10b | WNT10B |
| O00755 | Protein Wnt-7a | WNT7A |
| O14498 | Immunoglobulin superfamily containing leucine-rich repeat protein | ISLR |
| O14511 | Pro-neuregulin-2, membrane-bound isoform | NRG2 |
| O14594 | Neurocan core protein | NCAN |
| O14625 | C-X-C motif chemokine 11 | CXCL11 |
| O14638 | Ectonucleotide pyrophosphatase/phosphodiesterase family member 3 | ENPP3 |
| O14656 | Torsin-1A | TOR1A |
| O14657 | Torsin-1B | TOR1B |
| O14786 | Neuropilin-1 | NRP1 |
| O14788 | Tumor necrosis factor ligand superfamily member 11, membrane form | TNFSF11 |
| O14791 | Apolipoprotein L1 | APOL1 |
| O14793 | Growth/differentiation factor 8 | MSTN |

TABLE 1-continued

Secreted Proteins

| Uniprot ID | Protein Name | Gene Name |
|---|---|---|
| O14904 | Protein Wnt-9a | WNT9A |
| O14905 | Protein Wnt-9b | WNT9B |
| O14944 | Proepiregulin | EREG |
| O14960 | Leukocyte cell-derived chemotaxin-2 | LECT2 |
| O15018 | Processed PDZ domain-containing protein 2 | PDZD2 |
| O15041 | Semaphorin-3E | SEMA3E |
| O15072 | A disintegrin and metalloproteinase with thrombospondin motifs 3 | ADAMTS3 |
| O15123 | Angiopoietin-2 | ANGPT2 |
| O15130 | Neuropeptide FF | NPFF |
| O15197 | Ephrin type-B receptor 6 | EPHB6 |
| O15204 | ADAM DEC 1 | ADAMDEC1 |
| O15230 | Laminin subunit alpha-5 | LAMA5 |
| O15232 | Matrilin-3 | MATN3 |
| O15240 | Neuroendocrine regulatory peptide-1 | VGF |
| O15263 | Beta-defensin 4A | DEFB4A |
| O15335 | Chondroadherin | CHAD |
| O15393 | Transmembrane protease serine 2 catalytic chain | TMPRSS2 |
| O15444 | C-C motif chemokine 25 | CCL25 |
| O15467 | C-C motif chemokine 16 | CCL16 |
| O15496 | Group 10 secretory phospholipase A2 | PLA2G10 |
| O15520 | Fibroblast growth factor 10 | FGF10 |
| O15537 | Retinoschisin | RS1 |
| O43157 | Plexin-B1 | PLXNB1 |
| O43184 | Disintegrin and metalloproteinase domain-containing protein 12 | ADAM12 |
| O43240 | Kallikrein-10 | KLK10 |
| O43278 | Kunitz-type protease inhibitor 1 | SPINT1 |
| O43320 | Fibroblast growth factor 16 | FGF16 |
| O43323 | Desert hedgehog protein C-product | DHH |
| O43405 | Cochlin | COCH |
| O43508 | Tumor necrosis factor ligand superfamily member 12, membrane form | TNFSF12 |
| O43555 | Progonadoliberin-2 | GNRH2 |
| O43557 | Tumor necrosis factor ligand superfamily member 14, soluble form | TNFSF14 |
| O43692 | Peptidase inhibitor 15 | PI15 |
| O43699 | Sialic acid-binding Ig-like lectin 6 | SIGLEC6 |
| O43820 | Hyaluronidase-3 | HYAL3 |
| O43827 | Angiopoietin-related protein 7 | ANGPTL7 |
| O43852 | Calumenin | CALU |
| O43854 | EGF-like repeat and discoidin I-like domain-containing protein 3 | EDIL3 |
| O43866 | CD5 antigen-like | CD5L |
| O43897 | Tolloid-like protein 1 | TLL1 |
| O43915 | Vascular endothelial growth factor D | FIGF |
| O43927 | C-X-C motif chemokine 13 | CXCL13 |
| O60218 | Aldo-keto reductase family 1 member B10 | AKR1B10 |
| O60235 | Transmembrane protease serine 11D | TMPRSS11D |
| O60258 | Fibroblast growth factor 17 | FGF17 |
| O60259 | Kallikrein-8 | KLK8 |
| O60383 | Growth/differentiation factor 9 | GDF9 |
| O60469 | Down syndrome cell adhesion molecule | DSCAM |
| O60542 | Persephin | PSPN |
| O60565 | Gremlin-1 | GREM1 |
| O60575 | Serine protease inhibitor Kazal-type 4 | SPINK4 |
| O60676 | Cystatin-8 | CST8 |
| O60687 | Sushi repeat-containing protein SRPX2 | SRPX2 |
| O60844 | Zymogen granule membrane protein 16 | ZG16 |
| O60882 | Matrix metalloproteinase-20 | MMP20 |
| O60938 | Keratocan | KERA |
| O75015 | Low affinity immunoglobulin gamma Fc region receptor III-B | FCGR3B |
| O75077 | Disintegrin and metalloproteinase domain-containing protein 23 | ADAM23 |
| O75093 | Slit homolog 1 protein | SLIT1 |
| O75094 | Slit homolog 3 protein | SLIT3 |
| O75095 | Multiple epidermal growth factor-like domains protein 6 | MEGF6 |
| O75173 | A disintegrin and metalloproteinase with thrombospondin motifs 4 | ADAMTS4 |
| O75200 | Nuclear pore complex-interacting protein-like 1 | NPIPL1 |
| O75339 | Cartilage intermediate layer protein 1 C1 | CILP |
| O75354 | Ectonucleoside triphosphate diphosphohydrolase 6 | ENTPD6 |

TABLE 1-continued

Secreted Proteins

| Uniprot ID | Protein Name | Gene Name |
| --- | --- | --- |
| O75386 | Tubby-related protein 3 | TULP3 |
| O75398 | Deformed epidermal autoregulatory factor 1 homolog | DEAF1 |
| O75443 | Alpha-tectorin | TECTA |
| O75445 | Usherin | USH2A |
| O75462 | Cytokine receptor-like factor 1 | CRLF1 |
| O75487 | Glypican-4 | GPC4 |
| O75493 | Carbonic anhydrase-related protein 11 | CA11 |
| O75594 | Peptidoglycan recognition protein 1 | PGLYRP1 |
| O75596 | C-type lectin domain family 3 member A | CLEC3A |
| O75610 | Left-right determination factor 1 | LEFTY1 |
| O75629 | Protein CREG1 | CREG1 |
| O75636 | Ficolin-3 | FCN3 |
| O75711 | Scrapie-responsive protein 1 | SCRG1 |
| O75715 | Epididymal secretory glutathione peroxidase | GPX5 |
| O75718 | Cartilage-associated protein | CRTAP |
| O75829 | Chondrosurfactant protein | LECT1 |
| O75830 | Serpin I2 | SERPINI2 |
| O75882 | Attractin | ATRN |
| O75888 | Tumor necrosis factor ligand superfamily member 13 | TNFSF13 |
| O75900 | Matrix metalloproteinase-23 | MMP23A |
| O75951 | Lysozyme-like protein 6 | LYZL6 |
| O75973 | C1q-related factor | C1QL1 |
| O76038 | Secretagogin | SCGN |
| O76061 | Stanniocalcin-2 | STC2 |
| O76076 | WNT1-inducible-signaling pathway protein 2 | WISP2 |
| O76093 | Fibroblast growth factor 18 | FGF18 |
| O76096 | Cystatin-F | CST7 |
| O94769 | Extracellular matrix protein 2 | ECM2 |
| O94813 | Slit homolog 2 protein C-product | SLIT2 |
| O94907 | Dickkopf-related protein 1 | DKK1 |
| O94919 | Endonuclease domain-containing 1 protein | ENDOD1 |
| O94964 | N-terminal form | SOGA1 |
| O95025 | Semaphorin-3D | SEMA3D |
| O95084 | Serine protease 23 | PRSS23 |
| O95150 | Tumor necrosis factor ligand superfamily member 15 | TNFSF15 |
| O95156 | Neurexophilin-2 | NXPH2 |
| O95157 | Neurexophilin-3 | NXPH3 |
| O95158 | Neurexophilin-4 | NXPH4 |
| O95388 | WNT1-inducible-signaling pathway protein 1 | WISP1 |
| O95389 | WNT1-inducible-signaling pathway protein 3 | WISP3 |
| O95390 | Growth/differentiation factor 11 | GDF11 |
| O95393 | Bone morphogenetic protein 10 | BMP 10 |
| O95399 | Urotensin-2 | UTS2 |
| O95407 | Tumor necrosis factor receptor superfamily member 6B | TNFRSF6B |
| O95428 | Papilin | PAPLN |
| O95445 | Apolipoprotein M | APOM |
| O95450 | A disintegrin and metalloproteinase with thrombospondin motifs 2 | ADAMTS2 |
| O95460 | Matrilin-4 | MATN4 |
| O95467 | LHAL tetrapeptide | GNAS |
| O95631 | Netrin-1 | NTN1 |
| O95633 | Follistatin-related protein 3 | FSTL3 |
| O95711 | Lymphocyte antigen 86 | LY86 |
| O95715 | C-X-C motif chemokine 14 | CXCL14 |
| O95750 | Fibroblast growth factor 19 | FGF19 |
| O95760 | Interleukin-33 | IL33 |
| O95813 | Cerberus | CER1 |
| O95841 | Angiopoietin-related protein 1 | ANGPTL1 |
| O95897 | Noelin-2 | OLFM2 |
| O95925 | Eppin | EPPIN |
| O95965 | Integrin beta-like protein 1 | ITGBL1 |
| O95967 | EGF-containing fibulin-like extracellular matrix protein 2 | EFEMP2 |
| O95968 | Secretoglobin family 1D member 1 | SCGB1D1 |
| O95969 | Secretoglobin family 1D member 2 | SCGB1D2 |
| O95970 | Leucine-rich glioma-inactivated protein 1 | LGI1 |
| O95972 | Bone morphogenetic protein 15 | BMP15 |
| O95994 | Anterior gradient protein 2 homolog | AGR2 |
| O95998 | Interleukin-18-binding protein | IL18BP |
| O96009 | Napsin-A | NAPSA |
| O96014 | Protein Wnt-11 | WNT11 |
| P00450 | Ceruloplasmin | CP |

TABLE 1-continued

Secreted Proteins

| Uniprot ID | Protein Name | Gene Name |
| --- | --- | --- |
| P00451 | Factor VIIIa light chain | F8 |
| P00488 | Coagulation factor XIII A chain | F13A1 |
| P00533 | Epidermal growth factor receptor | EGFR |
| P00709 | Alpha-lactalbumin | LALBA |
| P00734 | Prothrombin | F2 |
| P00738 | Haptoglobin beta chain | HP |
| P00739 | Haptoglobin-related protein | HPR |
| P00740 | Coagulation factor IXa heavy chain | F9 |
| P00742 | Factor X heavy chain | F10 |
| P00746 | Complement factor D | CFD |
| P00747 | Plasmin light chain B | PLG |
| P00748 | Coagulation factor XIIa light chain | F12 |
| P00749 | Urokinase-type plasminogen activator long chain A | PLAU |
| P00750 | Tissue-type plasminogen activator | PLAT |
| P00751 | Complement factor B Ba fragment | CFB |
| P00797 | Renin | REN |
| P00973 | 2'-5'-oligoadenylate synthase 1 | OAS1 |
| P00995 | Pancreatic secretory trypsin inhibitor | SPINK1 |
| P01008 | Antithrombin-III | SERPINC1 |
| P01009 | Alpha-1-antitrypsin | SERPINA1 |
| P01011 | Alpha-1-antichymotrypsin His-Pro-less | SERPINA3 |
| P01019 | Angiotensin-1 | AGT |
| P01023 | Alpha-2-macroglobulin | A2M |
| P01024 | Acylation stimulating protein | C3 |
| P01031 | Complement C5 beta chain | C5 |
| P01033 | Metalloproteinase inhibitor 1 | TIMP1 |
| P01034 | Cystatin-C | CST3 |
| P01036 | Cystatin-S | CST4 |
| P01037 | Cystatin-SN | CST1 |
| P01042 | Kininogen-1 light chain | KNG1 |
| P01127 | Platelet-derived growth factor subunit B | PDGFB |
| P01135 | Transforming growth factor alpha | TGFA |
| P01137 | Transforming growth factor beta-1 | TGFB1 |
| P01138 | Beta-nerve growth factor | NGF |
| P01148 | Gonadoliberin-1 | GNRH1 |
| P01160 | Atrial natriuretic factor | NPPA |
| P01178 | Oxytocin | OXT |
| P01185 | Vasopressin-neurophysin 2-copeptin | AVP |
| P01189 | Corticotropin | POMC |
| P01210 | PENK(237-258) | PENK |
| P01213 | Alpha-neoendorphin | PDYN |
| P01215 | Glycoprotein hormones alpha chain | CGA |
| P01222 | Thyrotropin subunit beta | TSHB |
| P01225 | Follitropin subunit beta | FSHB |
| P01229 | Lutropin subunit beta | LHB |
| P01233 | Choriogonadotropin subunit beta | CGB8 |
| P01236 | Prolactin | PRL |
| P01241 | Somatotropin | GH1 |
| P01242 | Growth hormone variant | GH2 |
| P01243 | Chorionic somatomammotropin hormone | CSH2 |
| P01258 | Katacalcin | CALCA |
| P01266 | Thyroglobulin | TG |
| P01270 | Parathyroid hormone | PTH |
| P01275 | Glucagon | GCG |
| P01282 | Intestinal peptide PHM-27 | VIP |
| P01286 | Somatoliberin | GHRH |
| P01298 | Pancreatic prohormone | PPY |
| P01303 | C-flanking peptide of NPY | NPY |
| P01308 | Insulin | INS |
| P01344 | Insulin-like growth factor II | IGF2 |
| P01350 | Big gastrin | GAST |
| P01374 | Lymphotoxin-alpha | LTA |
| P01375 | C-domain 1 | TNF |
| P01562 | Interferon alpha-1/13 | IFNA1 |
| P01563 | Interferon alpha-2 | IFNA2 |
| P01566 | Interferon alpha-10 | IFNA10 |
| P01567 | Interferon alpha-7 | IFNA7 |
| P01568 | Interferon alpha-21 | IFNA21 |
| P01569 | Interferon alpha-5 | IFNA5 |
| P01570 | Interferon alpha-14 | IFNA14 |
| P01571 | Interferon alpha-17 | IFNA17 |
| P01574 | Interferon beta | IFNB1 |
| P01579 | Interferon gamma | IFNG |
| P01583 | Interleukin-1 alpha | IL1A |
| P01584 | Interleukin-1 beta | IL1B |

TABLE 1-continued

Secreted Proteins

| Uniprot ID | Protein Name | Gene Name |
|---|---|---|
| P01588 | Erythropoietin | EPO |
| P01591 | Immunoglobulin J chain | IGJ |
| P01732 | T-cell surface glycoprotein CD8 alpha chain | CD8A |
| P01833 | Polymeric immunoglobulin receptor | PIGR |
| P01857 | Ig gamma-1 chain C region | IGHG1 |
| P01859 | Ig gamma-2 chain C region | IGHG2 |
| P01860 | Ig gamma-3 chain C region | IGHG3 |
| P01861 | Ig gamma-4 chain C region | IGHG4 |
| P01871 | Ig mu chain C region | IGHM |
| P01880 | Ig delta chain C region | IGHD |
| P02452 | Collagen alpha-1(I) chain | COL1A1 |
| P02458 | Chondrocalcin | COL2A1 |
| P02461 | Collagen alpha-1(III) chain | COL3A1 |
| P02462 | Collagen alpha-1(IV) chain | COL4A1 |
| P02647 | Apolipoprotein A-I | APOA1 |
| P02649 | Apolipoprotein E | APOE |
| P02652 | Apolipoprotein A-II | APOA2 |
| P02654 | Apolipoprotein C-I | APOC1 |
| P02655 | Apolipoprotein C-II | APOC2 |
| P02656 | Apolipoprotein C-III | APOC3 |
| P02671 | Fibrinogen alpha chain | FGA |
| P02675 | Fibrinopeptide B | FGB |
| P02679 | Fibrinogen gamma chain | FGG |
| P02741 | C-reactive protein | CRP |
| P02743 | Serum amyloid P-component(1-203) | APCS |
| P02745 | Complement C1q subcomponent subunit A | C1QA |
| P02746 | Complement C1q subcomponent subunit B | C1QB |
| P02747 | Complement C1q subcomponent subunit C | C1QC |
| P02748 | Complement component C9b | C9 |
| P02749 | Beta-2-glycoprotein 1 | APOH |
| P02750 | Leucine-rich alpha-2-glycoprotein | LRG1 |
| P02751 | Ugl-Y2 | FN1 |
| P02753 | Retinol-binding protein 4 | RBP4 |
| P02760 | Trypstatin | AMBP |
| P02763 | Alpha-1-acid glycoprotein 1 | ORM1 |
| P02765 | Alpha-2-HS-glycoprotein chain A | AHSG |
| P02766 | Transthyretin | TTR |
| P02768 | Serum albumin | ALB |
| P02771 | Alpha-fetoprotein | AFP |
| P02774 | Vitamin D-binding protein | GC |
| P02775 | Connective tissue-activating peptide III | PPBP |
| P02776 | Platelet factor 4 | PF4 |
| P02778 | CXCL10(1-73) | CXCL10 |
| P02786 | Transferrin receptor protein 1 | TFRC |
| P02787 | Serotransferrin | TF |
| P02788 | Lactoferroxin-C | LTF |
| P02790 | Hemopexin | HPX |
| P02808 | Statherin | STATH |
| P02810 | Salivary acidic proline-rich phosphoprotein 1/2 | PRH2 |
| P02812 | Basic salivary proline-rich protein 2 | PRB2 |
| P02814 | Peptide D1A | SMR3B |
| P02818 | Osteocalcin | BGLAP |
| P03950 | Angiogenin | ANG |
| P03951 | Coagulation factor XIa heavy chain | F11 |
| P03952 | Plasma kallikrein | KLKB1 |
| P03956 | 27 kDa interstitial collagenase | MMP1 |
| P03971 | Muellerian-inhibiting factor | AMH |
| P03973 | Antileukoproteinase | SLPI |
| P04003 | C4b-binding protein alpha chain | C4BPA |
| P04004 | Somatomedin-B | VTN |
| P04054 | Phospholipase A2 | PLA2G1B |
| P04085 | Platelet-derived growth factor subunit A | PDGFA |
| P04090 | Relaxin A chain | RLN2 |
| P04114 | Apolipoprotein B-100 | APOB |
| P04118 | Colipase | CLPS |
| P04141 | Granulocyte-macrophage colony-stimulating factor | CSF2 |
| P04155 | Trefoil factor 1 | TFF1 |
| P04180 | Phosphatidylcholine-sterol acyltransferase | LCAT |
| P04196 | Histidine-rich glycoprotein | HRG |
| P04217 | Alpha-1B-glycoprotein | A1BG |
| P04275 | von Willebrand antigen 2 | VWF |
| P04278 | Sex hormone-binding globulin | SHBG |
| P04279 | Alpha-inhibin-31 | SEMG1 |
| P04280 | Basic salivary proline-rich protein 1 | PRB1 |
| P04628 | Proto-oncogene Wnt-1 | WNT1 |

TABLE 1-continued

Secreted Proteins

| Uniprot ID | Protein Name | Gene Name |
|---|---|---|
| P04745 | Alpha-amylase 1 | AMY1A |
| P04746 | Pancreatic alpha-amylase | AMY2A |
| P04808 | Prorelaxin H1 | RLN1 |
| P05000 | Interferon omega-1 | IFNW1 |
| P05013 | Interferon alpha-6 | IFNA6 |
| P05014 | Interferon alpha-4 | IFNA4 |
| P05015 | Interferon alpha-16 | IFNA16 |
| P05019 | Insulin-like growth factor I | IGF1 |
| P05060 | GAWK peptide | CHGB |
| P05090 | Apolipoprotein D | APOD |
| P05109 | Protein S100-A8 | S100A8 |
| P05111 | Inhibin alpha chain | INHA |
| P05112 | Interleukin-4 | IL4 |
| P05113 | Interleukin-5 | IL5 |
| P05120 | Plasminogen activator inhibitor 2 | SERPINB2 |
| P05121 | Plasminogen activator inhibitor 1 | SERPINE1 |
| P05154 | Plasma serine protease inhibitor | SERPINA5 |
| P05155 | Plasma protease C1 inhibitor | SERPING1 |
| P05156 | Complement factor I heavy chain | CFI |
| P05160 | Coagulation factor XIII B chain | F13B |
| P05161 | Ubiquitin-like protein ISG15 | ISG15 |
| P05230 | Fibroblast growth factor 1 | FGF1 |
| P05231 | Interleukin-6 | IL6 |
| P05305 | Big endothelin-1 | EDN1 |
| P05408 | C-terminal peptide | SCG5 |
| P05451 | Lithostathine-1-alpha | REG1A |
| P05452 | Tetranectin | CLEC3B |
| P05543 | Thyroxine-binding globulin | SERPINA7 |
| P05814 | Beta-casein | CSN2 |
| P05997 | Collagen alpha-2(V) chain | COL5A2 |
| P06276 | Cholinesterase | BCHE |
| P06307 | Cholecystokinin-12 | CCK |
| P06396 | Gelsolin | GSN |
| P06681 | Complement C2 | C2 |
| P06702 | Protein S100-A9 | S100A9 |
| P06727 | Apolipoprotein A-IV | APOA4 |
| P06734 | Low affinity immunoglobulin epsilon Fc receptor soluble form | FCER2 |
| P06744 | Glucose-6-phosphate isomerase | GPI |
| P06850 | Corticoliberin | CRH |
| P06858 | Lipoprotein lipase | LPL |
| P06881 | Calcitonin gene-related peptide 1 | CALCA |
| P07093 | Glia-derived nexin | SERPINE2 |
| P07098 | Gastric triacylglycerol lipase | LIPF |
| P07225 | Vitamin K-dependent protein S | PROS1 |
| P07237 | Protein disulfide-isomerase | P4HB |
| P07288 | Prostate-specific antigen | KLK3 |
| P07306 | Asialoglycoprotein receptor 1 | ASGR1 |
| P07355 | Annexin A2 | ANXA2 |
| P07357 | Complement component C8 alpha chain | C8A |
| P07358 | Complement component C8 beta chain | C8B |
| P07360 | Complement component C8 gamma chain | C8G |
| P07477 | Alpha-trypsin chain 2 | PRSS1 |
| P07478 | Trypsin-2 | PRSS2 |
| P07492 | Neuromedin-C | GRP |
| P07498 | Kappa-casein | CSN3 |
| P07585 | Decorin | DCN |
| P07911 | Uromodulin | UMOD |
| P07942 | Laminin subunit beta-1 | LAMB1 |
| P07988 | Pulmonary surfactant-associated protein B | SFTPB |
| P07998 | Ribonuclease pancreatic | RNASE1 |
| P08118 | Beta-microseminoprotein | MSMB |
| P08123 | Collagen alpha-2(I) chain | COL1A2 |
| P08185 | Corticosteroid-binding globulin | SERPINA6 |
| P08217 | Chymotrypsin-like elastase family member 2A | CELA2A |
| P08218 | Chymotrypsin-like elastase family member 2B | CELA2B |
| P08253 | 72 kDa type IV collagenase | MMP2 |
| P08254 | Stromelysin-1 | MMP3 |
| P08294 | Extracellular superoxide dismutase [Cu—Zn] | SOD3 |
| P08476 | Inhibin beta A chain | INHBA |
| P08493 | Matrix Gla protein | MGP |
| P08572 | Collagen alpha-2(IV) chain | COL4A2 |
| P08581 | Hepatocyte growth factor receptor | MET |
| P08603 | Complement factor H | CFH |

TABLE 1-continued

Secreted Proteins

| Uniprot ID | Protein Name | Gene Name |
|---|---|---|
| P08620 | Fibroblast growth factor 4 | FGF4 |
| P08637 | Low affinity immunoglobulin gamma Fc region receptor III-A | FCGR3A |
| P08697 | Alpha-2-antiplasmin | SERPINF2 |
| P08700 | Interleukin-3 | IL3 |
| P08709 | Coagulation factor VII | F7 |
| P08833 | Insulin-like growth factor-binding protein 1 | IGFBP1 |
| P08887 | Interleukin-6 receptor subunit alpha | IL6R |
| P08949 | Neuromedin-B-32 | NMB |
| P08F94 | Fibrocystin | PKHD1 |
| P09038 | Fibroblast growth factor 2 | FGF2 |
| P09228 | Cystatin-SA | CST2 |
| P09237 | Matrilysin | MMP7 |
| P09238 | Stromelysin-2 | MMP10 |
| P09341 | Growth-regulated alpha protein | CXCL1 |
| P09382 | Galectin-1 | LGALS1 |
| P09466 | Glycodelin | PAEP |
| P09486 | SPARC | SPARC |
| P09529 | Inhibin beta B chain | INHBB |
| P09544 | Protein Wnt-2 | WNT2 |
| P09603 | Processed macrophage colony-stimulating factor 1 | CSF1 |
| P09681 | Gastric inhibitory polypeptide | GIP |
| P09683 | Secretin | SCT |
| P09919 | Granulocyte colony-stimulating factor | CSF3 |
| P0C091 | FRAS1-related extracellular matrix protein 3 | FREM3 |
| P0C0L4 | C4d-A | C4A |
| P0C0L5 | Complement C4-B alpha chain | C4B |
| P0C0P6 | Neuropeptide S | NPS |
| P0C7L1 | Serine protease inhibitor Kazal-type 8 | SPINK8 |
| P0C862 | Complement C1q and tumor necrosis factor-related protein 9A | C1QTNF9 |
| P0C8F1 | Prostate and testis expressed protein 4 | PATE4 |
| P0CG01 | Gastrokine-3 | GKN3P |
| P0CG36 | Cryptic family protein 1B | CFC1B |
| P0CG37 | Cryptic protein | CFC1 |
| P0CJ68 | Humanin-like protein 1 | MTRNR2L1 |
| P0CJ69 | Humanin-like protein 2 | MTRNR2L2 |
| P0CJ70 | Humanin-like protein 3 | MTRNR2L3 |
| P0CJ71 | Humanin-like protein 4 | MTRNR2L4 |
| P0CJ72 | Humanin-like protein 5 | MTRNR2L5 |
| P0CJ73 | Humanin-like protein 6 | MTRNR2L6 |
| P0CJ74 | Humanin-like protein 7 | MTRNR2L7 |
| P0CJ75 | Humanin-like protein 8 | MTRNR2L8 |
| P0CJ76 | Humanin-like protein 9 | MTRNR2L9 |
| P0CJ77 | Humanin-like protein 10 | MTRNR2L10 |
| P0DJD7 | Pepsin A-4 | PGA4 |
| P0DJD8 | Pepsin A-3 | PGA3 |
| P0DJD9 | Pepsin A-5 | PGA5 |
| P0DJI8 | Amyloid protein A | SAA1 |
| P0DJI9 | Serum amyloid A-2 protein | SAA2 |
| P10082 | Peptide YY(3-36) | PYY |
| P10092 | Calcitonin gene-related peptide 2 | CALCB |
| P10124 | Serglycin | SRGN |
| P10145 | MDNCF-a | IL8 |
| P10147 | MIP-1-alpha(4-69) | CCL3 |
| P10163 | Peptide P-D | PRB4 |
| P10451 | Osteopontin | SPP1 |
| P10599 | Thioredoxin | TXN |
| P10600 | Transforming growth factor beta-3 | TGFB3 |
| P10643 | Complement component C7 | C7 |
| P10645 | Vasostatin-2 | CHGA |
| P10646 | Tissue factor pathway inhibitor | TFPI |
| P10720 | Platelet factor 4 variant(4-74) | PF4V1 |
| P10745 | Retinol-binding protein 3 | RBP3 |
| P10767 | Fibroblast growth factor 6 | FGF6 |
| P10909 | Clusterin alpha chain | CLU |
| P10912 | Growth hormone receptor | GHR |
| P10915 | Hyaluronan and proteoglycan link protein 1 | HAPLN1 |
| P10966 | T-cell surface glycoprotein CD8 beta chain | CD8B |
| P10997 | Islet amyloid polypeptide | IAPP |
| P11047 | Laminin subunit gamma-1 | LAMC1 |
| P11150 | Hepatic triacylglycerol lipase | LIPC |
| P11226 | Mannose-binding protein C | MBL2 |
| P11464 | Pregnancy-specific beta-1-glycoprotein 1 | PSG1 |
| P11465 | Pregnancy-specific beta-1-glycoprotein 2 | PSG2 |
| P11487 | Fibroblast growth factor 3 | FGF3 |

TABLE 1-continued

Secreted Proteins

| Uniprot ID | Protein Name | Gene Name |
|---|---|---|
| P11597 | Cholesteryl ester transfer protein | CETP |
| P11684 | Uteroglobin | SCGB1A1 |
| P11686 | Pulmonary surfactant-associated protein C | SFTPC |
| P12034 | Fibroblast growth factor 5 | FGF5 |
| P12107 | Collagen alpha-1(XI) chain | COL11A1 |
| P12109 | Collagen alpha-1(VI) chain | COL6A1 |
| P12110 | Collagen alpha-2(VI) chain | COL6A2 |
| P12111 | Collagen alpha-3(VI) chain | COL6A3 |
| P12259 | Coagulation factor V | F5 |
| P12272 | PTHrP[1-36] | PTHLH |
| P12273 | Prolactin-inducible protein | PIP |
| P12544 | Granzyme A | GZMA |
| P12643 | Bone morphogenetic protein 2 | BMP2 |
| P12644 | Bone morphogenetic protein 4 | BMP4 |
| P12645 | Bone morphogenetic protein 3 | BMP3 |
| P12724 | Eosinophil cationic protein | RNASE3 |
| P12821 | Angiotensin-converting enzyme, soluble form | ACE |
| P12838 | Neutrophil defensin 4 | DEFA4 |
| P12872 | Motilin | MLN |
| P13232 | Interleukin-7 | IL7 |
| P13236 | C-C motif chemokine 4 | CCL4 |
| P13284 | Gamma-interferon-inducible lysosomal thiol reductase | IFI30 |
| P13500 | C-C motif chemokine 2 | CCL2 |
| P13501 | C-C motif chemokine 5 | CCL5 |
| P13521 | Secretogranin-2 | SCG2 |
| P13591 | Neural cell adhesion molecule 1 | NCAM1 |
| P13611 | Versican core protein | VCAN |
| P13671 | Complement component C6 | C6 |
| P13688 | Carcinoembryonic antigen-related cell adhesion molecule 1 | CEACAM1 |
| P13725 | Oncostatin-M | OSM |
| P13726 | Tissue factor | F3 |
| P13727 | Eosinophil granule major basic protein | PRG2 |
| P13942 | Collagen alpha-2(XI) chain | COL11A2 |
| P13987 | CD59 glycoprotein | CD59 |
| P14138 | Endothelin-3 | EDN3 |
| P14174 | Macrophage migration inhibitory factor | MIF |
| P14207 | Folate receptor beta | FOLR2 |
| P14222 | Perforin-1 | PRF1 |
| P14543 | Nidogen-1 | NID1 |
| P14555 | Phospholipase A2, membrane associated | PLA2G2A |
| P14625 | Endoplasmin | HSP90B1 |
| P14735 | Insulin-degrading enzyme | IDE |
| P14778 | Interleukin-1 receptor type 1, soluble form | IL1R1 |
| P14780 | 82 kDa matrix metalloproteinase-9 | MMP9 |
| P15018 | Leukemia inhibitory factor | LIF |
| P15085 | Carboxypeptidase A1 | CPA1 |
| P15086 | Carboxypeptidase B | CPB1 |
| P15151 | Poliovirus receptor | PVR |
| P15169 | Carboxypeptidase N catalytic chain | CPN1 |
| P15248 | Interleukin-9 | IL9 |
| P15291 | N-acetyllactosamine synthase | B4GALT1 |
| P15309 | PAPG9 | ACPP |
| P15328 | Folate receptor alpha | FOLR1 |
| P15374 | Ubiquitin carboxyl-terminal hydrolase isozyme L3 | UCHL3 |
| P15502 | Elastin | ELN |
| P15509 | Granulocyte-macrophage colony-stimulating factor receptor subunit alpha | CSF2RA |
| P15515 | Histatin-1 | HTN1 |
| P15516 | His3-(31-51)-peptide | HTN3 |
| P15692 | Vascular endothelial growth factor A | VEGFA |
| P15814 | Immunoglobulin lambda-like polypeptide 1 | IGLL1 |
| P15907 | Beta-galactoside alpha-2,6-sialyltransferase 1 | ST6GAL1 |
| P15941 | Mucin-1 subunit beta | MUC1 |
| P16035 | Metalloproteinase inhibitor 2 | TIMP2 |
| P16112 | Aggrecan core protein 2 | ACAN |
| P16233 | Pancreatic triacylglycerol lipase | PNLIP |
| P16442 | Histo-blood group ABO system transferase | ABO |
| P16471 | Prolactin receptor | PRLR |
| P16562 | Cysteine-rich secretory protein 2 | CRISP2 |
| P16619 | C-C motif chemokine 3-like 1 | CCL3L1 |
| P16860 | BNP(3-29) | NPPB |
| P16870 | Carboxypeptidase E | CPE |
| P16871 | Interleukin-7 receptor subunit alpha | IL7R |
| P17213 | Bactericidal permeability-increasing protein | BPI |

TABLE 1-continued

Secreted Proteins

| Uniprot ID | Protein Name | Gene Name |
| --- | --- | --- |
| P17538 | Chymotrypsinogen B | CTRB1 |
| P17931 | Galectin-3 | LGALS3 |
| P17936 | Insulin-like growth factor-binding protein 3 | IGFBP3 |
| P17948 | Vascular endothelial growth factor receptor 1 | FLT1 |
| P18065 | Insulin-like growth factor-binding protein 2 | IGFBP2 |
| P18075 | Bone morphogenetic protein 7 | BMP7 |
| P18428 | Lipopolysaccharide-binding protein | LBP |
| P18509 | PACAP-related peptide | ADCYAP1 |
| P18510 | Interleukin-1 receptor antagonist protein | IL1RN |
| P18827 | Syndecan-1 | SDC1 |
| P19021 | Peptidylglycine alpha-hydroxylating monooxygenase | PAM |
| P19235 | Erythropoietin receptor | EPOR |
| P19438 | Tumor necrosis factor-binding protein 1 | TNFRSF1A |
| P19652 | Alpha-1-acid glycoprotein 2 | ORM2 |
| P19801 | Amiloride-sensitive amine oxidase [copper-containing] | ABP1 |
| P19823 | Inter-alpha-trypsin inhibitor heavy chain H2 | ITIH2 |
| P19827 | Inter-alpha-trypsin inhibitor heavy chain H1 | ITIH1 |
| P19835 | Bile salt-activated lipase | CEL |
| P19875 | C-X-C motif chemokine 2 | CXCL2 |
| P19876 | C-X-C motif chemokine 3 | CXCL3 |
| P19883 | Follistatin | FST |
| P19957 | Elafin | PI3 |
| P19961 | Alpha-amylase 2B | AMY2B |
| P20061 | Transcobalamin-1 | TCN1 |
| P20062 | Transcobalamin-2 | TCN2 |
| P20142 | Gastricsin | PGC |
| P20155 | Serine protease inhibitor Kazal-type 2 | SPINK2 |
| P20231 | Tryptase beta-2 | TPSB2 |
| P20333 | Tumor necrosis factor receptor superfamily member 1B | TNFRSF1B |
| P20366 | Substance P | TAC1 |
| P20382 | Melanin-concentrating hormone | PMCH |
| P20396 | Thyroliberin | TRH |
| P20742 | Pregnancy zone protein | PZP |
| P20774 | Mimecan | OGN |
| P20783 | Neurotrophin-3 | NTF3 |
| P20800 | Endothelin-2 | EDN2 |
| P20809 | Interleukin-11 | IL11 |
| P20827 | Ephrin-A1 | EFNA1 |
| P20849 | Collagen alpha-1(IX) chain | COL9A1 |
| P20851 | C4b-binding protein beta chain | C4BPB |
| P20908 | Collagen alpha-1(V) chain | COL5A1 |
| P21128 | Poly(U)-specific endoribonuclease | ENDOU |
| P21246 | Pleiotrophin | PTN |
| P21583 | Kit ligand | KITLG |
| P21741 | Midkine | MDK |
| P21754 | Zona pellucida sperm-binding protein 3 | ZP3 |
| P21781 | Fibroblast growth factor 7 | FGF7 |
| P21802 | Fibroblast growth factor receptor 2 | FGFR2 |
| P21810 | Biglycan | BGN |
| P21815 | Bone sialoprotein 2 | IBSP |
| P21860 | Receptor tyrosine-protein kinase erbB-3 | ERBB3 |
| P21941 | Cartilage matrix protein | MATN1 |
| P22003 | Bone morphogenetic protein 5 | BMP5 |
| P22004 | Bone morphogenetic protein 6 | BMP6 |
| P22079 | Lactoperoxidase | LPO |
| P22105 | Tenascin-X | TNXB |
| P22301 | Interleukin-10 | IL10 |
| P22303 | Acetylcholinesterase | ACHE |
| P22352 | Glutathione peroxidase 3 | GPX3 |
| P22362 | C-C motif chemokine 1 | CCL1 |
| P22455 | Fibroblast growth factor receptor 4 | FGFR4 |
| P22466 | Galanin message-associated peptide | GAL |
| P22692 | Insulin-like growth factor-binding protein 4 | IGFBP4 |
| P22749 | Granulysin | GNLY |
| P22792 | Carboxypeptidase N subunit 2 | CPN2 |
| P22891 | Vitamin K-dependent protein Z | PROZ |
| P22894 | Neutrophil collagenase | MMP8 |
| P23142 | Fibulin-1 | FBLN1 |
| P23280 | Carbonic anhydrase 6 | CA6 |
| P23352 | Anosmin-1 | KAL1 |
| P23435 | Cerebellin-1 | CBLN1 |
| P23560 | Brain-derived neurotrophic factor | BDNF |
| P23582 | C-type natriuretic peptide | NPPC |

TABLE 1-continued

Secreted Proteins

| Uniprot ID | Protein Name | Gene Name |
| --- | --- | --- |
| P23946 | Chymase | CMA1 |
| P24043 | Laminin subunit alpha-2 | LAMA2 |
| P24071 | Immunoglobulin alpha Fc receptor | FCAR |
| P24347 | Stromelysin-3 | MMP11 |
| P24387 | Corticotropin-releasing factor-binding protein | CRHBP |
| P24592 | Insulin-like growth factor-binding protein 6 | IGFBP6 |
| P24593 | Insulin-like growth factor-binding protein 5 | IGFBP5 |
| P24821 | Tenascin | TNC |
| P24855 | Deoxyribonuclease-1 | DNASE1 |
| P25067 | Collagen alpha-2(VIII) chain | COL8A2 |
| P25311 | Zinc-alpha-2-glycoprotein | AZGP1 |
| P25391 | Laminin subunit alpha-1 | LAMA1 |
| P25445 | Tumor necrosis factor receptor superfamily member 6 | FAS |
| P25940 | Collagen alpha-3(V) chain | COL5A3 |
| P25942 | Tumor necrosis factor receptor superfamily member 5 | CD40 |
| P26022 | Pentraxin-related protein PTX3 | PTX3 |
| P26927 | Hepatocyte growth factor-like protein beta chain | MST1 |
| P27169 | Serum paraoxonase/arylesterase 1 | PON1 |
| P27352 | Gastric intrinsic factor | GIF |
| P27487 | Dipeptidyl peptidase 4 membrane form | DPP4 |
| P27539 | Embryonic growth/differentiation factor 1 | GDF1 |
| P27658 | Vastatin | COL8A1 |
| P27797 | Calreticulin | CALR |
| P27918 | Properdin | CFP |
| P28039 | Acyloxyacyl hydrolase | AOAH |
| P28300 | Protein-lysine 6-oxidase | LOX |
| P28325 | Cystatin-D | CST5 |
| P28799 | Granulin-1 | GRN |
| P29122 | Proprotein convertase subtilisin/kexin type 6 | PCSK6 |
| P29279 | Connective tissue growth factor | CTGF |
| P29320 | Ephrin type-A receptor 3 | EPHA3 |
| P29400 | Collagen alpha-5(IV) chain | COL4A5 |
| P29459 | Interleukin-12 subunit alpha | IL12A |
| P29460 | Interleukin-12 subunit beta | IL12B |
| P29508 | Serpin B3 | SERPINB3 |
| P29622 | Kallistatin | SERPINA4 |
| P29965 | CD40 ligand, soluble form | CD40LG |
| P30990 | Neurotensin/neuromedin N | NTS |
| P31025 | Lipocalin-1 | LCN1 |
| P31151 | Protein S100-A7 | S100A7 |
| P31371 | Fibroblast growth factor 9 | FGF9 |
| P31431 | Syndecan-4 | SDC4 |
| P31947 | 14-3-3 protein sigma | SFN |
| P32455 | Interferon-induced guanylate-binding protein 1 | GBP1 |
| P32881 | Interferon alpha-8 | IFNA8 |
| P34096 | Ribonuclease 4 | RNASE4 |
| P34130 | Neurotrophin-4 | NTF4 |
| P34820 | Bone morphogenetic protein 8B | BMP8B |
| P35030 | Trypsin-3 | PRSS3 |
| P35052 | Secreted glypican-1 | GPC1 |
| P35070 | Betacellulin | BTC |
| P35225 | Interleukin-13 | IL13 |
| P35247 | Pulmonary surfactant-associated protein D | SFTPD |
| P35318 | ADM | ADM |
| P35542 | Serum amyloid A-4 protein | SAA4 |
| P35555 | Fibrillin-1 | FBN1 |
| P35556 | Fibrillin-2 | FBN2 |
| P35625 | Metalloproteinase inhibitor 3 | TIMP3 |
| P35858 | Insulin-like growth factor-binding protein complex acid labile subunit | IGFALS |
| P35916 | Vascular endothelial growth factor receptor 3 | FLT4 |
| P35968 | Vascular endothelial growth factor receptor 2 | KDR |
| P36222 | Chitinase-3-like protein 1 | CHI3L1 |
| P36952 | Serpin B5 | SERPINB5 |
| P36955 | Pigment epithelium-derived factor | SERPINF1 |
| P36980 | Complement factor H-related protein 2 | CFHR2 |
| P39059 | Collagen alpha-1(XV) chain | COL15A1 |
| P39060 | Collagen alpha-1(XVIII) chain | COL18A1 |
| P39877 | Calcium-dependent phospholipase A2 | PLA2G5 |
| P39900 | Macrophage metalloelastase | MMP12 |
| P39905 | Glial cell line-derived neurotrophic factor | GDNF |
| P40225 | Thrombopoietin | THPO |
| P40967 | M-alpha | PMEL |
| P41159 | Leptin | LEP |

TABLE 1-continued

Secreted Proteins

| Uniprot ID | Protein Name | Gene Name |
| --- | --- | --- |
| P41221 | Protein Wnt-5a | WNT5A |
| P41222 | Prostaglandin-H2 D-isomerase | PTGDS |
| P41271 | Neuroblastoma suppressor of tumorigenicity 1 | NBL1 |
| P41439 | Folate receptor gamma | FOLR3 |
| P42127 | Agouti-signaling protein | ASIP |
| P42702 | Leukemia inhibitory factor receptor | LIFR |
| P42830 | ENA-78(9-78) | CXCL5 |
| P43026 | Growth/differentiation factor 5 | GDF5 |
| P43251 | Biotinidase | BTD |
| P43652 | Afamin | AFM |
| P45452 | Collagenase 3 | MMP13 |
| P47710 | Casoxin-D | CSN1S1 |
| P47929 | Galectin-7 | LGALS7B |
| P47972 | Neuronal pentraxin-2 | NPTX2 |
| P47989 | Xanthine oxidase | XDH |
| P47992 | Lymphotactin | XCL1 |
| P48023 | Tumor necrosis factor ligand superfamily member 6, membrane form | FASLG |
| P48052 | Carboxypeptidase A2 | CPA2 |
| P48061 | Stromal cell-derived factor 1 | CXCL12 |
| P48304 | Lithostathine-1-beta | REG1B |
| P48307 | Tissue factor pathway inhibitor 2 | TFPI2 |
| P48357 | Leptin receptor | LEPR |
| P48594 | Serpin B4 | SERPINB4 |
| P48645 | Neuromedin-U-25 | NMU |
| P48740 | Mannan-binding lectin serine protease 1 | MASP1 |
| P48745 | Protein NOV homolog | NOV |
| P48960 | CD97 antigen subunit beta | CD97 |
| P49223 | Kunitz-type protease inhibitor 3 | SPINT3 |
| P49747 | Cartilage oligomeric matrix protein | COMP |
| P49763 | Placenta growth factor | PGF |
| P49765 | Vascular endothelial growth factor B | VEGFB |
| P49767 | Vascular endothelial growth factor C | VEGFC |
| P49771 | Fms-related tyrosine kinase 3 ligand | FLT3LG |
| P49862 | Kallikrein-7 | KLK7 |
| P49863 | Granzyme K | GZMK |
| P49908 | Selenoprotein P | SEPP1 |
| P49913 | Antibacterial protein FALL-39 | CAMP |
| P50607 | Tubby protein homolog | TUB |
| P51124 | Granzyme M | GZMM |
| P51512 | Matrix metalloproteinase-16 | MMP16 |
| P51654 | Glypican-3 | GPC3 |
| P51671 | Eotaxin | CCL11 |
| P51884 | Lumican | LUM |
| P51888 | Prolargin | PRELP |
| P52798 | Ephrin-A4 | EFNA4 |
| P52823 | Stanniocalcin-1 | STC1 |
| P53420 | Collagen alpha-4(IV) chain | COL4A4 |
| P53621 | Coatomer subunit alpha | COPA |
| P54108 | Cysteine-rich secretory protein 3 | CRISP3 |
| P54315 | Pancreatic lipase-related protein 1 | PNLIPRP1 |
| P54317 | Pancreatic lipase-related protein 2 | PNLIPRP2 |
| P54793 | Arylsulfatase F | ARSF |
| P55000 | Secreted Ly-6/uPAR-related protein 1 | SLURP 1 |
| P55001 | Microfibrillar-associated protein 2 | MFAP2 |
| P55056 | Apolipoprotein C-IV | APOC4 |
| P55058 | Phospholipid transfer protein | PLTP |
| P55075 | Fibroblast growth factor 8 | FGF8 |
| P55081 | Microfibrillar-associated protein 1 | MFAP1 |
| P55083 | Microfibril-associated glycoprotein 4 | MFAP4 |
| P55107 | Bone morphogenetic protein 3B | GDF10 |
| P55145 | Mesencephalic astrocyte-derived neurotrophic factor | MANF |
| P55259 | Pancreatic secretory granule membrane major glycoprotein GP2 | GP2 |
| P55268 | Laminin subunit beta-2 | LAMB2 |
| P55773 | CCL23(30-99) | CCL23 |
| P55774 | C-C motif chemokine 18 | CCL18 |
| P55789 | FAD-linked sulfhydryl oxidase ALR | GFER |
| P56703 | Proto-oncogene Wnt-3 | WNT3 |
| P56704 | Protein Wnt-3a | WNT3A |
| P56705 | Protein Wnt-4 | WNT4 |
| P56706 | Protein Wnt-7b | WNT7B |
| P56730 | Neurotrypsin | PRSS12 |
| P56851 | Epididymal secretory protein E3-beta | EDDM3B |
| P56975 | Neuregulin-3 | NRG3 |

TABLE 1-continued

Secreted Proteins

| Uniprot ID | Protein Name | Gene Name |
| --- | --- | --- |
| P58062 | Serine protease inhibitor Kazal-type 7 | SPINK7 |
| P58215 | Lysyl oxidase homolog 3 | LOXL3 |
| P58294 | Prokineticin-1 | PROK1 |
| P58335 | Anthrax toxin receptor 2 | ANTXR2 |
| P58397 | A disintegrin and metalloproteinase with thrombospondin motifs 12 | ADAMTS12 |
| P58417 | Neurexophilin-1 | NXPH1 |
| P58499 | Protein FAM3B | FAM3B |
| P59510 | A disintegrin and metalloproteinase with thrombospondin motifs 20 | ADAMTS20 |
| P59665 | Neutrophil defensin 1 | DEFA1B |
| P59666 | Neutrophil defensin 3 | DEFA3 |
| P59796 | Glutathione peroxidase 6 | GPX6 |
| P59826 | BPI fold-containing family B member 3 | BPIFB3 |
| P59827 | BPI fold-containing family B member 4 | BPIFB4 |
| P59861 | Beta-defensin 131 | DEFB131 |
| P60022 | Beta-defensin 1 | DEFB1 |
| P60153 | Inactive ribonuclease-like protein 9 | RNASE9 |
| P60827 | Complement C1q tumor necrosis factor-related protein 8 | C1QTNF8 |
| P60852 | Zona pellucida sperm-binding protein 1 | ZP1 |
| P60985 | Keratinocyte differentiation-associated protein | KRTDAP |
| P61109 | Kidney androgen-regulated protein | KAP |
| P61278 | Somatostatin-14 | SST |
| P61366 | Osteocrin | OSTN |
| P61626 | Lysozyme C | LYZ |
| P61769 | Beta-2-microglobulin | B2M |
| P61812 | Transforming growth factor beta-2 | TGFB2 |
| P61916 | Epididymal secretory protein E1 | NPC2 |
| P62502 | Epididymal-specific lipocalin-6 | LCN6 |
| P62937 | Peptidyl-prolyl cis-trans isomerase A | PPIA |
| P67809 | Nuclease-sensitive element-binding protein 1 | YBX1 |
| P67812 | Signal peptidase complex catalytic subunit SEC11A | SEC11A |
| P78310 | Coxsackievirus and adenovirus receptor | CXADR |
| P78333 | Secreted glypican-5 | GPC5 |
| P78380 | Oxidized low-density lipoprotein receptor 1 | OLR1 |
| P78423 | Processed fractalkine | CX3CL1 |
| P78509 | Reelin | RELN |
| P78556 | CCL20(2-70) | CCL20 |
| P80075 | MCP-2(6-76) | CCL8 |
| P80098 | C-C motif chemokine 7 | CCL7 |
| P80108 | Phosphatidylinositol-glycan-specific phospholipase D | GPLD1 |
| P80162 | C-X-C motif chemokine 6 | CXCL6 |
| P80188 | Neutrophil gelatinase-associated lipocalin | LCN2 |
| P80303 | Nucleobindin-2 | NUCB2 |
| P80511 | Calcitermin | S100A12 |
| P81172 | Hepcidin-25 | HAMP |
| P81277 | Prolactin-releasing peptide | PRLH |
| P81534 | Beta-defensin 103 | DEFB103A |
| P81605 | Dermcidin | DCD |
| P82279 | Protein crumbs homolog 1 | CRB1 |
| P82987 | ADAMTS-like protein 3 | ADAMTSL3 |
| P83105 | Serine protease HTRA4 | HTRA4 |
| P83110 | Serine protease HTRA3 | HTRA3 |
| P83859 | Orexigenic neuropeptide QRFP | QRFP |
| P98088 | Mucin-5AC | MUC5AC |
| P98095 | Fibulin-2 | FBLN2 |
| P98160 | Basement membrane-specific heparan sulfate proteoglycan core protein | HSPG2 |
| P98173 | Protein FAM3A | FAM3A |
| Q00604 | Norrin | NDP |
| Q00796 | Sorbitol dehydrogenase | SORD |
| Q00887 | Pregnancy-specific beta-1-glycoprotein 9 | PSG9 |
| Q00888 | Pregnancy-specific beta-1-glycoprotein 4 | PSG4 |
| Q00889 | Pregnancy-specific beta-1-glycoprotein 6 | PSG6 |
| Q01523 | HD5(56-94) | DEFA5 |
| Q01524 | Defensin-6 | DEFA6 |
| Q01955 | Collagen alpha-3(IV) chain | COL4A3 |
| Q02297 | Pro-neuregulin-1, membrane-bound isoform | NRG1 |
| Q02325 | Plasminogen-like protein B | PLGLB1 |
| Q02383 | Semenogelin-2 | SEMG2 |
| Q02388 | Collagen alpha-1(VII) chain | COL7A1 |
| Q02505 | Mucin-3A | MUC3A |
| Q02509 | Otoconin-90 | OC90 |

TABLE 1-continued

Secreted Proteins

| Uniprot ID | Protein Name | Gene Name |
|---|---|---|
| Q02747 | Guanylin | GUCA2A |
| Q02763 | Angiopoietin-1 receptor | TEK |
| Q02817 | Mucin-2 | MUC2 |
| Q02985 | Complement factor H-related protein 3 | CFHR3 |
| Q03167 | Transforming growth factor beta receptor type 3 | TGFBR3 |
| Q03403 | Trefoil factor 2 | TFF2 |
| Q03405 | Urokinase plasminogen activator surface receptor | PLAUR |
| Q03591 | Complement factor H-related protein 1 | CFHR1 |
| Q03692 | Collagen alpha-1(X) chain | COL10A1 |
| Q04118 | Basic salivary proline-rich protein 3 | PRB3 |
| Q04756 | Hepatocyte growth factor activator short chain | HGFAC |
| Q04900 | Sialomucin core protein 24 | CD164 |
| Q05315 | Eosinophil lysophospholipase | CLC |
| Q05707 | Collagen alpha-1 (XIV) chain | COL14A1 |
| Q05996 | Processed zona pellucida sperm-binding protein 2 | ZP2 |
| Q06033 | Inter-alpha-trypsin inhibitor heavy chain H3 | ITIH3 |
| Q06141 | Regenerating islet-derived protein 3-alpha | REG3A |
| Q06828 | Fibromodulin | FMOD |
| Q07092 | Collagen alpha-1(XVI) chain | COL16A1 |
| Q07325 | C-X-C motif chemokine 9 | CXCL9 |
| Q07507 | Dermatopontin | DPT |
| Q075Z2 | Binder of sperm protein homolog 1 | BSPH1 |
| Q07654 | Trefoil factor 3 | TFF3 |
| Q07699 | Sodium channel subunit beta-1 | SCN1B |
| Q08345 | Epithelial discoidin domain-containing receptor 1 | DDR1 |
| Q08380 | Galectin-3-binding protein | LGALS3BP |
| Q08397 | Lysyl oxidase homolog 1 | LOXL1 |
| Q08431 | Lactadherin | MFGE8 |
| Q08629 | Testican-1 | SPOCK1 |
| Q08648 | Sperm-associated antigen 11B | SPAG11B |
| Q08830 | Fibrinogen-like protein 1 | FGL1 |
| Q10471 | Polypeptide N-acetylgalactosaminyltransferase 2 | GALNT2 |
| Q10472 | Polypeptide N-acetylgalactosaminyltransferase 1 | GALNT1 |
| Q11201 | CMP-N-acetylneuraminate-beta-galactosamide-alpha-2,3-sialyltransferase 1 | ST3GAL1 |
| Q11203 | CMP-N-acetylneuraminate-beta-1,4-galactoside alpha-2,3-sialyltransferase | ST3GAL3 |
| Q11206 | CMP-N-acetylneuraminate-beta-galactosamide-alpha-2,3-sialyltransferase 4 | ST3GAL4 |
| Q12794 | Hyaluronidase-1 | HYAL1 |
| Q12805 | EGF-containing fibulin-like extracellular matrix protein 1 | EFEMP1 |
| Q12836 | Zona pellucida sperm-binding protein 4 | ZP4 |
| Q12841 | Follistatin-related protein 1 | FSTL1 |
| Q12904 | Aminoacyl tRNA synthase complex-interacting multifunctional protein 1 | AIMP1 |
| Q13018 | Soluble secretory phospholipase A2 receptor | PLA2R1 |
| Q13072 | B melanoma antigen 1 | BAGE |
| Q13093 | Platelet-activating factor acetylhydrolase | PLA2G7 |
| Q13103 | Secreted phosphoprotein 24 | SPP2 |
| Q13162 | Peroxiredoxin-4 | PRDX4 |
| Q13201 | Platelet glycoprotein Ia* | MMRN1 |
| Q13214 | Semaphorin-3B | SEMA3B |
| Q13219 | Pappalysin-1 | PAPPA |
| Q13231 | Chitotriosidase-1 | CHIT1 |
| Q13253 | Noggin | NOG |
| Q13261 | Interleukin-15 receptor subunit alpha | IL15RA |
| Q13275 | Semaphorin-3F | SEMA3F |
| Q13291 | Signaling lymphocytic activation molecule | SLAMF1 |
| Q13316 | Dentin matrix acidic phosphoprotein 1 | DMP1 |
| Q13361 | Microfibrillar-associated protein 5 | MFAP5 |
| Q13410 | Butyrophilin subfamily 1 member A1 | BTN1A1 |
| Q13421 | Mesothelin, cleaved form | MSLN |
| Q13429 | Insulin-like growth factor I | IGF-I |
| Q13443 | Disintegrin and metalloproteinase domain-containing protein 9 | ADAM9 |
| Q13519 | Neuropeptide 1 | PNOC |
| Q13751 | Laminin subunit beta-3 | LAMB3 |
| Q13753 | Laminin subunit gamma-2 | LAMC2 |
| Q13790 | Apolipoprotein F | APOF |
| Q13822 | Ectonucleotide pyrophosphatase/phosphodiesterase family member 2 | ENPP2 |
| Q14031 | Collagen alpha-6(IV) chain | COL4A6 |
| Q14050 | Collagen alpha-3(IX) chain | COL9A3 |
| Q14055 | Collagen alpha-2(IX) chain | COL9A2 |

TABLE 1-continued

Secreted Proteins

| Uniprot ID | Protein Name | Gene Name |
| --- | --- | --- |
| Q14112 | Nidogen-2 | NID2 |
| Q14114 | Low-density lipoprotein receptor-related protein 8 | LRP8 |
| Q14118 | Dystroglycan | DAG1 |
| Q14314 | Fibroleukin | FGL2 |
| Q14393 | Growth arrest-specific protein 6 | GAS6 |
| Q14406 | Chorionic somatomammotropin hormone-like 1 | CSHL1 |
| Q14507 | Epididymal secretory protein E3-alpha | EDDM3A |
| Q14508 | WAP four-disulfide core domain protein 2 | WFDC2 |
| Q14512 | Fibroblast growth factor-binding protein 1 | FGFBP1 |
| Q14515 | SPARC-like protein 1 | SPARCL1 |
| Q14520 | Hyaluronan-binding protein 2 27 kDa light chain | HABP2 |
| Q14563 | Semaphorin-3A | SEMA3A |
| Q14623 | Indian hedgehog protein | IHH |
| Q14624 | Inter-alpha-trypsin inhibitor heavy chain H4 | ITIH4 |
| Q14667 | UPF0378 protein KIAA0100 | KIAA0100 |
| Q14703 | Membrane-bound transcription factor site-1 protease | MBTPS1 |
| Q14766 | Latent-transforming growth factor beta-binding protein 1 | LTBP1 |
| Q14767 | Latent-transforming growth factor beta-binding protein 2 | LTBP2 |
| Q14773 | Intercellular adhesion molecule 4 | ICAM4 |
| Q14993 | Collagen alpha-1(XIX) chain | COL19A1 |
| Q14CN2 | Calcium-activated chloride channel regulator 4, 110 kDa form | CLCA4 |
| Q15046 | Lysine--tRNA ligase | KARS |
| Q15063 | Periostin | POSTN |
| Q15109 | Advanced glycosylation end product-specific receptor | AGER |
| Q15113 | Procollagen C-endopeptidase enhancer 1 | PCOLCE |
| Q15166 | Serum paraoxonase/lactonase 3 | PON3 |
| Q15195 | Plasminogen-like protein A | PLGLA |
| Q15198 | Platelet-derived growth factor receptor-like protein | PDGFRL |
| Q15223 | Poliovirus receptor-related protein 1 | PVRL1 |
| Q15238 | Pregnancy-specific beta-1-glycoprotein 5 | PSG5 |
| Q15363 | Transmembrane emp24 domain-containing protein 2 | TMED2 |
| Q15375 | Ephrin type-A receptor 7 | EPHA7 |
| Q15389 | Angiopoietin-1 | ANGPT1 |
| Q15465 | Sonic hedgehog protein | SHH |
| Q15485 | Ficolin-2 | FCN2 |
| Q15517 | Corneodesmosin | CDSN |
| Q15582 | Transforming growth factor-beta-induced protein ig-h3 | TGFBI |
| Q15661 | Tryptase alpha/beta-1 | TPSAB1 |
| Q15726 | Metastin | KISS1 |
| Q15782 | Chitinase-3-like protein 2 | CHI3L2 |
| Q15828 | Cystatin-M | CST6 |
| Q15846 | Clusterin-like protein 1 | CLUL1 |
| Q15848 | Adiponectin | ADIPOQ |
| Q16206 | Protein disulfide-thiol oxidoreductase | ENOX2 |
| Q16270 | Insulin-like growth factor-binding protein 7 | IGFBP7 |
| Q16363 | Laminin subunit alpha-4 | LAMA4 |
| Q16378 | Proline-rich protein 4 | PRR4 |
| Q16557 | Pregnancy-specific beta-1-glycoprotein 3 | PSG3 |
| Q16568 | CART(42-89) | CARTPT |
| Q16610 | Extracellular matrix protein 1 | ECM1 |
| Q16619 | Cardiotrophin-1 | CTF1 |
| Q16623 | Syntaxin-1A | STX1A |
| Q16627 | HCC-1(9-74) | CCL14 |
| Q16651 | Prostasin light chain | PRSS8 |
| Q16661 | Guanylate cyclase C-activating peptide 2 | GUCA2B |
| Q16663 | CCL15(29-92) | CCL15 |
| Q16674 | Melanoma-derived growth regulatory protein | MIA |
| Q16769 | Glutaminyl-peptide cyclotransferase | QPCT |
| Q16787 | Laminin subunit alpha-3 | LAMA3 |
| Q16842 | CMP-N-acetylneuraminate-beta-galactosamide-alpha-2,3-sialyltransferase 2 | ST3GAL2 |
| Q17RR3 | Pancreatic lipase-related protein 3 | PNLIPRP3 |
| Q17RW2 | Collagen alpha-1(XXIV) chain | COL24A1 |
| Q17RY6 | Lymphocyte antigen 6K | LY6K |
| Q1L6U9 | Prostate-associated microseminoprotein | MSMP |
| Q1W4C9 | Serine protease inhibitor Kazal-type 13 | SPINK13 |
| Q1ZYL8 | Izumo sperm-egg fusion protein 4 | IZUMO4 |
| Q29960 | HLA class I histocompatibility antigen, Cw-16 alpha chain | HLA-C |
| Q2I0M5 | R-spondin-4 | RSPO4 |

TABLE 1-continued

Secreted Proteins

| Uniprot ID | Protein Name | Gene Name |
|---|---|---|
| Q2L4Q9 | Serine protease 53 | PRSS53 |
| Q2MKA7 | R-spondin-1 | RSPO1 |
| Q2MV58 | Tectonic-1 | TCTN1 |
| Q2TAL6 | Brorin | VWC2 |
| Q2UY09 | Collagen alpha-1(XXVIII) chain | COL28A1 |
| Q2VPA4 | Complement component receptor 1-like protein | CR1L |
| Q2WEN9 | Carcinoembryonic antigen-related cell adhesion molecule 16 | CEACAM16 |
| Q30KP8 | Beta-defensin 136 | DEFB136 |
| Q30KP9 | Beta-defensin 135 | DEFB135 |
| Q30KQ1 | Beta-defensin 133 | DEFB133 |
| Q30KQ2 | Beta-defensin 130 | DEFB130 |
| Q30KQ4 | Beta-defensin 116 | DEFB116 |
| Q30KQ5 | Beta-defensin 115 | DEFB115 |
| Q30KQ6 | Beta-defensin 114 | DEFB114 |
| Q30KQ7 | Beta-defensin 113 | DEFB113 |
| Q30KQ8 | Beta-defensin 112 | DEFB112 |
| Q30KQ9 | Beta-defensin 110 | DEFB110 |
| Q30KR1 | Beta-defensin 109 | DEFB109P1 |
| Q32P28 | Prolyl 3-hydroxylase 1 | LEPRE1 |
| Q3B7J2 | Glucose-fructose oxidoreductase domain-containing protein 2 | GFOD2 |
| Q3SY79 | Protein Wnt | WNT3A |
| Q3T906 | N-acetylglucosamine-1-phosphotransferase subunits alpha/beta | GNPTAB |
| Q495T6 | Membrane metallo-endopeptidase-like 1 | MMEL1 |
| Q49AH0 | Cerebral dopamine neurotrophic factor | CDNF |
| Q4G0G5 | Secretoglobin family 2B member 2 | SCGB2B2 |
| Q4G0M1 | Protein FAM132B | FAM132B |
| Q4LDE5 | Sushi, von Willebrand factor type A, EGF and pentraxin domain-containing protein 1 | SVEP1 |
| Q4QY38 | Beta-defensin 134 | DEFB134 |
| Q4VAJ4 | Protein Wnt | WNT10B |
| Q4W5P6 | Protein TMEM155 | TMEM155 |
| Q4ZHG4 | Fibronectin type III domain-containing protein 1 | FNDC1 |
| Q53H76 | Phospholipase A1 member A | PLA1A |
| Q53RD9 | Fibulin-7 | FBLN7 |
| Q53S33 | BolA-like protein 3 | BOLA3 |
| Q5BLP8 | Neuropeptide-like protein C4orf48 | C4orf48 |
| Q5DT21 | Serine protease inhibitor Kazal-type 9 | SPINK9 |
| Q5EBL8 | PDZ domain-containing protein 11 | PDZD11 |
| Q5FYB0 | Arylsulfatase J | ARSJ |
| Q5FYB1 | Arylsulfatase I | ARSI |
| Q5GAN3 | Ribonuclease-like protein 13 | RNASE13 |
| Q5GAN4 | Ribonuclease-like protein 12 | RNASE12 |
| Q5GAN6 | Ribonuclease-like protein 10 | RNASE10 |
| Q5GFL6 | von Willebrand factor A domain-containing protein 2 | VWA2 |
| Q5H8A3 | Neuromedin-S | NMS |
| Q5H8C1 | FRAS1-related extracellular matrix protein 1 | FREM1 |
| Q5IJ48 | Protein crumbs homolog 2 | CRB2 |
| Q5J5C9 | Beta-defensin 121 | DEFB121 |
| Q5JS37 | NHL repeat-containing protein 3 | NHLRC3 |
| Q5JTB6 | Placenta-specific protein 9 | PLAC9 |
| Q5JU69 | Torsin-2A | TOR2A |
| Q5JXM2 | Methyltransferase-like protein 24 | METTL24 |
| Q5JZY3 | Ephrin type-A receptor 10 | EPHA10 |
| Q5K4E3 | Polyserase-2 | PRSS36 |
| Q5SRR4 | Lymphocyte antigen 6 complex locus protein G5c | LY6G5C |
| Q5T1H1 | Protein eyes shut homolog | EYS |
| Q5T4F7 | Secreted frizzled-related protein 5 | SFRP5 |
| Q5T4W7 | Artemin | ARTN |
| Q5T7M4 | Protein FAM132A | FAM132A |
| Q5TEH8 | Protein Wnt | WNT2B |
| Q5TIE3 | von Willebrand factor A domain-containing protein 5B1 | VWA5B1 |
| Q5UCC4 | ER membrane protein complex subunit 10 | EMC10 |
| Q5VST6 | Abhydrolase domain-containing protein FAM108B1 | FAM108B1 |
| Q5VTL7 | Fibronectin type III domain-containing protein 7 | FNDC7 |
| Q5VUM1 | UPF0369 protein C6orf57 | C6orf57 |
| Q5VV43 | Dyslexia-associated protein KIAA0319 | KIAA0319 |
| Q5VWW1 | Complement C1q-like protein 3 | C1QL3 |
| Q5VXI9 | Lipase member N | LIPN |
| Q5VXJ0 | Lipase member K | LIPK |
| Q5VXM1 | CUB domain-containing protein 2 | CDCP2 |

TABLE 1-continued

Secreted Proteins

| Uniprot ID | Protein Name | Gene Name |
|---|---|---|
| Q5VYX0 | Renalase | RNLS |
| Q5VYY2 | Lipase member M | LIPM |
| Q5W186 | Cystatin-9 | CST9 |
| Q5W5W9 | Regulated endocrine-specific protein 18 | RESP18 |
| Q5XG92 | Carboxylesterase 4A | CES4A |
| Q63HQ2 | Pikachurin | EGFLAM |
| Q641Q3 | Meteorin-like protein | METRNL |
| Q66K79 | Carboxypeptidase Z | CPZ |
| Q685J3 | Mucin-17 | MUC17 |
| Q68BL7 | Olfactomedin-like protein 2A | OLFML2A |
| Q68BL8 | Olfactomedin-like protein 2B | OLFML2B |
| Q68DV7 | E3 ubiquitin-protein ligase RNF43 | RNF43 |
| Q6B9Z1 | Insulin growth factor-like family member 4 | IGFL4 |
| Q6BAA4 | Fc receptor-like B | FCRLB |
| Q6E0U4 | Dermokine | DMKN |
| Q6EMK4 | Vasorin | VASN |
| Q6FHJ7 | Secreted frizzled-related protein 4 | SFRP4 |
| Q6GPI1 | Chymotrypsin B2 chain B | CTRB2 |
| Q6GTS8 | Probable Carboxypeptidase PM20D1 | PM20D1 |
| Q6H9L7 | Isthmin-2 | ISM2 |
| Q6IE36 | Ovostatin homolog 2 | OVOS2 |
| Q6IE37 | Ovostatin homolog 1 | OVOS1 |
| Q6IE38 | Serine protease inhibitor Kazal-type 14 | SPINK14 |
| Q6ISS4 | Leukocyte-associated immunoglobulin-like receptor 2 | LAIR2 |
| Q6JVE5 | Epididymal-specific lipocalin-12 | LCN12 |
| Q6JVE6 | Epididymal-specific lipocalin-10 | LCN10 |
| Q6JVE9 | Epididymal-specific lipocalin-8 | LCN8 |
| Q6KF10 | Growth/differentiation factor 6 | GDF6 |
| Q6MZW2 | Follistatin-related protein 4 | FSTL4 |
| Q6NSX1 | Coiled-coil domain-containing protein 70 | CCDC70 |
| Q6NT32 | Carboxylesterase 5A | CES5A |
| Q6NT52 | Choriogonadotropin subunit beta variant 2 | CGB2 |
| Q6NUI6 | Chondroactherin-like protein | CHADL |
| Q6NUJ1 | Saposin A-like | PSAPL1 |
| Q6P093 | Arylacetamide deacetylase-like 2 | AADACL2 |
| Q6P4A8 | Phospholipase B-like 1 | PLBD1 |
| Q6P5S2 | UPF0762 protein C6orf58 | C6orf58 |
| Q6P988 | Protein notum homolog | NOTUM |
| Q6PCB0 | von Willebrand factor A domain-containing protein 1 | VWA1 |
| Q6PDA7 | Sperm-associated antigen 11A | SPAG11A |
| Q6PEW0 | Inactive serine protease 54 | PRSS54 |
| Q6PEZ8 | Podocan-like protein 1 | PODNL1 |
| Q6PKH6 | Dehydrogenase/reductase SDR family member 4-like 2 | DHRS4L2 |
| Q6Q788 | Apolipoprotein A-V | APOA5 |
| Q6SPF0 | Atherin | SAMD1 |
| Q6UDR6 | Kunitz-type protease inhibitor 4 | SPINT4 |
| Q6URK8 | Testis, prostate and placenta-expressed protein | TEPP |
| Q6UW01 | Cerebellin-3 | CBLN3 |
| Q6UW10 | Surfactant-associated protein 2 | SFTA2 |
| Q6UW15 | Regenerating islet-derived protein 3-gamma | REG3G |
| Q6UW32 | Insulin growth factor-like family member 1 | IGFL1 |
| Q6UW78 | UPF0723 protein C11orf83 | C11orf83 |
| Q6UW88 | Epigen | EPGN |
| Q6UWE3 | Colipase-like protein 2 | CLPSL2 |
| Q6UWF7 | NXPE family member 4 | NXPE4 |
| Q6UWF9 | Protein FAM180A | FAM180A |
| Q6UWM5 | GLIPR1-like protein 1 | GLIPR1L1 |
| Q6UWN8 | Serine protease inhibitor Kazal-type 6 | SPINK6 |
| Q6UWP2 | Dehydrogenase/reductase SDR family member 11 | DHRS11 |
| Q6UWP8 | Suprabasin | SBSN |
| Q6UWQ5 | Lysozyme-like protein 1 | LYZL1 |
| Q6UWQ7 | Insulin growth factor-like family member 2 | IGFL2 |
| Q6UWR7 | Ectonucleotide pyrophosphatase/phosphodiesterase family member 6 soluble form | ENPP6 |
| Q6UWT2 | Adropin | ENHO |
| Q6UWU2 | Beta-galactosidase-1-like protein | GLB1L |
| Q6UWW0 | Lipocalin-15 | LCN15 |
| Q6UWX4 | HHIP-like protein 2 | HHIPL2 |
| Q6UWY0 | Arylsulfatase K | ARSK |
| Q6UWY2 | Serine protease 57 | PRSS57 |
| Q6UWY5 | Olfactomedin-like protein 1 | OLFML1 |
| Q6UX06 | Olfactomedin-4 | OLFM4 |

TABLE 1-continued

Secreted Proteins

| Uniprot ID | Protein Name | Gene Name |
|---|---|---|
| Q6UX07 | Dehydrogenase/reductase SDR family member 13 | DHRS13 |
| Q6UX39 | Amelotin | AMTN |
| Q6UX46 | Protein FAM150B | FAM150B |
| Q6UX73 | UPF0764 protein C16orf89 | C16orf89 |
| Q6UXB0 | Protein FAM131A | FAM131A |
| Q6UXB1 | Insulin growth factor-like family member 3 | IGFL3 |
| Q6UXB2 | VEGF co-regulated chemokine 1 | CXCL17 |
| Q6UXF7 | C-type lectin domain family 18 member B | CLEC18B |
| Q6UXH0 | Hepatocellular carcinoma-associated protein TD26 | C19orf80 |
| Q6UXH1 | Cysteine-rich with EGF-like domain protein 2 | CRELD2 |
| Q6UXH8 | Collagen and calcium-binding EGF domain-containing protein 1 | CCBE1 |
| Q6UXH9 | Inactive serine protease PAMR1 | PAMR1 |
| Q6UXI7 | Vitrin | VIT |
| Q6UXI9 | Nephronectin | NPNT |
| Q6UXN2 | Trem-like transcript 4 protein | TREML4 |
| Q6UXS0 | C-type lectin domain family 19 member A | CLEC19A |
| Q6UXT8 | Protein FAM150A | FAM150A |
| Q6UXT9 | Abhydrolase domain-containing protein 15 | ABHD15 |
| Q6UXV4 | Apolipoprotein O-like | APOOL |
| Q6UXX5 | Inter-alpha-trypsin inhibitor heavy chain H6 | ITIH6 |
| Q6UXX9 | R-spondin-2 | RSPO2 |
| Q6UY14 | ADAMTS-like protein 4 | ADAMTSL4 |
| Q6UY27 | Prostate and testis expressed protein 2 | PATE2 |
| Q6W4X9 | Mucin-6 | MUC6 |
| Q6WN34 | Chordin-like protein 2 | CHRDL2 |
| Q6WRI0 | Immunoglobulin superfamily member 10 | IGSF10 |
| Q6X4U4 | Sclerostin domain-containing protein 1 | SOSTDC1 |
| Q6X784 | Zona pellucida-binding protein 2 | ZPBP2 |
| Q6XE38 | Secretoglobin family 1D member 4 | SCGB1D4 |
| Q6XPR3 | Repetin | RPTN |
| Q6XZB0 | Lipase member I | LIPI |
| Q6ZMM2 | ADAMTS-like protein 5 | ADAMTSL5 |
| Q6ZMP0 | Thrombospondin type-1 domain-containing protein 4 | THSD4 |
| Q6ZNF0 | Iron/zinc purple acid phosphatase-like protein | PAPL |
| Q6ZRI0 | Otogelin | OTOG |
| Q6ZRP7 | Sulfhydryl oxidase 2 | QSOX2 |
| Q6ZWJ8 | Kielin/chordin-like protein | KCP |
| Q75N90 | Fibrillin-3 | FBN3 |
| Q765I0 | Urotensin-2B | UTS2D |
| Q76B58 | Protein FAM5C | FAM5C |
| Q76LX8 | A disintegrin and metalloproteinase with thrombospondin motifs 13 | ADAMTS13 |
| Q76M96 | Coiled-coil domain-containing protein 80 | CCDC80 |
| Q7L1S5 | Carbohydrate sulfotransferase 9 | CHST9 |
| Q7L513 | Fc receptor-like A | FCRLA |
| Q7L8A9 | Vasohibin-1 | VASH1 |
| Q7RTM1 | Otopetrin-1 | OTOP1 |
| Q7RTW8 | Otoancorin | OTOA |
| Q7RTY5 | Serine protease 48 | PRSS48 |
| Q7RTY7 | Ovochymase-1 | OVCH1 |
| Q7RTZ1 | Ovochymase-2 | OVCH2 |
| Q7Z304 | MAM domain-containing protein 2 | MAMDC2 |
| Q7Z3S9 | Notch homolog 2 N-terminal-like protein | NOTCH2NL |
| Q7Z4H4 | Intermedin-short | ADM2 |
| Q7Z4P5 | Growth/differentiation factor 7 | GDF7 |
| Q7Z4R8 | UPF0669 protein C6orf120 | C6orf120 |
| Q7Z4W2 | Lysozyme-like protein 2 | LYZL2 |
| Q7Z5A4 | Serine protease 42 | PRSS42 |
| Q7Z5A7 | Protein FAM19A5 | FAM19A5 |
| Q7Z5A8 | Protein FAM19A3 | FAM19A3 |
| Q7Z5A9 | Protein FAM19A1 | FAM19A1 |
| Q7Z5J1 | Hydroxysteroid 1-beta-dehydrogenase 1-like protein | HSD11B1L |
| Q7Z5L0 | Vitelline membrane outer layer protein 1 homolog | VMO1 |
| Q7Z5L3 | Complement C1q-like protein 2 | C1QL2 |
| Q7Z5L7 | Podocan | PODN |
| Q7Z5P4 | 17-beta-hydroxysteroid dehydrogenase 13 | HSD17B13 |
| Q7Z5P9 | Mucin-19 | MUC19 |
| Q7Z5Y6 | Bone morphogenetic protein 8A | BMP8A |
| Q7Z7B7 | Beta-defensin 132 | DEFB132 |
| Q7Z7B8 | Beta-defensin 128 | DEFB128 |
| Q7Z7C8 | Transcription initiation factor TFIID subunit 8 | TAF8 |
| Q7Z7H5 | Transmembrane emp24 domain-containing protein 4 | TMED4 |
| Q86SG7 | Lysozyme g-like protein 2 | LYG2 |

TABLE 1-continued

Secreted Proteins

| Uniprot ID | Protein Name | Gene Name |
|---|---|---|
| Q86SI9 | Protein CEI | C5orf38 |
| Q86TE4 | Leucine zipper protein 2 | LUZP2 |
| Q86TH1 | ADAMTS-like protein 2 | ADAMTSL2 |
| Q86U17 | Serpin A11 | SERPINA11 |
| Q86UU9 | Endokinin-A | TAC4 |
| Q86UW8 | Hyaluronan and proteoglycan link protein 4 | HAPLN4 |
| Q86UX2 | Inter-alpha-trypsin inhibitor heavy chain H5 | ITIH5 |
| Q86V24 | Adiponectin receptor protein 2 | ADIPOR2 |
| Q86VB7 | Soluble CD 163 | CD163 |
| Q86VR8 | Four-jointed box protein 1 | FJX1 |
| Q86WD7 | Serpin A9 | SERPINA9 |
| Q86WN2 | Interferon epsilon | IFNE |
| Q86WS3 | Placenta-specific 1-like protein | PLAC1L |
| Q86X52 | Chondroitin sulfate synthase 1 | CHSY1 |
| Q86XP6 | Gastrokine-2 | GKN2 |
| Q86XS5 | Angiopoietin-related protein 5 | ANGPTL5 |
| Q86Y27 | B melanoma antigen 5 | BAGE5 |
| Q86Y28 | B melanoma antigen 4 | BAGE4 |
| Q86Y29 | B melanoma antigen 3 | BAGE3 |
| Q86Y30 | B melanoma antigen 2 | BAGE2 |
| Q86Y38 | Xylosyltransferase 1 | XYLT1 |
| Q86Y78 | Ly6/PLAUR domain-containing protein 6 | LYPD6 |
| Q86YD3 | Transmembrane protein 25 | TMEM25 |
| Q86YJ6 | Threonine synthase-like 2 | THNSL2 |
| Q86YW7 | Glycoprotein hormone beta-5 | GPHB5 |
| Q86Z23 | Complement C1q-like protein 4 | C1QL4 |
| Q8IU57 | Interleukin-28 receptor subunit alpha | IL28RA |
| Q8IUA0 | WAP four-disulfide core domain protein 8 | WFDC8 |
| Q8IUB2 | WAP four-disulfide core domain protein 3 | WFDC3 |
| Q8IUB3 | Protein WFDC10B | WFDC10B |
| Q8IUB5 | WAP four-disulfide core domain protein 13 | WFDC13 |
| Q8IUH2 | Protein CREG2 | CREG2 |
| Q8IUK5 | Plexin domain-containing protein 1 | PLXDC1 |
| Q8IUL8 | Cartilage intermediate layer protein 2 C2 | CILP2 |
| Q8IUX7 | Adipocyte enhancer-binding protein 1 | AEBP1 |
| Q8IUX8 | Epidermal growth factor-like protein 6 | EGFL6 |
| Q8IVL8 | Carboxypeptidase O | CPO |
| Q8IVN8 | Somatomedin-B and thrombospondin type-1 domain-containing protein | SBSPON |
| Q8IVW8 | Protein spinster homolog 2 | SPNS2 |
| Q8IW75 | Serpin A12 | SERPINA12 |
| Q8IW92 | Beta-galactosidase-1-like protein 2 | GLB1L2 |
| Q8IWL1 | Pulmonary surfactant-associated protein A2 | SFTPA2 |
| Q8IWL2 | Pulmonary surfactant-associated protein A1 | SFTPA1 |
| Q8IWV2 | Contactin-4 | CNTN4 |
| Q8IWY4 | Signal peptide, CUB and EGF-like domain-containing protein 1 | SCUBE1 |
| Q8IX30 | Signal peptide, CUB and EGF-like domain-containing protein 3 | SCUBE3 |
| Q8IXA5 | Sperm acrosome membrane-associated protein 3, membrane form | SPACA3 |
| Q8IXB1 | DnaJ homolog subfamily C member 10 | DNAJC10 |
| Q8IXL6 | Extracellular serine/threonine protein kinase Fam20C | FAM20C |
| Q8IYD9 | Lung adenoma susceptibility protein 2 | LAS2 |
| Q8IYP2 | Serine protease 58 | PRSS58 |
| Q8IYS5 | Osteoclast-associated immunoglobulin-like receptor | OSCAR |
| Q8IZC6 | Collagen alpha-1(XXVII) chain | COL27A1 |
| Q8IZJ3 | C3 and PZP-like alpha-2-macroglobulin domain-containing protein 8 | CPAMD8 |
| Q8IZN7 | Beta-defensin 107 | DEFB107B |
| Q8N0V4 | Leucine-rich repeat LGI family member 2 | LGI2 |
| Q8N104 | Beta-defensin 106 | DEFB106B |
| Q8N119 | Matrix metalloproteinase-21 | MMP21 |
| Q8N129 | Protein canopy homolog 4 | CNPY4 |
| Q8N135 | Leucine-rich repeat LGI family member 4 | LGI4 |
| Q8N145 | Leucine-rich repeat LGI family member 3 | LGI3 |
| Q8N158 | Glypican-2 | GPC2 |
| Q8N1E2 | Lysozyme g-like protein 1 | LYG1 |
| Q8N2E2 | von Willebrand factor D and EGF domain-containing protein | VWDE |
| Q8N2E6 | Prosalusin | TOR2A |
| Q8N2S1 | Latent-transforming growth factor beta-binding protein 4 | LTBP4 |
| Q8N302 | Angiogenic factor with G patch and FHA domains 1 | AGGF1 |

TABLE 1-continued

Secreted Proteins

| Uniprot ID | Protein Name | Gene Name |
|---|---|---|
| Q8N307 | Mucin-20 | MUC20 |
| Q8N323 | NXPE family member 1 | NXPE1 |
| Q8N387 | Mucin-15 | MUC15 |
| Q8N3Z0 | Inactive serine protease 35 | PRSS35 |
| Q8N436 | Inactive carboxypeptidase-like protein X2 | CPXM2 |
| Q8N474 | Secreted frizzled-related protein 1 | SFRP1 |
| Q8N475 | Follistatin-related protein 5 | FSTL5 |
| Q8N4F0 | BPI fold-containing family B member 2 | BPIFB2 |
| Q8N4T0 | Carboxypeptidase A6 | CPA6 |
| Q8N5W8 | Protein FAM24B | FAM24B |
| Q8N687 | Beta-defensin 125 | DEFB125 |
| Q8N688 | Beta-defensin 123 | DEFB123 |
| Q8N690 | Beta-defensin 119 | DEFB119 |
| Q8N6C5 | Immunoglobulin superfamily member 1 | IGSF1 |
| Q8N6C8 | Leukocyte immunoglobulin-like receptor subfamily A member 3 | LILRA3 |
| Q8N6G6 | ADAMTS-like protein 1 | ADAMTSL1 |
| Q8N6Y2 | Leucine-rich repeat-containing protein 17 | LRRC17 |
| Q8N729 | Neuropeptide W-23 | NPW |
| Q8N8U9 | BMP-binding endothelial regulator protein | BMPER |
| Q8N907 | DAN domain family member 5 | DAND5 |
| Q8NAT1 | Glycosyltransferase-like domain-containing protein 2 | GTDC2 |
| Q8NAU1 | Fibronectin type III domain-containing protein 5 | FNDC5 |
| Q8NB37 | Parkinson disease 7 domain-containing protein 1 | PDDC1 |
| Q8NBI3 | Draxin | DRAXIN |
| Q8NBM8 | Prenylcysteine oxidase-like | PCYOX1L |
| Q8NBP7 | Proprotein convertase subtilisin/kexin type 9 | PCSK9 |
| Q8NBQ5 | Estradiol 17-beta-dehydrogenase 11 | HSD17B11 |
| Q8NBV8 | Synaptotagmin-8 | SYT8 |
| Q8NCC3 | Group XV phospholipase A2 | PLA2G15 |
| Q8NCF0 | C-type lectin domain family 18 member C | CLEC18C |
| Q8NCW5 | NAD(P)H-hydrate epimerase | APOA1BP |
| Q8NDA2 | Hemicentin-2 | HMCN2 |
| Q8NDX9 | Lymphocyte antigen 6 complex locus protein G5b | LY6G5B |
| Q8NDZ4 | Deleted in autism protein 1 | C3orf58 |
| Q8NEB7 | Acrosin-binding protein | ACRBP |
| Q8NES8 | Beta-defensin 124 | DEFB124 |
| Q8NET1 | Beta-defensin 108B | DEFB108B |
| Q8NEX5 | Protein WFDC9 | WFDC9 |
| Q8NEX6 | Protein WFDC11 | WFDC11 |
| Q8NF86 | Serine protease 33 | PRSS33 |
| Q8NFM7 | Interleukin-17 receptor D | IL17RD |
| Q8NFQ5 | BPI fold-containing family B member 6 | BPIFB6 |
| Q8NFQ6 | BPI fold-containing family C protein | BPIFC |
| Q8NFU4 | Follicular dendritic cell secreted peptide | FDCSP |
| Q8NFW1 | Collagen alpha-1(XXII) chain | COL22A1 |
| Q8NG35 | Beta-defensin 105 | DEFB105B |
| Q8NG41 | Neuropeptide B-23 | NPB |
| Q8NHW6 | Otospiralin | OTOS |
| Q8NI99 | Angiopoietin-related protein 6 | ANGPTL6 |
| Q8TAA1 | Probable ribonuclease 11 | RNASE11 |
| Q8TAG5 | V-set and transmembrane domain-containing protein 2A | VSTM2A |
| Q8TAL6 | Fin bud initiation factor homolog | FIBIN |
| Q8TAT2 | Fibroblast growth factor-binding protein 3 | FGFBP3 |
| Q8TAX7 | Mucin-7 | MUC7 |
| Q8TB22 | Spermatogenesis-associated protein 20 | SPATA20 |
| Q8TB73 | Protein NDNF | NDNF |
| Q8TB96 | T-cell immunomodulatory protein | ITFG1 |
| Q8TC92 | Protein disulfide-thiol oxidoreductase | ENOX1 |
| Q8TCV5 | WAP four-disulfide core domain protein 5 | WFDC5 |
| Q8TD06 | Anterior gradient protein 3 homolog | AGR3 |
| Q8TD33 | Secretoglobin family 1C member 1 | SCGB1C1 |
| Q8TD46 | Cell surface glycoprotein CD200 receptor 1 | CD200R1 |
| Q8TDE3 | Ribonuclease 8 | RNASE8 |
| Q8TDF5 | Neuropilin and tolloid-like protein 1 | NETO1 |
| Q8TDL5 | BPI fold-containing family B member 1 | BPIFB1 |
| Q8TE56 | A disintegrin and metalloproteinase with thrombospondin motifs 17 | ADAMTS17 |
| Q8TE57 | A disintegrin and metalloproteinase with thrombospondin motifs 16 | ADAMTS16 |
| Q8TE58 | A disintegrin and metalloproteinase with thrombospondin motifs 15 | ADAMTS15 |
| Q8TE59 | A disintegrin and metalloproteinase with thrombospondin motifs 19 | ADAMTS19 |

TABLE 1-continued

Secreted Proteins

| Uniprot ID | Protein Name | Gene Name |
|---|---|---|
| Q8TE60 | A disintegrin and metalloproteinase with thrombospondin motifs 18 | ADAMTS18 |
| Q8TE99 | Acid phosphatase-like protein 2 | ACPL2 |
| Q8TER0 | Sushi, nidogen and EGF-like domain-containing protein 1 | SNED1 |
| Q8TEU8 | WAP, kazal, immunoglobulin, kunitz and NTR domain-containing protein 2 | WFIKKN2 |
| Q8WTQ1 | Beta-defensin 104 | DEFB104B |
| Q8WTR8 | Netrin-5 | NTN5 |
| Q8WTU2 | Scavenger receptor cysteine-rich domain-containing group B protein | SRCRB4D |
| Q8WU66 | Protein TSPEAR | TSPEAR |
| Q8WUA8 | Tsukushin | TSKU |
| Q8WUF8 | Protein FAM172A | FAM172A |
| Q8WUJ1 | Neuferricin | CYB5D2 |
| Q8WUY1 | UPF0670 protein THEM6 | THEM6 |
| Q8WVN6 | Secreted and transmembrane protein 1 | SECTM1 |
| Q8WVQ1 | Soluble calcium-activated nucleotidase 1 | CANT1 |
| Q8WWA0 | Intelectin-1 | ITLN1 |
| Q8WWG1 | Neuregulin-4 | NRG4 |
| Q8WWQ2 | Inactive heparanase-2 | HPSE2 |
| Q8WWU7 | Intelectin-2 | ITLN2 |
| Q8WWY7 | WAP four-disulfide core domain protein 12 | WFDC12 |
| Q8WWY8 | Lipase member H | LIPH |
| Q8WWZ8 | Oncoprotein-induced transcript 3 protein | OIT3 |
| Q8WX39 | Epididymal-specific lipocalin-9 | LCN9 |
| Q8WXA2 | Prostate and testis expressed protein 1 | PATE1 |
| Q8WXD2 | Secretogranin-3 | SCG3 |
| Q8WXF3 | Relaxin-3 A chain | RLN3 |
| Q8WXI7 | Mucin-16 | MUC16 |
| Q8WXQ8 | Carboxypeptidase A5 | CPA5 |
| Q8WXS8 | A disintegrin and metalloproteinase with thrombospondin motifs 14 | ADAMTS14 |
| Q92484 | Acid sphingomyelinase-like phosphodiesterase 3a | SMPDL3A |
| Q92485 | Acid sphingomyelinase-like phosphodiesterase 3b | SMPDL3B |
| Q92496 | Complement factor H-related protein 4 | CFHR4 |
| Q92520 | Protein FAM3C | FAM3C |
| Q92563 | Testican-2 | SPOCK2 |
| Q92583 | C-C motif chemokine 17 | CCL17 |
| Q92626 | Peroxidasin homolog | PXDN |
| Q92743 | Serine protease HTRA1 | HTRA1 |
| Q92752 | Tenascin-R | TNR |
| Q92765 | Secreted frizzled-related protein 3 | FRZB |
| Q92819 | Hyaluronan synthase 2 | HAS2 |
| Q92820 | Gamma-glutamyl hydrolase | GGH |
| Q92824 | Proprotein convertase subtilisin/kexin type 5 | PCSK5 |
| Q92832 | Protein kinase C-binding protein NELL1 | NELL1 |
| Q92838 | Ectodysplasin-A, membrane form | EDA |
| Q92874 | Deoxyribonuclease-1-like 2 | DNASE1L2 |
| Q92876 | Kallikrein-6 | KLK6 |
| Q92913 | Fibroblast growth factor 13 | FGF13 |
| Q92954 | Proteoglycan 4 C-terminal part | PRG4 |
| Q93038 | Tumor necrosis factor receptor superfamily member 25 | TNFRSF25 |
| Q93091 | Ribonuclease K6 | RNASE6 |
| Q93097 | Protein Wnt-2b | WNT2B |
| Q93098 | Protein Wnt-8b | WNT8B |
| Q95460 | Major histocompatibility complex class I-related gene protein | MR1 |
| Q969D9 | Thymic stromal lymphopoietin | TSLP |
| Q969E1 | Liver-expressed antimicrobial peptide 2 | LEAP2 |
| Q969H8 | UPF0556 protein C19orf10 | C19orf10 |
| Q969Y0 | NXPE family member 3 | NXPE3 |
| Q96A54 | Adiponectin receptor protein 1 | ADIPOR1 |
| Q96A83 | Collagen alpha-1(XXVI) chain | EMID2 |
| Q96A84 | EMI domain-containing protein 1 | EMID1 |
| Q96A98 | Tuberoinfundibular peptide of 39 residues | PTH2 |
| Q96A99 | Pentraxin-4 | PTX4 |
| Q96BH3 | Epididymal sperm-binding protein 1 | ELSPBP1 |
| Q96BQ1 | Protein FAM3D | FAM3D |
| Q96CG8 | Collagen triple helix repeat-containing protein 1 | CTHRC1 |
| Q96DA0 | Zymogen granule protein 16 homolog B | ZG16B |
| Q96DN2 | von Willebrand factor C and EGF domain-containing protein | VWCE |
| Q96DR5 | BPI fold-containing family A member 2 | BPIFA2 |
| Q96DR8 | Mucin-like protein 1 | MUCL1 |

TABLE 1-continued

Secreted Proteins

| Uniprot ID | Protein Name | Gene Name |
|---|---|---|
| Q96DX4 | RING finger and SPRY domain-containing protein 1 | RSPRY1 |
| Q96EE4 | Coiled-coil domain-containing protein 126 | CCDC126 |
| Q96GS6 | Abhydrolase domain-containing protein FAM108A1 | FAM108A1 |
| Q96GW7 | Brevican core protein | BCAN |
| Q96HF1 | Secreted frizzled-related protein 2 | SFRP2 |
| Q96I82 | Kazal-type serine protease inhibitor domain-containing protein 1 | KAZALD1 |
| Q96ID5 | Immunoglobulin superfamily member 21 | IGSF21 |
| Q96II8 | Leucine-rich repeat and calponin homology domain-containing protein 3 | LRCH3 |
| Q96IY4 | Carboxypeptidase B2 | CPB2 |
| Q96JB6 | Lysyl oxidase homolog 4 | LOXL4 |
| Q96JK4 | HHIP-like protein 1 | HHIPL1 |
| Q96KN2 | Beta-Ala-His dipeptidase | CNDP1 |
| Q96KW9 | Protein SPACA7 | SPACA7 |
| Q96KX0 | Lysozyme-like protein 4 | LYZL4 |
| Q96L15 | Ecto-ADP-ribosyltransferase 5 | ART5 |
| Q96LB8 | Peptidoglycan recognition protein 4 | PGLYRP4 |
| Q96LB9 | Peptidoglycan recognition protein 3 | PGLYRP3 |
| Q96LC7 | Sialic acid-binding Ig-like lectin 10 | SIGLEC10 |
| Q96LR4 | Protein FAM19A4 | FAM19A4 |
| Q96MK3 | Protein FAM20A | FAM20A |
| Q96MS3 | Glycosyltransferase 1 domain-containing protein 1 | GLT1D1 |
| Q96NY8 | Processed poliovirus receptor-related protein 4 | PVRL4 |
| Q96NZ8 | WAP, kazal, immunoglobulin, kunitz and NTR domain-containing protein 1 | WFIKKN1 |
| Q96NZ9 | Proline-rich acidic protein 1 | PRAP1 |
| Q96P44 | Collagen alpha-1(XXI) chain | COL21A1 |
| Q96PB7 | Noelin-3 | OLFM3 |
| Q96PC5 | Melanoma inhibitory activity protein 2 | MIA2 |
| Q96PD5 | N-acetylmuramoyl-L-alanine amidase | PGLYRP2 |
| Q96PH6 | Beta-defensin 118 | DEFB118 |
| Q96PL1 | Secretoglobin family 3A member 2 | SCGB3A2 |
| Q96PL2 | Beta-tectorin | TECTB |
| Q96QH8 | Sperm acrosome-associated protein 5 | SPACA5 |
| Q96QR1 | Secretoglobin family 3A member 1 | SCGB3A1 |
| Q96QU1 | Protocadherin-15 | PCDH15 |
| Q96QV1 | Hedgehog-interacting protein | HHIP |
| Q96RW7 | Hemicentin-1 | HMCN1 |
| Q96S42 | Nodal homolog | NODAL |
| Q96S86 | Hyaluronan and proteoglycan link protein 3 | HAPLN3 |
| Q96SL4 | Glutathione peroxidase 7 | GPX7 |
| Q96SM3 | Probable carboxypeptidase X1 | CPXM1 |
| Q96T91 | Glycoprotein hormone alpha-2 | GPHA2 |
| Q99062 | Granulocyte colony-stimulating factor receptor | CSF3R |
| Q99102 | Mucin-4 alpha chain | MUC4 |
| Q99217 | Amelogenin, X isoform | AMELX |
| Q99218 | Amelogenin, Y isoform | AMELY |
| Q99435 | Protein kinase C-binding protein NELL2 | NELL2 |
| Q99470 | Stromal cell-derived factor 2 | SDF2 |
| Q99542 | Matrix metalloproteinase-19 | MMP19 |
| Q99574 | Neuroserpin | SERPINI1 |
| Q99584 | Protein S100-A13 | S100A13 |
| Q99616 | C-C motif chemokine 13 | CCL13 |
| Q99645 | Epiphycan | EPYC |
| Q99674 | Cell growth regulator with EF hand domain protein 1 | CGREF1 |
| Q99715 | Collagen alpha-1(XII) chain | COL12A1 |
| Q99727 | Metalloproteinase inhibitor 4 | TIMP4 |
| Q99731 | C-C motif chemokine 19 | CCL19 |
| Q99748 | Neurturin | NRTN |
| Q99935 | Proline-rich protein 1 | PROL1 |
| Q99942 | E3 ubiquitin-protein ligase RNF5 | RNF5 |
| Q99944 | Epidermal growth factor-like protein 8 | EGFL8 |
| Q99954 | Submaxillary gland androgen-regulated protein 3A | SMR3A |
| Q99969 | Retinoic acid receptor responder protein 2 | RARRES2 |
| Q99972 | Myocilin | MYOC |
| Q99983 | Osteomodulin | OMD |
| Q99985 | Semaphorin-3C | SEMA3C |
| Q99988 | Growth/differentiation factor 15 | GDF15 |
| Q9BPW4 | Apolipoprotein L4 | APOL4 |
| Q9BQ08 | Resistin-like beta | RETNLB |
| Q9BQ16 | Testican-3 | SPOCK3 |
| Q9BQ51 | Programmed cell death 1 ligand 2 | PDCD1LG2 |
| Q9BQB4 | Sclerostin | SOST |

TABLE 1-continued

Secreted Proteins

| Uniprot ID | Protein Name | Gene Name |
| --- | --- | --- |
| Q9BQI4 | Coiled-coil domain-containing protein 3 | CCDC3 |
| Q9BQP9 | BPI fold-containing family A member 3 | BPIFA3 |
| Q9BQR3 | Serine protease 27 | PRSS27 |
| Q9BQY6 | WAP four-disulfide core domain protein 6 | WFDC6 |
| Q9BRR6 | ADP-dependent glucokinase | ADPGK |
| Q9BS86 | Zona pellucida-binding protein 1 | ZPBP |
| Q9BSG0 | Protease-associated domain-containing protein 1 | PRADC1 |
| Q9BSG5 | Retbindin | RTBDN |
| Q9BT30 | Probable alpha-ketoglutarate-dependent dioxygenase ABH7 | ALKBH7 |
| Q9BT56 | Spexin | C12orG9 |
| Q9BT67 | NEDD4 family-interacting protein 1 | NDFIP1 |
| Q9BTY2 | Plasma alpha-L-fucosidase | FUCA2 |
| Q9BU40 | Chordin-like protein 1 | CHRDL1 |
| Q9BUD6 | Spondin-2 | SPON2 |
| Q9BUN1 | Protein MENT | MENT |
| Q9BUR5 | Apolipoprotein O | APOO |
| Q9BV94 | ER degradation-enhancing alpha-mannosidase-like 2 | EDEM2 |
| Q9BWP8 | Collectin-11 | COLEC11 |
| Q9BWS9 | Chitinase domain-containing protein 1 | CHID1 |
| Q9BX67 | Junctional adhesion molecule C | JAM3 |
| Q9BX93 | Group XIIB secretory phospholipase A2-like protein | PLA2G12B |
| Q9BXI9 | Complement C1q tumor necrosis factor-related protein 6 | C1QTNF6 |
| Q9BXJ0 | Complement C1q tumor necrosis factor-related protein 5 | C1QTNF5 |
| Q9BXJ1 | Complement C1q tumor necrosis factor-related protein 1 | C1QTNF1 |
| Q9BXJ2 | Complement C1q tumor necrosis factor-related protein 7 | C1QTNF7 |
| Q9BXJ3 | Complement C1q tumor necrosis factor-related protein 4 | C1QTNF4 |
| Q9BXJ4 | Complement C1q tumor necrosis factor-related protein 3 | C1QTNF3 |
| Q9BXJ5 | Complement C1q tumor necrosis factor-related protein 2 | C1QTNF2 |
| Q9BXN1 | Asporin | ASPN |
| Q9BXP8 | Pappalysin-2 | PAPPA2 |
| Q9BXR6 | Complement factor H-related protein 5 | CFHR5 |
| Q9BXS0 | Collagen alpha-1(XXV) chain | COL25A1 |
| Q9BXX0 | EMILIN-2 | EMILIN2 |
| Q9BXY4 | R-spondin-3 | RSPO3 |
| Q9BY15 | EGF-like module-containing mucin-like hormone receptor-like 3 subunit beta | EMR3 |
| Q9BY50 | Signal peptidase complex catalytic subunit SEC11C | SEC11C |
| Q9BY76 | Angiopoietin-related protein 4 | ANGPTL4 |
| Q9BYF1 | Processed angiotensin-converting enzyme 2 | ACE2 |
| Q9BYJ0 | Fibroblast growth factor-binding protein 2 | FGFBP2 |
| Q9BYW3 | Beta-defensin 126 | DEFB126 |
| Q9BYX4 | Interferon-induced helicase C domain-containing protein 1 | IFIH1 |
| Q9BYZ8 | Regenerating islet-derived protein 4 | REG4 |
| Q9BZ76 | Contactin-associated protein-like 3 | CNTNAP3 |
| Q9BZG9 | Ly-6/neurotoxin-like protein 1 | LYNX1 |
| Q9BZJ3 | Tryptase delta | TPSD1 |
| Q9BZM1 | Group XIIA secretory phospholipase A2 | PLA2G12A |
| Q9BZM2 | Group IIF secretory phospholipase A2 | PLA2G2F |
| Q9BZM5 | NKG2D ligand 2 | ULBP2 |
| Q9BZP6 | Acidic mammalian chitinase | CHIA |
| Q9BZZ2 | Sialoadhesin | SIGLEC1 |
| Q9C0B6 | Protein FAM5B | FAM5B |
| Q9GZM7 | Tubulointerstitial nephritis antigen-like | TINAGL1 |
| Q9GZN4 | Brain-specific serine protease 4 | PRSS22 |
| Q9GZP0 | Platelet-derived growth factor D, receptor-binding form | PDGFD |
| Q9GZT5 | Protein Wnt-10a | WNT10A |
| Q9GZU5 | Nyctalopin | NYX |
| Q9GZV7 | Hyaluronan and proteoglycan link protein 2 | HAPLN2 |
| Q9GZV9 | Fibroblast growth factor 23 | FGF23 |
| Q9GZX9 | Twisted gastrulation protein homolog 1 | TWSG1 |
| Q9GZZ7 | GDNF family receptor alpha-4 | GFRA4 |
| Q9GZZ8 | Extracellular glycoprotein lacritin | LACRT |
| Q9H0B8 | Cysteine-rich secretory protein LCCL domain-containing 2 | CRISPLD2 |

TABLE 1-continued

Secreted Proteins

| Uniprot ID | Protein Name | Gene Name |
| --- | --- | --- |
| Q9H106 | Signal-regulatory protein delta | SIRPD |
| Q9H114 | Cystatin-like 1 | CSTL1 |
| Q9H173 | Nucleotide exchange factor SIL1 | SIL1 |
| Q9H1E1 | Ribonuclease 7 | RNASE7 |
| Q9H1F0 | WAP four-disulfide core domain protein 10A | WFDC10A |
| Q9H1J5 | Protein Wnt-8a | WNT8A |
| Q9H1J7 | Protein Wnt-5b | WNT5B |
| Q9H1M3 | Beta-defensin 129 | DEFB129 |
| Q9H1M4 | Beta-defensin 127 | DEFB127 |
| Q9H1Z8 | Augurin | C2orf40 |
| Q9H239 | Matrix metalloproteinase-28 | MMP28 |
| Q9H2A7 | C-X-C motif chemokine 16 | CXCL16 |
| Q9H2A9 | Carbohydrate sulfotransferase 8 | CHST8 |
| Q9H2R5 | Kallikrein-15 | KLK15 |
| Q9H2X0 | Chordin | CHRD |
| Q9H2X3 | C-type lectin domain family 4 member M | CLEC4M |
| Q9H306 | Matrix metalloproteinase-27 | MMP27 |
| Q9H324 | A disintegrin and metalloproteinase with thrombospondin motifs 10 | ADAMTS10 |
| Q9H336 | Cysteine-rich secretory protein LCCL domain-containing 1 | CRISPLD1 |
| Q9H3E2 | Sorting nexin-25 | SNX25 |
| Q9H3R2 | Mucin-13 | MUC13 |
| Q9H3U7 | SPARC-related modular calcium-binding protein 2 | SMOC2 |
| Q9H3Y0 | Peptidase inhibitor R3HDML | R3HDML |
| Q9H4A4 | Aminopeptidase B | RNPEP |
| Q9H4F8 | SPARC-related modular calcium-binding protein 1 | SMOC1 |
| Q9H4G1 | Cystatin-9-like | CST9L |
| Q9H5V8 | CUB domain-containing protein 1 | CDCP1 |
| Q9H6B9 | Epoxide hydrolase 3 | EPHX3 |
| Q9H6E4 | Coiled-coil domain-containing protein 134 | CCDC134 |
| Q9H741 | UPF0454 protein C12orf49 | C12orf49 |
| Q9H772 | Gremlin-2 | GREM2 |
| Q9H7Y0 | Deleted in autism-related protein 1 | CXorf36 |
| Q9H8L6 | Multimerin-2 | MMRN2 |
| Q9H9S5 | Fukutin-related protein | FKRP |
| Q9HAT2 | Sialate O-acetylesterase | SIAE |
| Q9HB40 | Retinoid-inducible serine carboxypeptidase | SCPEP1 |
| Q9HB63 | Netrin-4 | NTN4 |
| Q9HBJ0 | Placenta-specific protein 1 | PLAC1 |
| Q9HC23 | Prokineticin-2 | PROK2 |
| Q9HC57 | WAP four-disulfide core domain protein 1 | WFDC1 |
| Q9HC73 | Cytokine receptor-like factor 2 | CRLF2 |
| Q9HC84 | Mucin-5B | MUC5B |
| Q9HCB6 | Spondin-1 | SPON1 |
| Q9HCQ7 | Neuropeptide NPSF | NPVF |
| Q9HCT0 | Fibroblast growth factor 22 | FGF22 |
| Q9HD89 | Resistin | RETN |
| Q9NNX1 | Tuftelin | TUFT1 |
| Q9NNX6 | CD209 antigen | CD209 |
| Q9NP55 | BPI fold-containing family A member 1 | BPIFA1 |
| Q9NP70 | Ameloblastin | AMBN |
| Q9NP95 | Fibroblast growth factor 20 | FGF20 |
| Q9NP99 | Triggering receptor expressed on myeloid cells 1 | TREM1 |
| Q9NPA2 | Matrix metalloproteinase-25 | MMP25 |
| Q9NPE2 | Neugrin | NGRN |
| Q9NPH0 | Lysophosphatidic acid phosphatase type 6 | ACP6 |
| Q9NPH6 | Odorant-binding protein 2b | OBP2B |
| Q9NQ30 | Endothelial cell-specific molecule 1 | ESM1 |
| Q9NQ36 | Signal peptide, CUB and EGF-like domain-containing protein 2 | SCUBE2 |
| Q9NQ38 | Serine protease inhibitor Kazal-type 5 | SPINK5 |
| Q9NQ76 | Matrix extracellular phosphoglycoprotein | MEPE |
| Q9NQ79 | Cartilage acidic protein 1 | CRTAC1 |
| Q9NR16 | Scavenger receptor cysteine-rich type 1 protein M160 | CD163L1 |
| Q9NR23 | Growth/differentiation factor 3 | GDF3 |
| Q9NR71 | Neutral ceramidase | ASAH2 |
| Q9NR99 | Matrix-remodeling-associated protein 5 | MXRA5 |
| Q9NRA1 | Platelet-derived growth factor C | PDGFC |
| Q9NRC9 | Otoraplin | OTOR |
| Q9NRE1 | Matrix metalloproteinase-26 | MMP26 |
| Q9NRJ3 | C-C motif chemokine 28 | CCL28 |
| Q9NRM1 | Enamelin | ENAM |
| Q9NRN5 | Olfactomedin-like protein 3 | OLFML3 |
| Q9NRR1 | Cytokine-like protein 1 | CYTL1 |

TABLE 1-continued

Secreted Proteins

| Uniprot ID | Protein Name | Gene Name |
| --- | --- | --- |
| Q9NS15 | Latent-transforming growth factor beta-binding protein 3 | LTBP3 |
| Q9NS62 | Thrombospondin type-1 domain-containing protein 1 | THSD1 |
| Q9NS71 | Gastrokine-1 | GKN1 |
| Q9NS98 | Semaphorin-3G | SEMA3G |
| Q9NSA1 | Fibroblast growth factor 21 | FGF21 |
| Q9NT22 | EMILIN-3 | EMILIN3 |
| Q9NTU7 | Cerebellin-4 | CBLN4 |
| Q9NVR0 | Kelch-like protein 11 | KLHL11 |
| Q9NWH7 | Spermatogenesis-associated protein 6 | SPATA6 |
| Q9NXC2 | Glucose-fructose oxidoreductase domain-containing protein 1 | GFOD1 |
| Q9NY56 | Odorant-binding protein 2a | OBP2A |
| Q9NY84 | Vascular non-inflammatory molecule 3 | VNN3 |
| Q9NZ20 | Group 3 secretory phospholipase A2 | PLA2G3 |
| Q9NZC2 | Triggering receptor expressed on myeloid cells 2 | TREM2 |
| Q9NZK5 | Adenosine deaminase CECR1 | CECR1 |
| Q9NZK7 | Group IIE secretory phospholipase A2 | PLA2G2E |
| Q9NZP8 | Complement C1r subcomponent-like protein | C1RL |
| Q9NZV1 | Cysteine-rich motor neuron 1 protein | CRIM1 |
| Q9NZW4 | Dentin sialoprotein | DSPP |
| Q9P0G3 | Kallikrein-14 | KLK14 |
| Q9P0W0 | Interferon kappa | IFNK |
| Q9P218 | Collagen alpha-1(XX) chain | COL20A1 |
| Q9P2C4 | Transmembrane protein 181 | TMEM181 |
| Q9P2K2 | Thioredoxin domain-containing protein 16 | TXNDC16 |
| Q9P2N4 | A disintegrin and metalloproteinase with thrombospondin motifs 9 | ADAMTS9 |
| Q9UBC7 | Galanin-like peptide | GALP |
| Q9UBD3 | Cytokine SCM-1 beta | XCL2 |
| Q9UBD9 | Cardiotrophin-like cytokine factor 1 | CLCF1 |
| Q9UBM4 | Opticin | OPTC |
| Q9UBP4 | Dickkopf-related protein 3 | DKK3 |
| Q9UBQ6 | Exostosin-like 2 | EXTL2 |
| Q9UBR5 | Chemokine-like factor | CKLF |
| Q9UBS5 | Gamma-aminobutyric acid type B receptor subunit 1 | GABBR1 |
| Q9UBT3 | Dickkopf-related protein 4 short form | DKK4 |
| Q9UBU2 | Dickkopf-related protein 2 | DKK2 |
| Q9UBU3 | Ghrelin-28 | GHRL |
| Q9UBV4 | Protein Wnt-16 | WNT16 |
| Q9UBX5 | Fibulin-5 | FBLN5 |
| Q9UBX7 | Kallikrein-11 | KLK11 |
| Q9UEF7 | Klotho | KL |
| Q9UFP1 | Protein FAM198A | FAM198A |
| Q9UGM3 | Deleted in malignant brain tumors 1 protein | DMBT1 |
| Q9UGM5 | Fetuin-B | FETUB |
| Q9UGP8 | Translocation protein SEC63 homolog | SEC63 |
| Q9UHF0 | Neurokinin-B | TAC3 |
| Q9UHF1 | Epidermal growth factor-like protein 7 | EGFL7 |
| Q9UHG2 | ProSAAS | PCSK1N |
| Q9UHI8 | A disintegrin and metalloproteinase with thrombospondin motifs 1 | ADAMTS1 |
| Q9UHL4 | Dipeptidyl peptidase 2 | DPP7 |
| Q9UI42 | Carboxypeptidase A4 | CPA4 |
| Q9UIG4 | Psoriasis susceptibility 1 candidate gene 2 protein | PSORS1C2 |
| Q9UIK5 | Tomoregulin-2 | TMEFF2 |
| Q9UIQ6 | Leucyl-cystinyl aminopeptidase, pregnancy serum form | LNPEP |
| Q9UJA9 | Ectonucleotide pyrophosphatase/phosphodiesterase family member 5 | ENPP5 |
| Q9UJH8 | Meteorin | METRN |
| Q9UJJ9 | N-acetylglucosamine-1-phosphotransferase subunit gamma | GNPTG |
| Q9UJW2 | Tubulointerstitial nephritis antigen | TINAG |
| Q9UK05 | Growth/differentiation factor 2 | GDF2 |
| Q9UK55 | Protein Z-dependent protease inhibitor | SERPINA10 |
| Q9UK85 | Dickkopf-like protein 1 | DKKL1 |
| Q9UKJ1 | Paired immunoglobulin-like type 2 receptor alpha | PILRA |
| Q9UKP4 | A disintegrin and metalloproteinase with thrombospondin motifs 7 | ADAMTS7 |
| Q9UKP5 | A disintegrin and metalloproteinase with thrombospondin motifs 6 | ADAMTS6 |

TABLE 1-continued

Secreted Proteins

| Uniprot ID | Protein Name | Gene Name |
|---|---|---|
| Q9UKQ2 | Disintegrin and metalloproteinase domain-containing protein 28 | ADAM28 |
| Q9UKQ9 | Kallikrein-9 | KLK9 |
| Q9UKR0 | Kallikrein-12 | KLK12 |
| Q9UKR3 | Kallikrein-13 | KLK13 |
| Q9UKU9 | Angiopoietin-related protein 2 | ANGPTL2 |
| Q9UKZ9 | Procollagen C-endopeptidase enhancer 2 | PCOLCE2 |
| Q9UL52 | Transmembrane protease serine 11E non-catalytic chain | TMPRSS11E |
| Q9ULC0 | Endomucin | EMCN |
| Q9ULI3 | Protein HEG homolog 1 | HEG1 |
| Q9ULZ1 | Apelin-13 | APLN |
| Q9ULZ9 | Matrix metalloproteinase-17 | MMP17 |
| Q9UM21 | Alpha-1,3-mannosyl-glycoprotein 4-beta-N-acetylglucosaminyltransferase A soluble form | MGAT4A |
| Q9UM22 | Mammalian ependymin-related protein 1 | EPDR1 |
| Q9UM73 | ALK tyrosine kinase receptor | ALK |
| Q9UMD9 | 97 kDa linear IgA disease antigen | COL17A1 |
| Q9UMX5 | Neudesin | NENF |
| Q9UN73 | Protocadherin alpha-6 | PCDHA6 |
| Q9UNA0 | A disintegrin and metalloproteinase with thrombospondin motifs 5 | ADAMTS5 |
| Q9UNI1 | Chymotrypsin-like elastase family member 1 | CELA1 |
| Q9UNK4 | Group IID secretory phospholipase A2 | PLA2G2D |
| Q9UP79 | A disintegrin and metalloproteinase with thrombospondin motifs 8 | ADAMTS8 |
| Q9UPZ6 | Thrombospondin type-1 domain-containing protein 7A | THSD7A |
| Q9UQ72 | Pregnancy-specific beta-1-glycoprotein 11 | PSG11 |
| Q9UQ74 | Pregnancy-specific beta-1-glycoprotein 8 | PSG8 |
| Q9UQC9 | Calcium-activated chloride channel regulator 2 | CLCA2 |
| Q9UQE7 | Structural maintenance of chromosomes protein 3 | SMC3 |
| Q9UQP3 | Tenascin-N | TNN |
| Q9Y223 | UDP-N-acetylglucosamine 2-epimerase | GNE |
| Q9Y240 | C-type lectin domain family 11 member A | CLEC11A |
| Q9Y251 | Heparanase 8 kDa subunit | HPSE |
| Q9Y258 | C-C motif chemokine 26 | CCL26 |
| Q9Y264 | Angiopoietin-4 | ANGPT4 |
| Q9Y275 | Tumor necrosis factor ligand superfamily member 13b, membrane form | TNFSF13B |
| Q9Y287 | BRI2 intracellular domain | ITM2B |
| Q9Y2E5 | Epididymis-specific alpha-mannosidase | MAN2B2 |
| Q9Y334 | von Willebrand factor A domain-containing protein 7 | VWA7 |
| Q9Y337 | Kallikrein-5 | KLK5 |
| Q9Y3B3 | Transmembrane emp24 domain-containing protein 7 | TMED7 |
| Q9Y3E2 | BolA-like protein 1 | BOLA1 |
| Q9Y426 | C2 domain-containing protein 2 | C2CD2 |
| Q9Y4K0 | Lysyl oxidase homolog 2 | LOXL2 |
| Q9Y4X3 | C-C motif chemokine 27 | CCL27 |
| Q9Y5C1 | Angiopoietin-related protein 3 | ANGPTL3 |
| Q9Y5I2 | Protocadherin alpha-10 | PCDHA10 |
| Q9Y5I3 | Protocadherin alpha-1 | PCDHA1 |
| Q9Y5K2 | Kallikrein-4 | KLK4 |
| Q9Y5L2 | Hypoxia-inducible lipid droplet-associated protein | HILPDA |
| Q9Y5Q5 | Atrial natriuretic peptide-converting enzyme | CORIN |
| Q9Y5R2 | Matrix metalloproteinase-24 | MMP24 |
| Q9Y5U5 | Tumor necrosis factor receptor superfamily member 18 | TNFRSF18 |
| Q9Y5W5 | Wnt inhibitory factor 1 | WIF1 |
| Q9Y5X9 | Endothelial lipase | LIPG |
| Q9Y625 | Secreted glypican-6 | GPC6 |
| Q9Y646 | Carboxypeptidase Q | CPQ |
| Q9Y6C2 | EMILIN-1 | EMILIN1 |
| Q9Y6F9 | Protein Wnt-6 | WNT6 |
| Q9Y6I9 | Testis-expressed sequence 264 protein | TEX264 |
| Q9Y6L7 | Tolloid-like protein 2 | TLL2 |
| Q9Y6N3 | Calcium-activated chloride channel regulator family member 3 | CLCA3P |
| Q9Y6N6 | Laminin subunit gamma-3 | LAMC3 |
| Q9Y6R7 | IgGFc-binding protein | FCGBP |
| Q9Y6Y9 | Lymphocyte antigen 96 | LY96 |
| Q9Y6Z7 | Collectin-10 | COLEC10 |

In some embodiments, the compositions and methods of the invention provide for the delivery of one or more mRNAs encoding one or more additional exemplary proteins listed in Table 2; thus, compositions of the invention may comprise an mRNA encoding a protein listed in Table 2 (or a homolog thereof) along with other components set out herein, and methods of the invention may comprise preparing and/or administering a composition comprising an mRNA encoding a protein chosen from the proteins listed in Table 2 (or a homolog thereof) along with other components set out herein.

In some embodiments, compositions and methods of the invention provide for the delivery of one or more nucleic acids that bind to or otherwise act on an endogenous nucleic acid, such as endogenous mRNA or DNA, that alter the transcription, translation, secretion, or action of one or more proteins or genes listed in Table 2 (or a homolog thereof). For example, RNAi nucleic acids bind to endogenous mRNA, miRNA, or other RNAs, while guide RNA (gRNA) and CRISPR RNA (crRNA) respectively bind to DNA and act on DNA in the nucleus. Accordingly, in embodiments, the compositions and methods of the invention provide for delivery of nucleic acids including one or more of RNAi nucleic acids, gRNA and crRNA to interfere with the transcription, translation, secretion, or action of one or more proteins or genes listed in Table 2 (and homologs thereof) along with other components set out herein.

TABLE 2

Additional Exemplary Proteins

| Uniprot ID | Protein Name | Gene Name |
| --- | --- | --- |
| A6NGW2 | Putative stereocilin-like protein | STRCP1 |
| A6NIE9 | Putative serine protease 29 | PRSS29P |
| A6NJ16 | Putative V-set and immunoglobulin domain-containing-like protein IGHV4OR15-8 | IGHV4OR15-8 |
| A6NJS3 | Putative V-set and immunoglobulin domain-containing-like protein IGHV1OR21-1 | IGHV1OR21-1 |
| A6NMY6 | Putative annexin A2-like protein | ANXA2P2 |
| A8MT79 | Putative zinc-alpha-2-glycoprotein-like 1 | |
| A8MWS1 | Putative killer cell immunoglobulin-like receptor like protein KIR3DP1 | KIR3DP1 |
| A8MXU0 | Putative beta-defensin 108A | DEFB108P1 |
| C9JUS6 | Putative adrenomedullin-5-like protein | ADM5 |
| P0C7V7 | Putative signal peptidase complex catalytic subunit SEC11B | SEC11B |
| P0C854 | Putative cat eye syndrome critical region protein 9 | CECR9 |
| Q13046 | Putative pregnancy-specific beta-1-glycoprotein 7 | PSG7 |
| Q16609 | Putative apolipoprotein(a)-like protein 2 | LPAL2 |
| Q2TV78 | Putative macrophage-stimulating protein MSTP9 | MST1P9 |
| Q5JQD4 | Putative peptide YY-3 | PYY3 |
| Q5R387 | Putative inactive group IIC secretory phospholipase A2 | PLA2G2C |
| Q5VSP4 | Putative lipocalin 1-like protein 1 | LCN1P1 |
| Q5W188 | Putative cystatin-9-like protein CST9LP1 | CST9LP1 |
| Q6UXR4 | Putative serpin A13 | SERPINA13P |
| Q86SH4 | Putative testis-specific prion protein | PRNT |
| Q86YQ2 | Putative latherin | LATH |
| Q8IVG9 | Putative humanin peptide | MT-RNR2 |
| Q8NHM4 | Putative trypsin-6 | TRY6 |
| Q8NHW4 | C-C motif chemokine 4-like | CCL4L2 |
| Q9H7L2 | Putative killer cell immunoglobulin-like receptor-like protein KIR3DX1 | KIR3DX1 |
| Q9NRI6 | Putative peptide YY-2 | PYY2 |
| Q9UF72 | Putative TP73 antisense gene protein 1 | TP73-AS1 |
| Q9UKY3 | Putative inactive carboxylesterase 4 | CES1P1 |

The Uniprot IDs set forth in Table 1 and Table 2 refer to the human versions the listed proteins and the sequences of each are available from the Uniprot database. Sequences of the listed proteins are also generally available for various animals, including various mammals and animals of veterinary or industrial interest. Accordingly, in some embodiments, compositions and methods of the invention provide for the delivery of one or more mRNAs encoding one or more proteins chosen from mammalian homologs or homologs from an animal of veterinary or industrial interest of the secreted proteins listed in Table 1 and Table 2; thus, compositions of the invention may comprise an mRNA encoding a protein chosen from mammalian homologs or homologs from an animal of veterinary or industrial interest of a protein listed in Table 1 and Table 2 along with other components set out herein, and methods of the invention may comprise preparing and/or administering a composition comprising an mRNA encoding a protein chosen from mammalian homologs or homologs from an animal of veterinary or industrial interest of a protein listed in Table 1 and Table 2 along with other components set out herein. In some embodiments, mammalian homologs are chosen from mouse, rat, hamster, gerbil, horse, pig, cow, llama, alpaca, mink, dog, cat, ferret, sheep, goat, or camel homologs. In some embodiments, the animal of veterinary or industrial interest is chosen from the mammals listed above and/or chicken, duck, turkey, salmon, catfish, or tilapia.

In embodiments, the compositions and methods of the invention provide for the delivery of mRNA encoding a protein chosen from Table 3. In some embodiments, the compositions and methods of the invention provide for the delivery of one or more mRNAs encoding one or more proteins listed in Table 3; thus, compositions of the invention may comprise an mRNA encoding a protein listed in Table 3 (or a homolog thereof) along with other components set out herein, and methods of the invention may comprise preparing and/or administering a composition comprising an mRNA encoding a protein chosen from the proteins listed in Table 3 (or a homolog thereof) along with other components set out herein.

In some embodiments, compositions and methods of the invention provide for the delivery of one or more nucleic acids that bind to or otherwise act on an endogenous nucleic acid, such as endogenous mRNA or DNA, that alter the transcription, translation, secretion, or action of one or more proteins listed in Table 3 (or a homolog thereof). For example, RNAi nucleic acids bind to endogenous mRNA, miRNA, or other RNAs, while guide RNA (gRNA) and CRISPR RNA (crRNA) respectively bind to DNA and act on DNA in the nucleus. Accordingly, in embodiments, the compositions and methods of the invention provide for delivery of nucleic acids including one or more of RNAi nucleic acids, gRNA and crRNA to interfere with the transcription, translation, secretion, or action of one or more proteins listed in Table 3 (and homologs thereof) along with other components set out herein.

TABLE 3

Lysosomal and Related Proteins

α-fucosidase
α-galactosidase
α-glucosidase
α-Iduronidase
α-mannosidase
α-N-acetylgalactosaminidase (α-galactosidase B)
β-galactosidase TABLE 3-continued Lysosomal and Related Proteins β-glucuronidase
β-hexosaminidase
β-mannosidase
3-hydroxy-3-methylglutaryl-CoA (HMG-CoA) lyase
3-methylcrotonyl-CoA carboxylase
3-O-sulfogalactosyl cerebroside sulfatase (arylsulfatase A)
acetyl-CoA transferase
acid alpha-glucosidase
acid ceramidase
acid lipase
acid phosphatase
acid sphingomyelinase
alpha-galactosidase A
arylsulfatase A
beta-galactosidase
beta-glucocerebrosidase
beta-hexosaminidase
biotinidase
cathepsin A
cathepsin K
CLN3
CLN5
CLN6
CLN8
CLN9
cystine transporter (cystinosin)
cytosolic protein beta3A subunit of the adaptor protein-3 complex, AP3
formyl-Glycine generating enzyme (FGE)
galactocerebrosidase
galactose-1-phosphate uridyltransferase (GALT)
galactose 6-sulfate sulfatase
(also known as N-acetylgalactosamine-6-sulfatase)
glucocerebrosidase
glucuronate sulfatase
glucuronidase
glycoprotein cleaving enzymes
glycosaminoglycan cleaving enzymes
glycosylasparaginase (aspartylglucosaminidase)
GM2-AP
Heparan-alpha-glucosaminide N-acetyltransferase (HGSNAT, TMEM76)
Heparan sulfatase
hexosaminidase A lysosomal proteases methylmalonyl-CoA mutase
hyaluronidase
Iduronate sulfatase
LAMP-2
lysosomal α-mannosidase
Lysosomal p40 (C2orf18)
Major facilitator superfamily domain containing 8 protein (MFSD8 or CLN7)
N-acetylgalactosamine 4-sulfatase
N-acetyl glucosamine 6-sulfatase
N-acetyl glucosaminidase
N-acetylglucosamine-1-phosphate transferase
NPC1
NPC2
palmitoyl-protein thioesterase
palmitoyl-protein thioesterase (CLN1)
Saposin A (Sphingolipid activator protein A)
Saposin B (Sphingolipid activator protein B)
Saposin C (Sphingolipid activator protein C)
Saposin D (Sphingolipid activator protein D)
sialic acid transporter (sialin)
sialidase
Sialin
sulfatase
Transmembrane protein 74 (TMEM74)
tripeptidyl-peptidase
tripeptidyl-peptidase I (CLN2)
UDP-N-acetylglucosamine-phosphotransferase Information regarding lysosomal proteins is available from Lubke et al., "Proteomics of the Lysosome," *Biochim Biophys Acta*. (2009) 1793: 625-635. In some embodiments, the protein listed in Table 3 and encoded by mRNA in the compositions and methods of the invention is a human protein. Sequences of the listed proteins are also available for various animals, including various mammals and animals of veterinary or industrial interest as described above.

In some embodiments, the compositions and methods of the invention provide for the delivery of mRNA encoding a therapeutic protein (e.g., cytosolic, transmembrane or secreted) such as those listed in Table 4. In some embodiments, the compositions and methods of the invention provide for the delivery of an mRNA encoding a therapeutic protein useful in treating a disease or disorder (i.e., indication) listed in Table 4; thus, compositions of the invention may comprise an mRNA encoding a therapeutic protein listed or not listed in Table 4 (or a homolog thereof, as discussed below) along with other components set out herein for treating a disease or disorder (i.e., indication) listed in Table 4, and methods of the invention may comprise preparing and/or administering a composition comprising an mRNA encoding a such a protein (or a homolog thereof, as discussed below) along with other components set out herein for treatment of a disease or disorder listed in Table 4.

In some embodiments, the compositions and methods of the invention provide for the delivery of one or more nucleic acids that bind to or otherwise act on an endogenous nucleic acid, such as endogenous mRNA or DNA, that alter the transcription, translation, secretion, or action of one or more proteins listed in Table 4 (or homologs thereof) or proteins useful in treating a disease or disorder (i.e., indication) listed in Table 4. For example, RNAi nucleic acids bind to endogenous mRNA, miRNA, or other RNAs, while guide RNA (gRNA) and CRISPR RNA (crRNA) respectively bind to DNA and act on DNA in the nucleus. Accordingly, in some embodiments, the compositions and methods of the invention provide for delivery of nucleic acids including one or more of RNAi nucleic acids, gRNA and crRNA to interfere with the transcription, translation, secretion, or action of one or more proteins listed in Table 4 (and homologs thereof) or proteins useful in treating a disease or disorder (i.e., indication) listed in Table 4, along with other components set out herein.

TABLE 4

Exemplary Indications and Related Proteins

| Indication | Therapeutic Protein |
| --- | --- |
| 3-Methylcrotonyl-CoA carboxylase deficiency | Methylcrotonoyl-CoA carboxylase |
| 3-Methylglutaconic aciduria | Methylglutaconyl-CoA hydratase |
| Actinic keratosis | |
| Acute intermittent porphyria | Porphobilinogen deaminase |
| Acute lymphocytic leukemia | |
| Acute myeloid leukemia | |
| Addison's disease | |

TABLE 4-continued

Exemplary Indications and Related Proteins

| Indication | Therapeutic Protein |
|---|---|
| Adenosine deaminase deficiency | Adenosine deaminase |
| Adrenoleukodystrophy | ABCD1 |
| Adrenomyeloneuropathy | |
| AIDS/HIV | |
| Alcohol use disorders | |
| Alkaptonuria | Homogentisate 1,2-dioxygenase |
| Allergic asthma | Anti-IgE mAb |
| Allergies (dermatitis, rhinitis) | |
| Alopecia areata | |
| Alpers' disease | POLG |
| Alpers-Huttenlocher syndrome | |
| Alpha 1-antitrypsin deficiency | Alpha 1 protease inhibitor |
| Alpha-mannosidosis | Alpha-D-mannosidase |
| Alport syndrome | |
| Alzheimer's disease | |
| Amyloid light-chain amyloidosis | |
| Amyotrophic lateral sclerosis (ALS) | |
| Anemia | Erythropoietin |
| Aortic valve stenosis | |
| Argininemia | Arginase |
| Argininosuccinic acidemia | Argininosuccinate lyase |
| Arrhythmogenic right ventricular dysplasia | |
| Autism | |
| Autosomal dominant and recessive progressive external ophthalmoplegia with mitochondrial DNA deletions | |
| Autosomal recessive polycystic kidney disease | ARPKD |
| Bacterial infections | |
| Basal cell carcinoma | |
| Batten disease | Battenin + others |
| B-cell chronic lymphocytic leukemia | |
| Becker muscular dystrophy | Dystrophin |
| Beta-thalassemia | Beta globin |
| Binge eating disorder | |
| Bipolar disorder | |
| Bladder cancer | |
| Blepharospasm, Cervical dystonia, Chronic migraine, more | Botulinum toxin |
| Bronchiolitis obliterans | |
| Brugada syndrome | |
| Buerger's disease | |
| CACNA1A | |
| CACNB4-related Episodic Ataxia Type 2 | |
| Cancer and depression | |
| Cancer and sexual dysfunction | |
| Cancer in pregnancy | |
| Carbamylphosphate synthetase deficiency | Carbamylphosphate synthetase |
| Carcinoma of the gallbladder | |
| Cardiomyopathy (diabetic) | |
| Cardiomyopathy (hypertrophic) | |
| Carnitine uptake defect | SLC22A5 |
| Catecholaminergic polymorphic ventricular tachycardia | |
| CDKL5-related Atypical Rett Syndrome | |
| Celiac disease | |
| Cellulitis | |
| Cerebrovascular disease | |
| Cervix uteri cancer | |
| Chronic fatigue syndrome | |
| Chronic graft versus host disease | |
| Chronic idiopathic urticaria | |
| Chronic immune thrombocytopenia | Thrombopoietin |
| Chronic kidney kisease | |
| Chronic liver disease | |
| Chronic lymphocytic leukemia | |
| Chronic myeloid leukemia | |
| Chronic pancreatitis | |
| Cirrhosis of the liver | |
| Citrullinemia, type I | Argininosuccinate synthase |
| Classic Rett Syndrome | |
| Classical galactosemia | Galactose-1-phosphate uridylyltransferase |
| *Clostridium difficile* associated diarrhea | |
| Clotting disorders | |
| COAD/COPD | |
| Cocaine addiction | |
| COL4A5-related disorders | |

TABLE 4-continued

Exemplary Indications and Related Proteins

| Indication | Therapeutic Protein |
|---|---|
| Cold contact urticaria | |
| Contraception, female | |
| Coronary artery diseases | |
| Corpus uteri cancer | |
| Corticobasal degeneration | |
| Crigler-Najjar syndrome | UDP-glucuronosyltransferase |
| Critical limb ischemia | |
| CTNS-related cystinosis | |
| Cutaneous lupus erythematosus | |
| Cutaneous neuroendocrine carcinoma (Merkel Cell) | |
| Cystic fibrosis | CFTR |
| Cystic fibrosis | Deoxyribonuclease I |
| Cystinosis | Cystinosin |
| Cystinuria | SLC7A9 |
| Dementia (Lewy body) | |
| Depression | |
| Diabetic foot infections | |
| Diabetic foot ulcer | |
| Diabetic peripheral neuropathy | |
| Diabetic ulcers | |
| Diarrhoeal diseases | |
| Diffuse large B-cell lymphoma | |
| DiGeorge syndrome | |
| Diverticulitis | |
| Drug use disorders | |
| Duchenne muscular dystrophy | Dystrophin |
| Dysarthria | |
| Dyskinesia (levodopa-induced) | |
| Early-onset autosomal dominant Alzheimer's disease | |
| Eczema | |
| Ehlers-Danlos syndrome, type 1 | |
| EIF2B1 | |
| EIF2B2 | |
| EIF2B3 | |
| EIF2B4 | |
| EIF2B5-related childhood ataxia with central nervous system hypomyelination/vanishing white matter | |
| Eosinophilic esophagitis | |
| Epilepsy | |
| Erectile dysfunction | |
| Erythropoietic protoporphyria | Ferrochelatase |
| Esophageal carcinoma | |
| Essential tremor | |
| Fabry disease | Alpha galactosidase |
| Familial adenomatous polyposis | APC |
| Familial chylomicronemia | Lipoprotein lipase |
| Familial dysbetalipoproteinemia | Apolipoprotein E |
| Familial isolated dilated cardiomyopathy | |
| Familial mediterranean fever | Pyrin (MEFV) |
| Familial melanoma | |
| Female infertility | Follicle stimulating hormone |
| Female sexual dysfunction | |
| Fibromyalgia | |
| FMR1-related disorders | |
| Fracture healing | |
| Fragile X Premature Ovarian Failure Syndrome | |
| Fragile X syndrome | FMRP |
| Fragile X-Associated Tremor/Ataxia Syndrome | |
| Friedreich's ataxia | |
| Frontotemporal dementia | |
| Fryns syndrome | |
| Galactocerebrosidase deficiencies | |
| GALE deficiency | Galactose epimerase |
| GALK deficiency | Galactokinase |
| GALT-related galactosemia | |
| Gastric cancer | |
| Gastroesophageal reflux disease | |
| Gaucher disease | Glucocerebrosidase |
| Gilbert syndrome | UDP-glucuronosyltransferase |
| Glioblastoma multiforme | |
| Glomerulonephritis | |
| Glutaric acidemia, type I | Glutaryl-CoA dehydrogenase |
| GM2 gangliosidosis | HEXA, HEXB |
| Gout | Urate oxidase |
| Graft versus host disease | |

TABLE 4-continued

Exemplary Indications and Related Proteins

| Indication | Therapeutic Protein |
|---|---|
| Growth hormone deficiency | Growth hormone 1/Growth hormone 2 |
| Head and neck cancer, Metastatic colorectal cancer | Anti-EGFr mAb |
| Hearing loss, adult onset | |
| Heart failure | |
| Hemachromatosis | HFE protein |
| Hemifacial spasm | |
| Hemolytic uremic syndrome | Anti-complement factor C5 mAb |
| Hemophilia A | Factor VIII |
| Hemophilia A, Hemophilia B | Factor VII |
| Hemophilia B | Factor IX |
| Hepatitis B, Hepatitis C | Interferon alpha |
| HER2+ breast cancer, gastric cancer | Anti-HER2 mAb |
| Hereditary angioedema | C1 esterase inhibitor |
| Hereditary hemorrhagic telangiectasia | |
| Hereditary hemorrhagic telangiectasia (AT) | |
| Hereditary spherocytosis | |
| Hidradenitis suppurativa | |
| Homocystinuria | Cystathionine beta-synthase |
| Homozygous familial hypercholesterolemia | LDL receptor |
| Hunter syndrome (MPS II) | Iduronate-2-sulfatase |
| Huntington disease | Huntingtin |
| Hurler syndrome (MPS I) | Alpha-L iduronidase |
| Hydrolethalus | |
| Hyperalgesia | |
| Hyperbilirubinemia | |
| Hyperhidrosis | |
| Hyperlipidemia | |
| Hypermethioninemia | Methionine adenosyltransferase |
| Hyperoxaluria, type I | Serine-pyruvate aminotransferase |
| Hypertension | |
| Hyperuricemia | |
| Hyponatremia | |
| Hypoparathyroidism | Parathyroid hormone |
| Hypophosphatasia | TNSALP |
| Idiopathic pulmonary fibrosis | |
| Iminoglycinuria | |
| Immunoglobulin deficiency | Immunoglobulin |
| Infection (adenovirus) | |
| Infection (anthrax prophylaxis) | |
| Infection (BK virus) | |
| Infection (*Clostridium difficile* prophylaxis) | |
| Infection (Dengue fever prophylaxis) | |
| Infection (Epstein-Barr virus) | |
| Infection (Hepatitis-D) | |
| Infection (Lyme disease prophylaxis) | |
| Infection (Smallpox virus) | |
| Infectious diseases vaccines | Infectious antigen |
| Inflammatory heart diseases | |
| Insomnia | |
| Interstitial cystitis | |
| Iron-deficiency anaemia | |
| Irritable bowel disease | |
| Ischaemic heart disease | |
| Isovaleric aciduria | Isovaleric acid CoA dehydrogenase deficiency |
| Jansky-Bielschowsky disease | |
| Juvenile Batten disease | |
| Juvenile Neuronal Ceroid Lipofuscinosis (JNCL) | |
| Juvenile rheumatoid arthritis | TNF-alpha inhibitors |
| Kennedy's disease (SBMA) | |
| Keratoconus | |
| Krabbe disease | Galactocerebrosidase |
| Leber's hereditary optic neuropathy | NADH dehydrogenase |
| Leiomyosarcoma | |
| Lennox-Gastaut syndrome | |
| Lesch-Nyhan syndrome | Hypoxanthine phosphoribosyltransferase 1 |
| Leukaemia | |
| Li-Fraumeni syndrome | TP53 |
| Lipoma | |
| Liposarcoma | |
| Liver cancer | |
| Long-chain 3-OH acyl-CoA dehydrogenase deficiency | Long-chain-3-hydroxyacyl-CoA dehydrogenase |
| Lower respiratory infections | |

TABLE 4-continued

Exemplary Indications and Related Proteins

| Indication | Therapeutic Protein |
|---|---|
| Lysosomal acid lipase deficiency | Lysosomal acid lipase |
| Macular degeneration | |
| Major depressive disorder | |
| Malignant fibrous histiocytoma | |
| Mantle cell lymphoma | |
| Maple syrup urine disease | 3-methyl-2-oxobutanoate dehydrogenase |
| Marfan syndrome | FBN1 |
| Maroteaux-Lamy syndrome (MPS VI) | N-acetylgalactosamine 4-sulfatase |
| Mastocytosis | |
| McArdle disease | Muscle glycogen phosphorylase |
| MECP2-related disorders | |
| MECP2-related Severe Neonatal Encephalopathy | |
| Medium-chain acyl-CoA dehydrogenase deficiency | Acyl-CoA dehydrogenase |
| Melanoma | Anti-CTLA4 mAb |
| Metachromatic leukodystrophy | Arylsulfatase A |
| Metastatic colorectal cancer, NSCLC, others | Anti-VEGF mAb |
| Methylmalonyl-CoA mutase deficiency | Methylmalonyl-CoA mutase |
| Migraine | |
| Mitochondrial oxidative phosphorylation disorders | |
| Morquio syndrome, type A (MPS IVA) | Galactose 6-sulfate sulfatase |
| Morquio syndrome, type B (MPS IVB) | Beta-galactosidase |
| Mouth and oropharynx cancers | |
| Multiple carboxylase deficiency | Biotin-methylcrotonoyl-CoA-carboxylase ligase |
| Multiple myeloma | |
| Multiple sclerosis | Anti-VLA-4 mAb |
| Multiple sclerosis | Interferon beta |
| Multiple system atrophy | |
| Myasthenia gravis | |
| Myelofibrosis | |
| Narcolepsy | |
| Neonatal bronchopulmonary dysplasia | |
| Neonatal infections | |
| Nephritis and nephrosis | |
| Neurofibromatosis, type 1 | NF-1 |
| Neuronal ceroid lipofuscinoses-related diseases | |
| Neutropenia | G-CSF |
| Niemann Pick disease, type A/B | SMPD1 |
| Niemann Pick disease, type C | NPC1 |
| Niemann-Pick disease Type C1 | |
| Nocturia | |
| Non-alcoholic fatty liver disease | |
| Non-Hodgkin lymphoma | Anti-CD20 mAb |
| Non-small cell lung cancer | |
| Notch-3 related cerebral autosomal dominant arteriopathy with subcortical infarcts and leukoencephalopathy (CADASIL) | |
| Obesity | |
| Ophthalmoparesis | |
| Opioid induced constipation | |
| Ornithine transcarbamylase deficiency | Ornithine transcarbamylase |
| Osteoarthritis | |
| Osteopetrosis | |
| Osteoporosis | Anti-RANKL mAb |
| Ovarian cancer | |
| Paget disease of bone | Sequestosome 1 |
| Pain | |
| Pancreatic carcinoma | |
| Panic disorder | |
| Parkinson disease | |
| Paroxysmal nocturnal hemoglobinuria | Anti-complement factor C5 Mab |
| *Pediculosis capitis* (head lice) | |
| Pelizaeus-Merzbacher disease | |
| Pemphigus vulgaris | |
| Peptic ulcer disease | |
| Peripheral neuropathy | |
| Peyronie's disease | |
| Phenylketonuria | Phenylalanine hydroxylase |
| Pneumococcal infection prophylaxis | |
| POLG-related sensory ataxic neuropathy | |
| Polycystic kidney disease | |
| Polycystic ovary syndrome | |
| Polycythaemia vera | |
| Polymerase G-related disorders | |
| Polymorphous light eruption | |

TABLE 4-continued

Exemplary Indications and Related Proteins

| Indication | Therapeutic Protein |
|---|---|
| Pompe disease | Alpha glucosidase |
| Porphyria cutanea tarda | Uroporphyrinogen decarboxylase |
| Post herpetic neuralgia | |
| Post-organ transplant | |
| Pouchitis | |
| PPM-X Syndrome | |
| Prader-Willi syndrome | |
| Preeclampsia | |
| Premature ejaculation | |
| Prematurity and low birth weight | |
| Primary ciliary dyskinesia | |
| Primary glomerular diseases | |
| Primary humoral immune deficiencies (e.g., CVID) | Immunoglobulin |
| Proctitis | |
| Progressive multifocal leukoencephalopathy | |
| Progressive supranuclear palsy | |
| Propionic acidemia | Propionyl-CoA carboxylase |
| Prostate cancer | |
| Psoriasis | Anti-IL-12 & IL-23 mAb |
| Psoriatic arthritis | TNF-alpha inhibitors |
| PTT-1 | |
| Pulmonary arterial hypertension | |
| Pulmonary arterial hypertension | |
| Raynaud's phenomenon | |
| Refractive errors | |
| Renal cell carcinoma | |
| Restless leg syndrome | |
| Retinitis pigmentosa | |
| Rheumatic heart disease | |
| Rheumatoid arthritis | Anti-interleukin-6 (IL-6) mAb |
| Rheumatoid arthritis | T-cell costimulation blocker |
| Rheumatoid arthritis | TNF-alpha inhibitor |
| Romano-Ward syndrome | |
| Rosacea | |
| Sanfilippo syndrome, type A (MPS IIIA) | Heparan N-sulfatase |
| Sanfilippo syndrome, type B (MPS IIIB) | N-acetyl-alpha-D-glucosaminidase |
| Santavuori-Haltia disease | |
| Schizophrenia | |
| Schnitzler syndrome | |
| Scleroderma | |
| SCN1A | |
| SCN1B-related seizure disorders | |
| Short-chain acyl-CoA dehydrogenase deficiency | Butyryl-CoA dehydrogenase |
| Sickle cell disease | Hemoglobin |
| SLC3A1-related disorders | |
| Small cell lung cancer | |
| SMN-1-related spinal muscular atrophy (SMA) | |
| Spinal muscular atrophy | Survival motor neuron protein |
| Squamous cell carcinoma of head and neck | |
| Stickler syndrome | |
| Stomach cancer | |
| Stroke prophylaxis | |
| Synovial sarcoma | |
| Systemic lupus erythematosus | Anti-BAFF |
| Systemic sclerosis | |
| Tetrahydrobiopterin-deficient hyperphenylalaninemia | Tetrahydrobiopterin |
| Thromboangiitis obliterans | |
| Thrombotic disorders | |
| Thyroid cancer | |
| TPP1 deficiencies | |
| Trachea, bronchus, lung cancers | |
| Tricuspid atresia | |
| TSC1 | |
| TSC2-related tuberous sclerosis | |
| Type 2 diabetes mellitus | Glucagon-like peptide 1 (GLP-1) agonist |
| Type 2 diabetes mellitus | Insulin |
| Tyrosinemia, type I | Fumarylacetoacetase |
| Ulcerative colitis | |
| Uterine fibroids | |
| Varicose veins | |
| Venous thromboembolism | |

TABLE 4-continued

Exemplary Indications and Related Proteins

| Indication | Therapeutic Protein |
|---|---|
| Very long-chain acyl-CoA dehydrogenase deficiency | Long-chain-acyl-CoA dehydrogenase |
| von Gierke's disease | Glucose-6-phosphatase |
| Von Hippel-Lindau disease | pVHL |
| Wegener granulomatosis | |
| Wilson disease | Wilson disease protein |
| X-Linked adrenal hypoplasia | |
| X-linked adrenoleukodystrophy | |
| X-linked agammaglobulinemia | Bruton's tyrosine kinase |

In some embodiments, the present invention is used to prevent, treat and/or cure a subject affected with a disease or disorder listed or associated with the proteins listed in Tables 1, 2, 3, or 4. In some embodiments, an mRNA encodes one or more of Cystic Fibrosis Transmembrane Conductance Regulator (CFTR), argininosuccinate synthetase (ASS1), Factor IX, survival motor neuron 1 (SMN1), or phenylalanine hydroxylase (PAH). In some embodiments, one or more of a RNAi nucleic acid, gRNA and crRNA bind to endogenous nucleic acid, such as RNA or DNA, to modulate one or more of Cystic Fibrosis Transmembrane Conductance Regulator (CFTR) protein, argininosuccinate synthetase (ASS1) protein, Factor IX, survival motor neuron 1 (SMN1) protein, phenylalanine hydroxylase (PAH) or a protein or gene that modulates such proteins.

EXAMPLES

Example 1. Synthesis of Thioacetate Starting Material (Scheme 8)

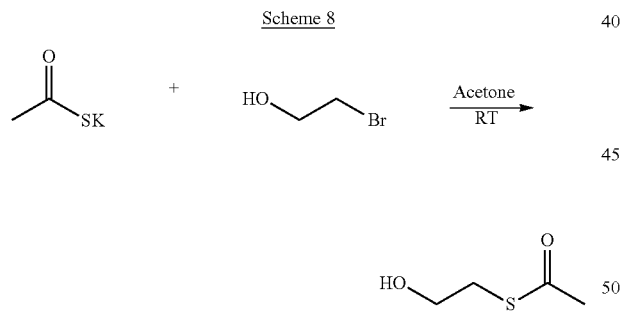

In a typical procedure, 25 g of potassium thioacetate is dissolved in 200 mL of ACS grade acetone and cooled in an ice bath. To this, 27.4 g of 2-bromoethanol is added to the cooled solution (the container is then rinsed with ~50 mL of acetone to ensure maximum transfer). The reaction is stirred for 24 hours, allowing the bath to come to room temperature. The solution is then filtered by gravity before removing the solvent by rotovap to give crude yellow oil. The resulting oil is dissolved in 500 mL of DCM, washed twice with 200 mL of water and dried over sodium sulfate before decanting and evaporating to give crude product (75-85% yield). The product is then purified by column chromatography (EtOAc: Heptane). $^1$H NMR: 2.37 ppm (s, 3H); 2.64 ppm (broad —OH, 1H); 3.08 ppm (t, 2H); 3.75 ppm (t, 2H).

Example 2. Production of Cyclophospholane Precursor

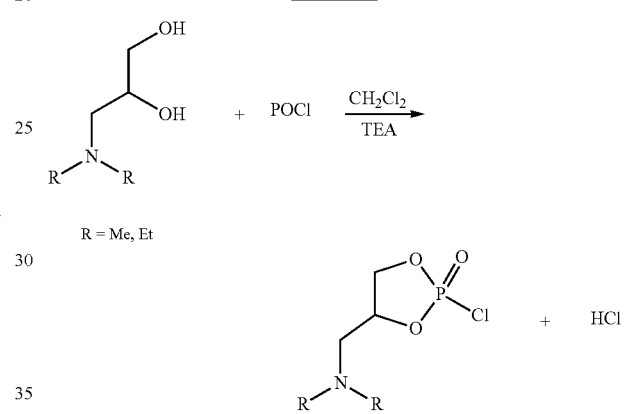

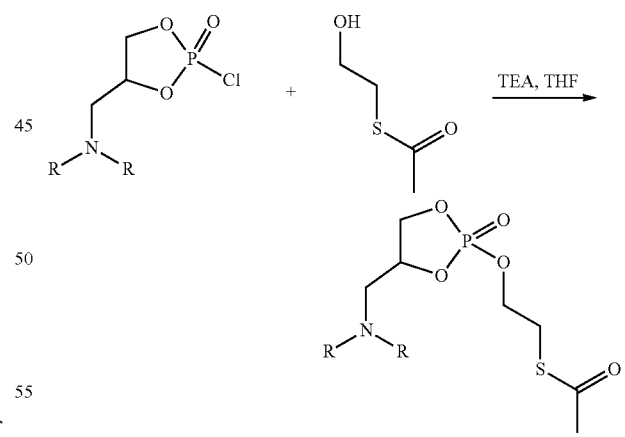

Phosphoryl trichloride and TEA were dissolved in 30 mL of DCM and cooled to −35° C. (IPA/CO$_2$ bath). The diol was added slowly keeping the temp below −20° C. and the product was brought to room temperature and mixed for at least 1 hour. The solution was cooled again in IPA/CO$_2$. A TEA/thioester mixture in 3 volumes of DCM was added to the reaction slowly, keeping the temperature below −20° C. The solution was then allowed to come to room temperature while mixing overnight The solution was filtered the filtrate was then concentrated by rotovap. The resulting oil was dissolved in DCM and rinsed with bicarbonate/water. The organic layer was dried by MgSO$_4$, filtered and concentrated to give quantitative crude yield. $^1$H NMR consistent with expected structure.

Example 3. Production of Poly(Phosphoester) Using Ring-Opening Polymerization (ROP)

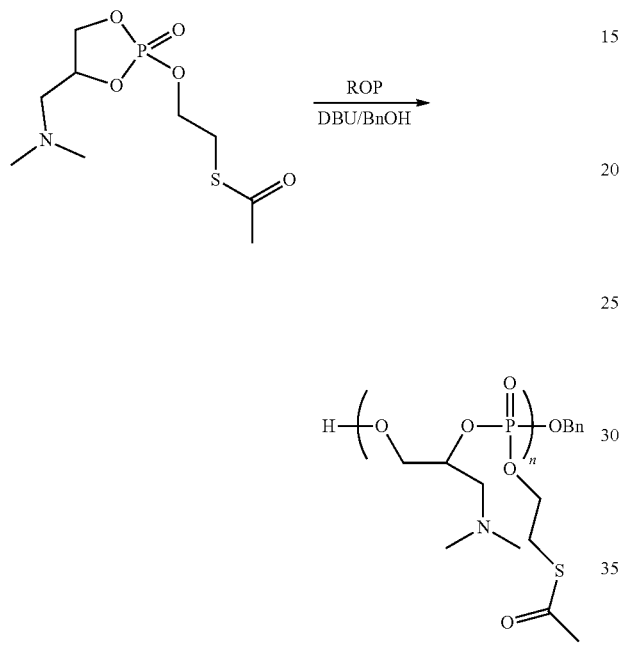

Scheme 10

In a 50 mL round bottom flask, 2 g of monomer were charged into 20 mL of anhydrous toluene and 7.6 mg of benzyl alcohol. The mixture was stirred for 15 minutes under nitrogen and 13.4 mg of DBU was added via syringe and allowed to stir for 24 hours. After this time, the reaction was quenched with excess acetic acid. The resulting polymer was precipitated with 20 volumes of diethyl ether to give 20% yield of polymer with Mw of 900 Da.

Example 4. Production of Poly(Phosphoester) Using Ring-Opening Polymerization (ROP) as a One-Pot Reaction Using Pendant Amine Scheme 11

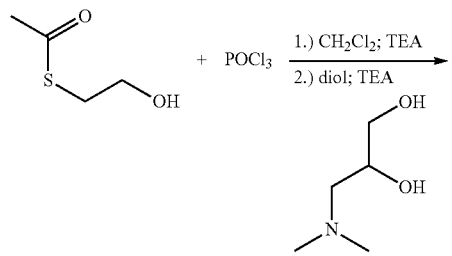

-continued

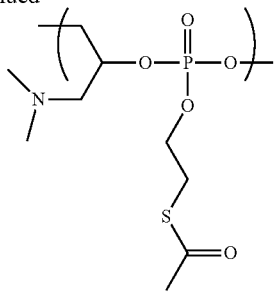

A 100 mL round bottom flask was charged with 25 mL of DCM and sealed under positive nitrogen pressure before adding 2 g of POCl$_3$. The reaction mixture was cooled in IPA/CO$_2$ bath for 30 minutes before adding premixed thio-ester/DCM/TEA solution (1.6 g/5 mL/1.4 g, respectively) slowly, never letting the solution rise above −20° C. After addition, stirring was continued and the reaction mixture was brought to room temperature for at least 1 hour. The solution was cooled in IPA/CO$_2$ bath for at least 30 minutes and a premix of diol/DCM/TEA solution (1.57 g/3 mL/2.6 g respectively) was added slowly. The reaction stirred for up to 72 hours at room temperature. Upon completion, the reaction was filtered and the filtered solution was then added to 10 volumes of MTBE slowly with constant stirring. The solids were removed by filtration and the filtrate was concentrated under reduced pressure. The concentrated solution was precipitated in 20 volumes of cold THF and decanted. The product was re-dissolved in MeOH (5 volumes) and precipitated into THF again. The product was filtered, and dried under vacuum to constant mass (0.5 g, 10% yield).

Example 5. Production of Poly(Phosphoester) Using Ring-Opening Polymerization (ROP) as a One-Pot Reaction Using Amine within Polymer Backbone Scheme 12.

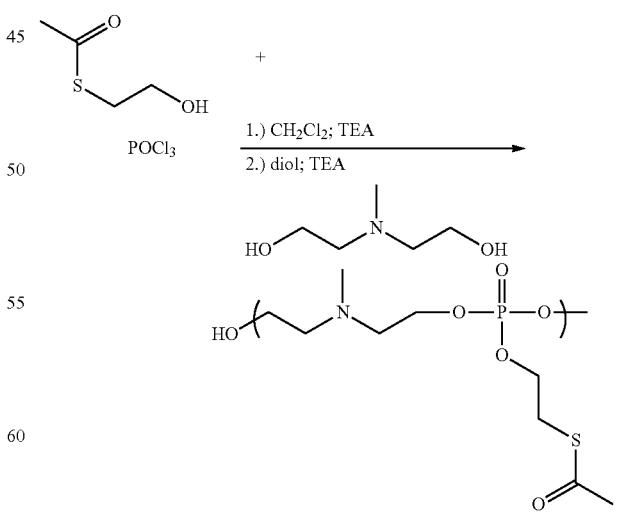

A 100 mL round bottom flask was charged with 25 mL of DCM and sealed under positive nitrogen pressure before adding 2 g POCl$_3$. The reaction mixture was cooled in IPA/CO$_2$ bath for 30 minutes before adding the premixed thioester/DCM/TEA solution (1.6 g/5 mL/1.4 g, respectively) slowly, never letting the solution rise above −20° C. After addition, stirring was continued and the reaction mixture was brought to room temperature for at least 1 hour. After this time, the solution was cooled in IPA/CO$_2$ bath for at least 30 minutes and premixed diol/DCM/TEA solution (1.57 g/3 mL/2.6 g respectively) was added slowly. The reaction stirred for up to 72 hours at room temperature and was then filtered. The filtered solution was then added to 10 volumes of MTBE slowly with constant stirring and the resulting solids were removed by filtration. The filtrate was concentrated under reduced pressure. The resulting concentrated solution precipitated in 20 volumes of cold THF. The THF was decanted and the product was dissolved in MeOH (5 volumes) and precipitated into THF again. After decantation, the solid was dried under vacuum to constant mass (1.2 g 22% yield).

Example 6. Synthesis of Dinitrophenol Thioacetate Phosphate Precursor Starting Material (One-Pot Example)

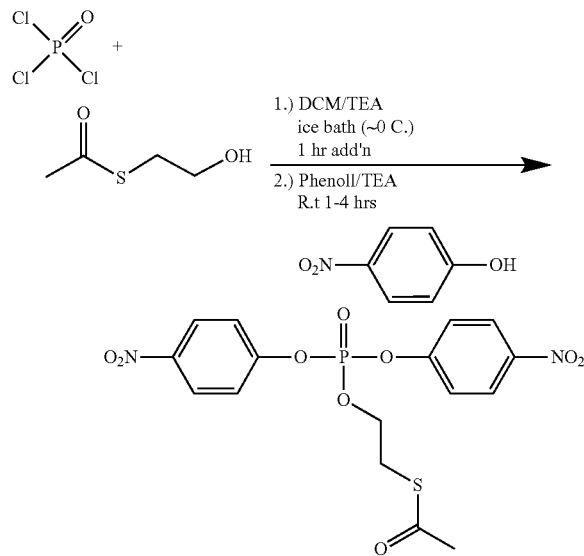

A 100 mL round bottom flask was charged with 75 mL of DCM and 3 g of POCl$_3$ and sealed under positive nitrogen pressure. The reaction mixture was cooled in an ice bath for 30 minutes before slowly adding a premixed thioester/DCM/TEA solution (2.44 g/10 mL/1.8 g, respectively) slowly, never letting the solution rise above 20° C. After addition, stirring was continued while the reaction mixture was brought to room temperature for at least 1 hour. After this time, the solution was cooled in ice bath for at least 30 minutes. Upon cooling, a premixed phenol/DCM/TEA solution (5.7 g/10 mL/4 g respectively) was slowly over the course of an hour and the reaction was stirred for up to 72 hours at ambient temperature. Upon completion, the reaction was filtered and the filtrate was concentrated under reduced pressure. The resulting crude material was purified by silica gel chromatography with DCM/MeOH mixture (56% yield).

Example 7. Synthesis of Dinitrophenol Chlorophosphate Starting Material

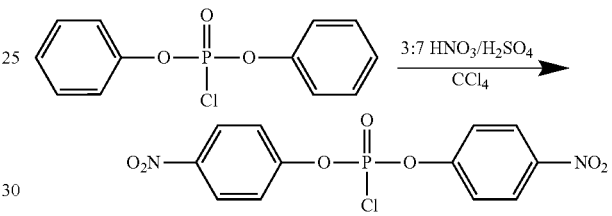

In a glove bag, 16 g bisphenol phosphoryl chloride was charged to 100 mL round bottom flask. 25 mL of carbon tetrachloride was add to the flask and the solution mixed to dissolve the solid. The sealed vessel was transferred to a cooled in an ice bath for 30 minutes under N$_2$ and stirring was performed. 20 mL of a 3:7 HNO$_3$:H$_2$SO$_4$ solution was added slowly through a drop funnel over 1 hour and allowed to stir overnight (16 hours). After this time, the reaction was washed with 200 mL of DCM, and the organic layer was separated and quenched with anhydrous sodium carbonate under N$_2$. The solution was then filtered and the solvent evaporated to a constant mass. The product was used as-is in subsequent reactions (21 g crude, quantitative). $^1$H NMR consistent with expected structure.

Example 8. Alternate Synthesis of Dinitrophenol Thioacetate Precursor

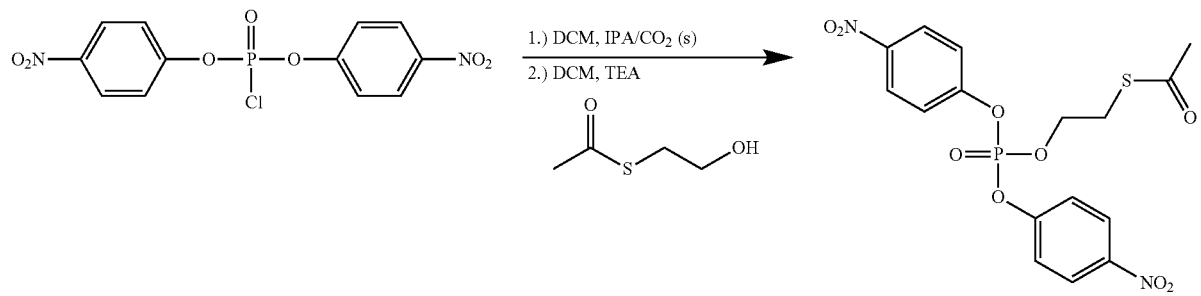

A 250 mL round bottom flask was charged with 10 g of dinitrophenol chlorophosphate with 100 mL of DCM under $N_2$. The reaction mixture was cooled in an $IPA/CO_2$ bath and mixed until a homogenous solution was achieved. Slow addition of a premixed thioester/DCM/TEA solution (2.1 g/10 mL/2.2 g) to the reaction vessel performed and mixed slowly over and hour. The reaction was brought to room temperature while stirring under $N_2$ overnight. After this time, the reaction solution was evaporated and the residue was dissolved in 100 mL of carbon tetrachloride, filtered, and evaporated again to a constant mass (6.5 g, 80% yield). NMR was consistent with desired product.

Example 9. Alternate Production of Poly(Phosphoester)

Scheme 16.

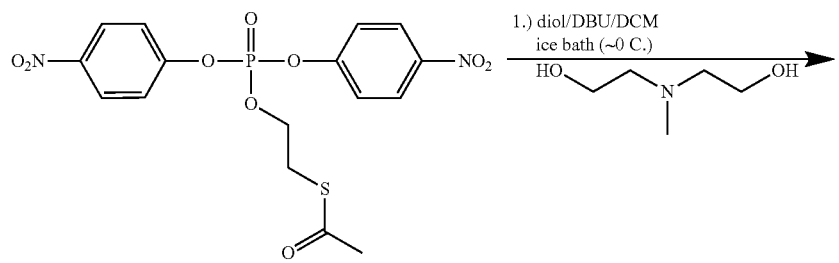

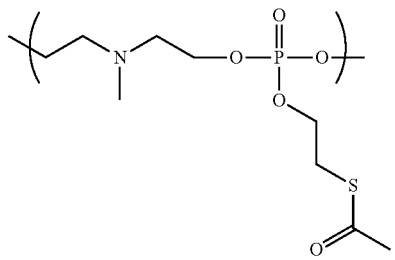

A 100 mL round bottom flask was charged with 25 mL of DCM and sealed under positive nitrogen pressure before adding 2 g $POCl_3$. The reaction mixture was cooled in $IPA/CO_2$ bath for 30 minutes before adding premixed thioester/DCM/TEA solution (1.6 g/5 mL/1.4 g, respectively) slowly, never letting the solution rise above −20° C. After addition of the mixture, stirring was continued and the reaction mixture was brought to room temperature for at least 1 hour. The solution as cooled solution in $IPA/CO_2$ bath for at least 30 minutes. Upon cooling, a premixed diol/DCM/TEA solution (1.57 g/3 mL/2.6 g respectively) was added and the resulting mixture was stirred for up to 72 hours at room temperature. After a given time, the reaction was filtered and the filtrate was added to 10 volumes of MTBE slowly with constant stirring. The resulting solids were removed by filtration and the filtrate was concentrated under reduced pressure. The concentrated solution was precipitated in 20 volumes of cold THF and the solvent was decanted. The product was re-dissolved in MeOH (5 volumes) and precipitated into THF again. The THF was decanted and the product was dried under vacuum to constant mass (0.4 g, 32% yield).

Example 10. Alternate Production of Poly(Phosphoester)

Scheme 17.

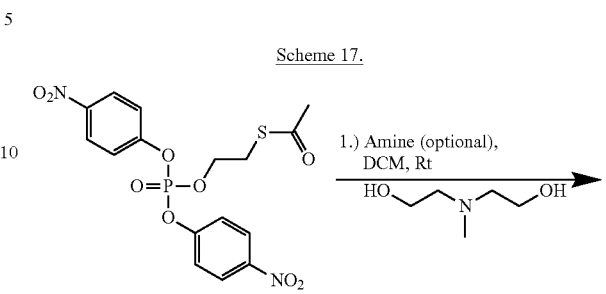

-continued

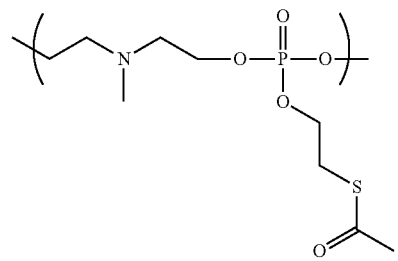

TABLE A

| Reaction # | Monomer | Amine | Conditions | MW | Notes |
|---|---|---|---|---|---|
| 074 | 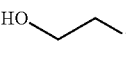 N-methyldiethanolamine | TEA | DCM | 12.8 kDa | Dialyzed |
| 079A | 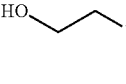 N-methyldiethanolamine | TEA | DCM | 24 kDa | Dialyzed |
| 079B | 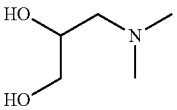 3-dimethylamino-1,2-propanediol | Polymer-bound scavenger (resin) | DCM | 24 kDa | Dialyzed |
| 086 | 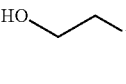 N-methyldiethanolamine | Polymer-bound scavenger (resin) | DCM | 21 kDa | Dilute in MeOH (filter), Remove and recrystallize in THF |
| 087A | 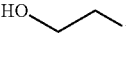 N-methyldiethanolamine | TEA | DCM | 45 kDa | MTBE precipitation (filter), MeOH/THF recrystallization |
| 087B | 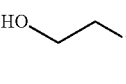 N-methyldiethanolamine | TEA | DCM | 32 kDa | Acidify reaction mixture, Toluene addition (oil out) MeOH/THF recrystallization |
| 088 | 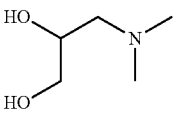 3-dimethylamino-1,2-propanediol | TEA | DCM | 69 kDa | MeOH/Brine THF Precipitation |
| 089 | 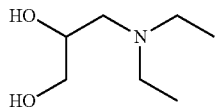 3-diethylamino-1,2-propanediol | TEA | DCM | 24 kDa | MeOH/Brine THF extracted |
| 090 | 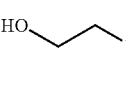 N-methyldiethanolamine | TEA | DCM | 7 kDa | MeOH/EtOAc recrystallization |

Example 11. Synthesis of Branched Poly(Phosphoester)

Scheme 18. Reaction for branched poly(phosphoester) polymer

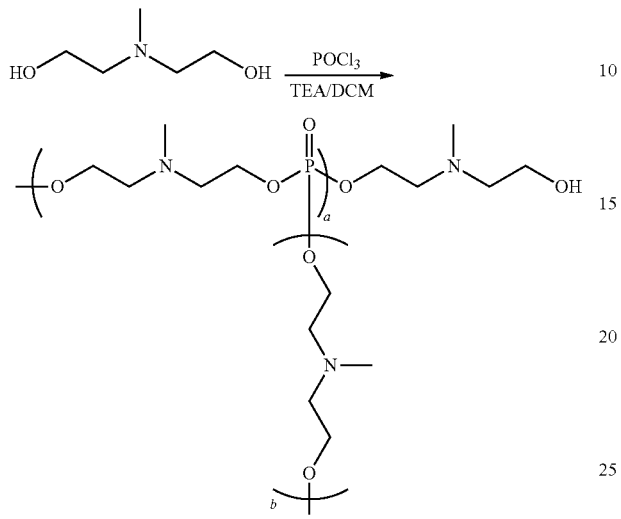

POCl₃ was dissolved in dichloromethane (5 mL) in a 100 mL round bottom flask. The solution was cooled with IPA/CO2 before adding the diol/TEA/DCM solution slowly. The reaction solution was stirred for 72 hours, quenched with MeOH/ACN and the solvent was removed under reduced pressure to dryness yielding a crude yellow material. A portion of the material was dissolved and dialyzed against a 50/50 MeOH/phosphate buffer solution for 24 hours resulting in a polymer with an approximate molecular weight of 27 kDa.

Synthesis of Alternative Imidazole-Based Diol Monomers.

Exemplary imidazole-based diols are provided in Scheme 19.

Scheme 19

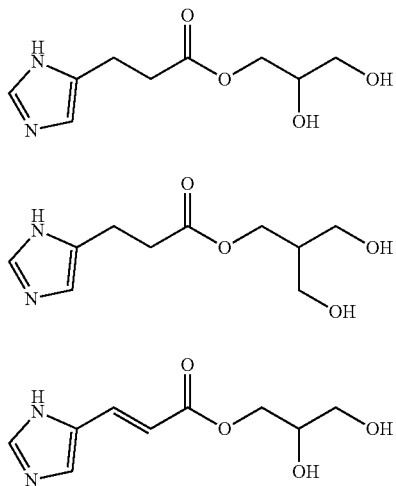

301

302

303

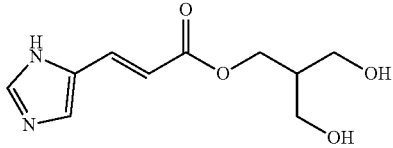

304

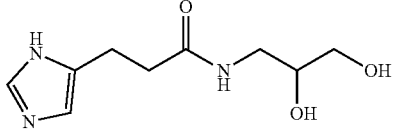

305

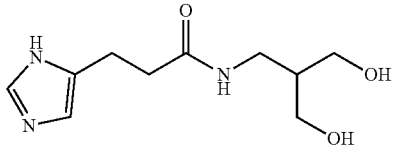

306

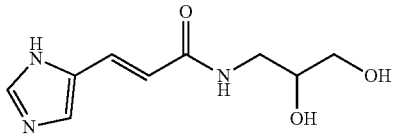

307

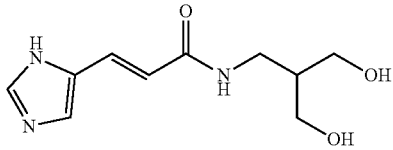

308

Scheme 20 describes an exemplary synthesis of diol monomer 301.

Scheme 20

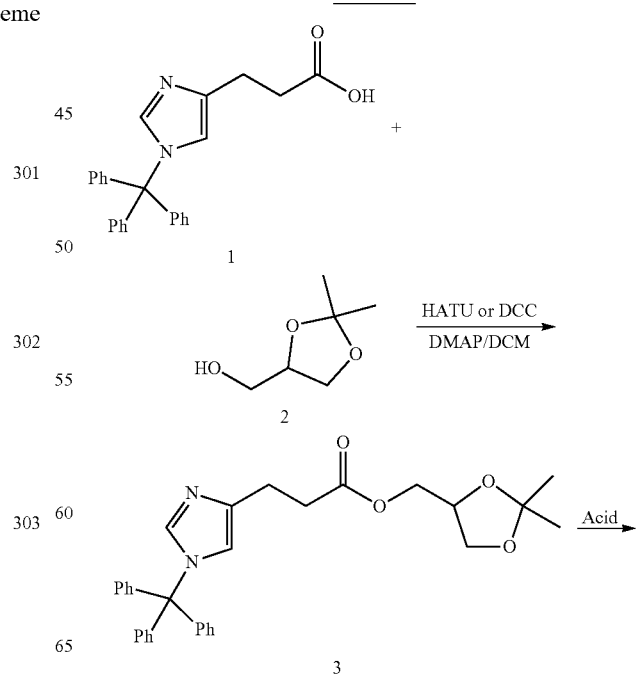

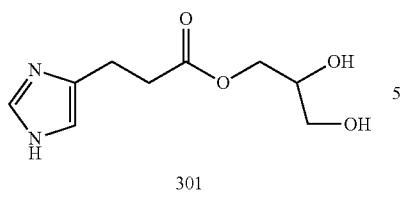
Scheme 21 describes an exemplary synthesis of diol monomer 302.
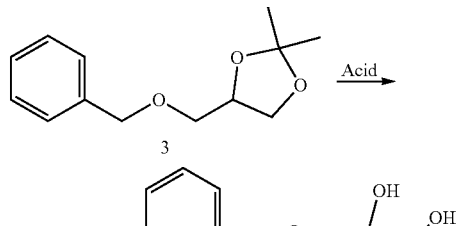
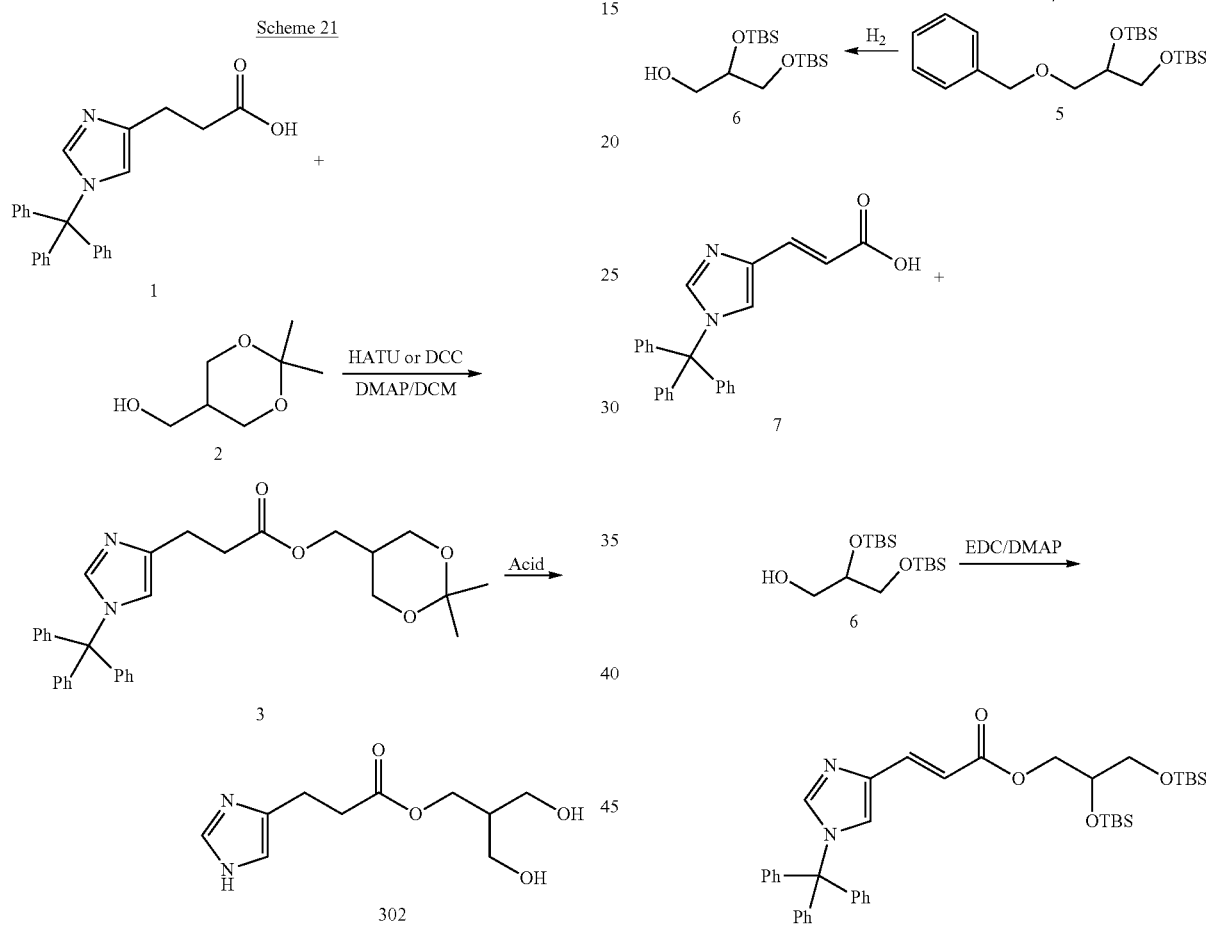
Scheme 22 describes an exemplary synthesis of diol monomer 303.
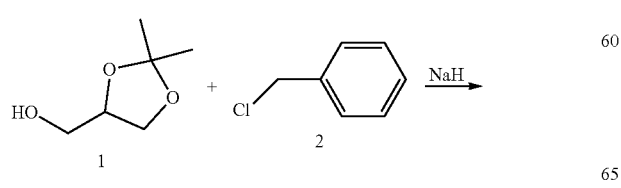
Scheme 23 describes an exemplary synthesis of diol monomer 304.

Scheme 23

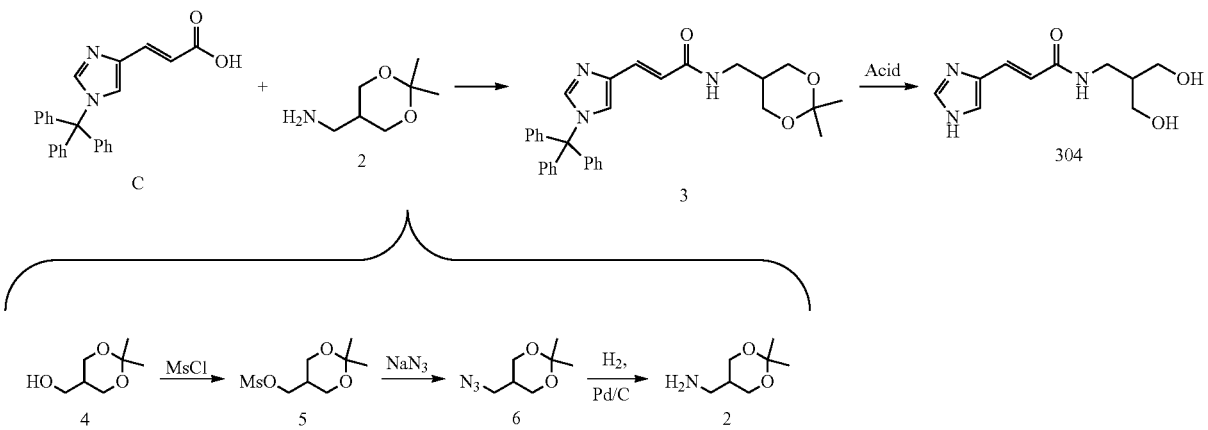

Example 12. Synthesis of Diol Monomer 305

Scheme 24 describes an exemplary synthesis of diol monomer 305.

Scheme 24

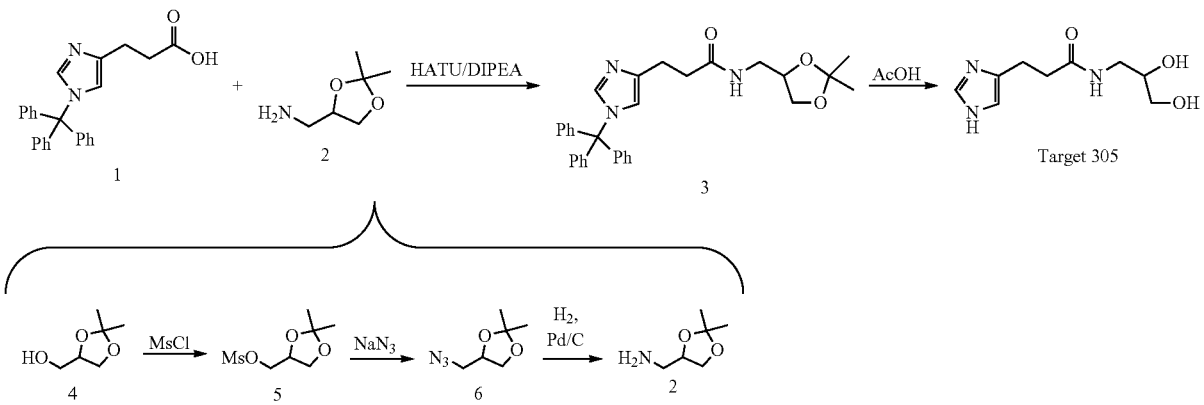

N-((2,2-dimethyl-1,3-dioxolan-4-yl)methyl)-3-(1-trityl-1H-imidazol-4-yl)propanamide (3)

To the mixture of 3-(1-trityl-1H-imidazol-4-yl)propanoic acid (1) (10.2 g, 0.027 mol, 1.0 equiv) and HATU (10.2 g, 0.027 mol, 1.0 equiv) in DCM (200 mL) was added DIPEA (14 mL, 3.0 equiv), the resulting mixture was stirred 5 min. at room temperature, and then (2,2-dimethyl-1,3-dioxolan-4-yl)methanamine (2) (3.5 g, 0.027 mol, 1.0 equiv) was added. The mixture was stirred overnight at room temperature. The reaction mixture was washed with Brine (100 mL×3), and dried with anhydrous sodium sulfate. After the filtration, the organic solvent was evaporated under vacuum and the residue was purified with an ISCO (330 g column), eluted with 0-100% MeOH in DCM, collected 13 g (98%) of the desired product 3.

(2,2-dimethyl-1,3-dioxolan-4-yl)methyl methanesulfonate (5)

To the solution of (2,2-dimethyl-1,3-dioxolan-4-yl)methanol (4) (25 g, 0.18 mol) in DCM (100 mL) was added TEA (30 mL, 0.32 mol) followed by the addition of MSCl (16.3 mL, 0.15 mol) with ice bath cooling. The resulting mixture was stirred for 2 h. at room temperature. The reaction mixture was then washed with cold water (100 mL×3), dried with anhydrous magnesium sulfate. After filtration, the organic solvent was evaporated under vacuum and collected 37.2 g of crude product (5) that was used for the next step without further purification.

4-(azidomethyl)-2,2-dimethyl-1,3-dioxolane (6)

To the solution of (2,2-dimethyl-1,3-dioxolan-4-yl) methyl methanesulfonate (7) (37.2 g, 0.18 mol) in DMF (100 mL) was added a solution of $NaN_3$ (16 g, 0.24 mol, 1.3 equiv) in water (100 mL). The resulting mixture was heated overnight at 80-90° C. After the reaction was cooled to room temperature, brine (400 mL) was added. Ether was used to extract (200 mL×4), the combined ether was washed with brine (200 mL×2) and water (200 mL×2), dried with anhydrous sodium sulfate. After the filtration, the organic solvent was evaporated under vacuum and collected 21.7 g of crude product (6) that was used for the next step without further purification

(2,2-dimethyl-1,3-dioxolan-4-yl)methanamine (2)

To the solution 4-(azidomethyl)-2,2-dimethyl-1,3-dioxolane (6) (20 g) in MeOH (200 mL), Pd/C (10%, 5 g) was added, the resulting mixture was purged with $H_2$ three times and stirred under $H_2$ balloon overnight. The reaction mixture was passed through a Celite pad, washed with methanol. The filtrate was concentrated and purified with an ISCO (330 g column, eluted with 0-10% MeOH in DCM, collected 5.8 g (17%) desired product 2.

N-(2,3-dihydroxypropyl)-3-(1H-imidazol-4-yl)propanamide (Target 305)

To the solution of N-((2,2-dimethyl-1,3-dioxolan-4-yl)methyl)-3-(1-trityl-1H-imidazol-4-yl)propanamide (3) (13 g) in DCM (25 mL) and MeOH (25 mL) was added AcOH (100 mL). The resulting reaction mixture was heated overnight at 70-80° C. The reaction solution was cooled to room temperature and concentrated under vacuum. MeOH (50 mL) was added into the residue, the pH was adjusted to 9-10 with 2M NaOH aqueous solution. After the filtration, the filtrate was purified with an ISCO, 330 g C-18 column, eluted with 0-100% MeOH/$H_2O$, collected 2.5 g (44%) of pure desired product (Target 305.)

Example 13. Synthesis of Diol Monomer 306

Scheme 25 describes an exemplary synthesis of diol monomer 306.

residue was purified with ISCO (330 column), eluted with 0-100% MeOH in DCM, collected 17.6 g (88%) desired product 3.

N-(3-hydroxy-2-(hydroxymethyl)propyl)-3-(1H-imidazol-4-yl)propanamide (Target 306)

To the solution of N-((2,2-dimethyl-1,3-dioxan-5-yl)methyl)-3-(1-trityl-1H-imidazol-4-yl)propanamide (3) (17.6 g) in DCM (50 mL) and MeOH (50 mL) was added AcOH (100 mL). The resulting reaction mixture was heated overnight at 70-80° C. The reaction solution was cooled to room temperature and concentrated under vacuum. MeOH (50 mL) was added into the residue, the pH was adjusted to 9-10 with 2M NaOH aqueous solution. After the filtration, the filtrate was purified with ISCO, 330 g C-18 column, eluted with 0-100% MeOH/$H_2O$, collected 4.4 g (56%) pure desired product (Target 306.)

Example 14. Synthesis of Diol Monomer 307

Scheme 26 describes an exemplary synthesis of diol monomer 307.

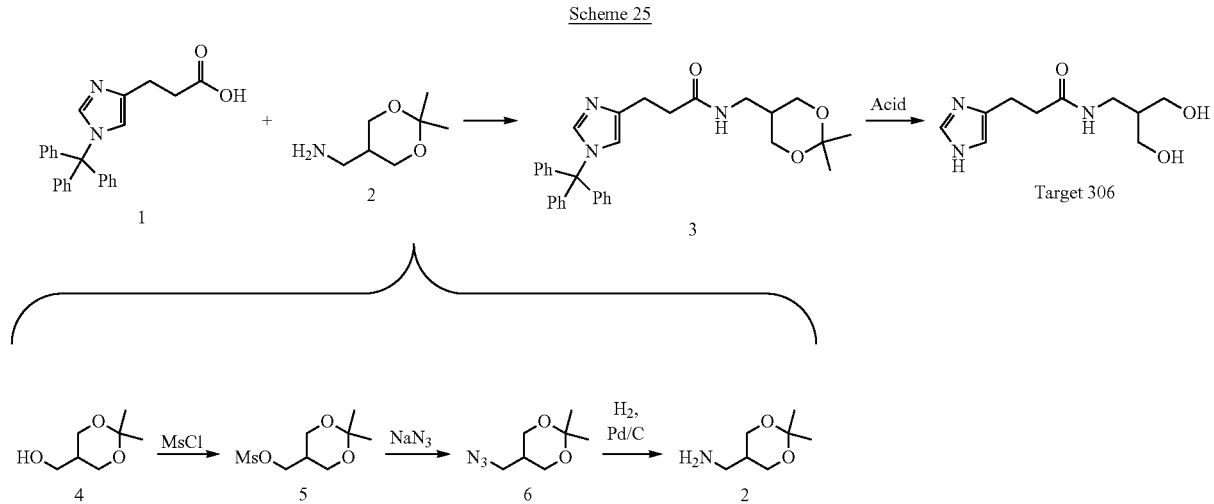

N-((2,2-dimethyl-1,3-dioxan-5-yl)methyl)-3-(1-trityl-1H-imidazol-4-yl)propanamide (3)

To the mixture of 3-(1-trityl-1H-imidazol-4-yl)propanoic acid (1) (15 g, 0.039 mol, 1.0 equiv) and HATU (15 g, 0.039 mol, 1.0 equiv) in DCM (400 mL), DIPEA (20 mL, 3.0 equiv) was added, the resulting mixture was stirred 5 min. at room temperature, and (2,2-dimethyl-1,3-dioxan-5-yl)methanamine (4) (5.7 g, 0.039 mol, 1.0 equiv) was added. The resulting mixture was stirred overnight at room temperature. The reaction mixture was washed with Brine (100 mL×3), and dried with anhydrous sodium sulfate. After the filtration, the organic solvent was evaporated under vacuum and the

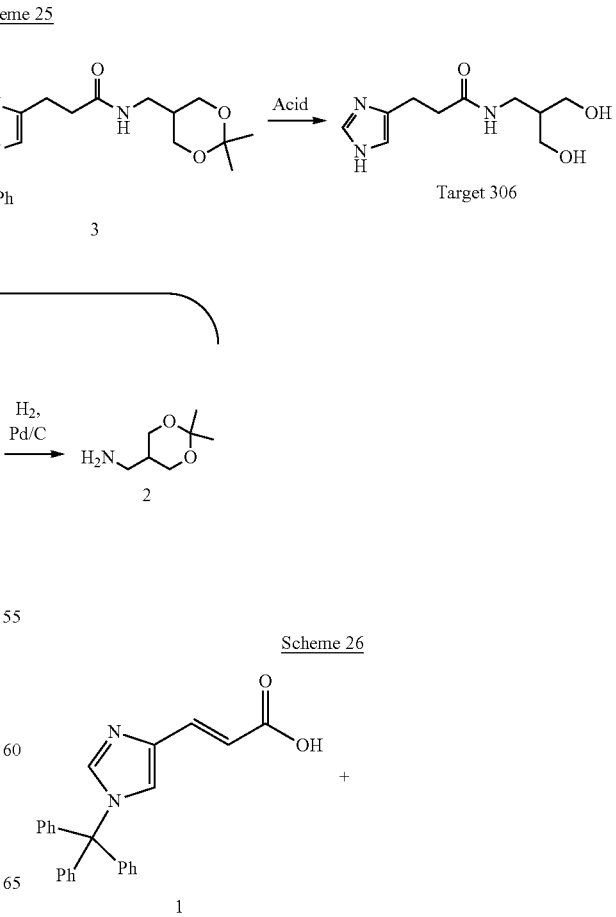

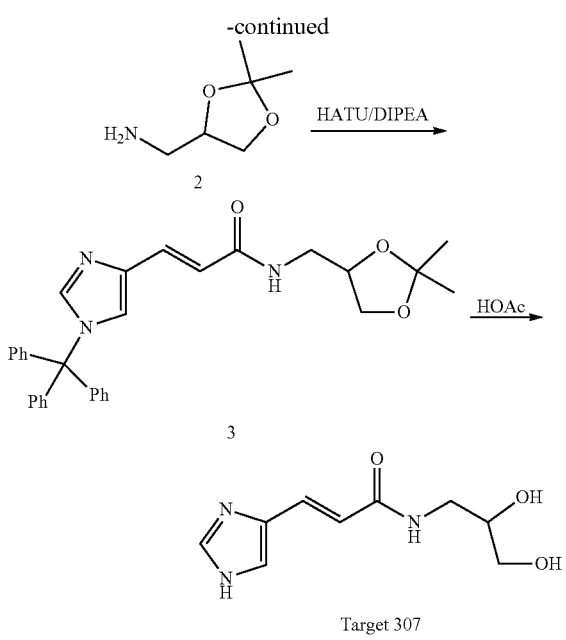

(E)-N-((2,2-dimethyl-1,3-dioxolan-4-yl)methyl)-3-(1-trityl-1H-imidazol-4-yl)acrylamide (3)

To the mixture of (E)-3-(1-trityl-1H-imidazol-4-yl)acrylic acid (1) (14.5 g, 0.038 mol, 1.0 equiv) and HATU (14.5 g, 0.038 mol, 1.0 equiv) in DCM (400 mL), DIPEA (19.6 mL, 3.0 equiv) was added, the resulting mixture was stirred 5 min. at room temperature, and (2,2-dimethyl-1,3-dioxan-5-yl)methanamine (4) (5.0 g, 0.038 mol, 1.0 equiv) was added. The resulting mixture was stirred overnight at room temperature. The reaction mixture was washed with Brine (100 mL×3), and dried with anhydrous sodium sulfate. After filtration the organic solvent was evaporated under vacuum and the residue was purified with ISCO (330 g column), eluted with 0-100% MeOH in DCM, collected 17.1 g (90%) desired product 5.

(E)-N-(2,3-dihydroxypropyl)-3-(1H-imidazol-4-yl)acrylamide (Target 307)

To the solution of (E)-N-((2,2-dimethyl-1,3-dioxolan-4-yl)methyl)-3-(1-trityl-1H-imidazol-4-yl)acrylamide (3) (17.1 g) in DCM (50 mL) and MeOH (50 mL) was added AcOH (100 mL). The resulting reaction mixture was heated overnight at 70-80° C. The reaction solution was cooled to room temperature and concentrated under vacuum. MeOH (50 mL) was added into the residue, the pH was adjusted to 9-10 with 2M NaOH aqueous solution. After filtration the filtrate was purified with an ISCO, 330 g C-18 column, eluted with 0-100% MeOH/$H_2O$, collected 2.0 g (27%) pure desired product (Target 307.)

Example 15. Synthesis of Diol Monomer 308

Scheme 27 describes an exemplary synthesis of diol monomer 308.

Scheme 27

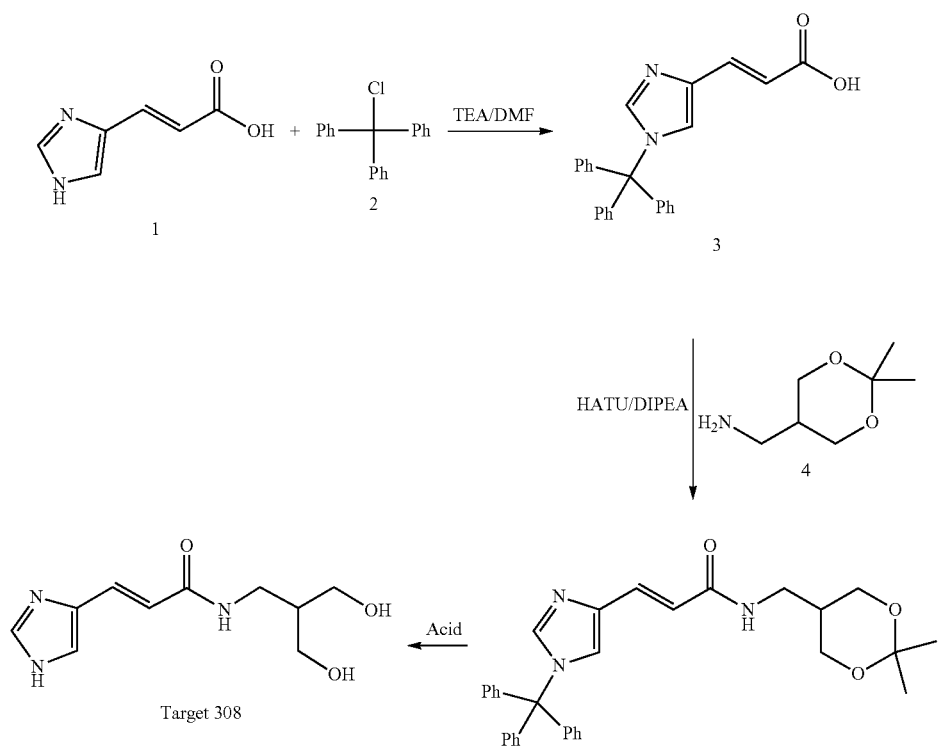

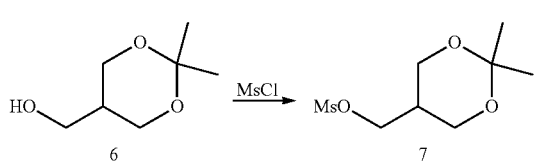 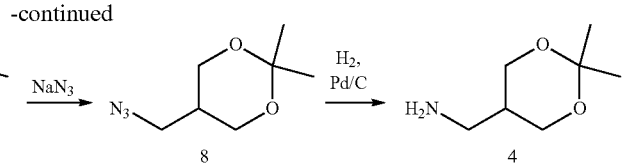

Synthesis of (E)-3-(1-trityl-1H-imidazol-4-yl)acrylic Acid (3)

To the mixture of urocanic acid (1) (21.3 g, 0.154 mol, 1.0 equiv) and trityl chloride (2) (43 g, 0.154 mol, 1.0 equiv) in anhydrous DMF (350 mL) was added TEA (64.8 mL, 0.462 mol, 3.0 equiv). The mixture was stirred overnight at room temperature. CHCl$_3$ (500 mL) was added and the solution washed with Brine. The aqueous was further extracted with DCM and the combined organic phases were combined and dried over anhydrous sodium sulfate. After filtration the organic solvent was evaporated under vacuum and the residue was purified with an ISCO (330 column), eluted with 0-15% MeOH in DCM, collected 28.4 g (48%) of the desired product 3.

(E)-N-((2,2-dimethyl-1,3-dioxan-5-yl)methyl)-3-(1-trityl-1H-imidazol-4-yl)acrylamide (5)

To the mixture of (E)-3-(1-trityl-1H-imidazol-4-yl)acrylic acid (3) (15 g, 0.039 mol, 1.0 equiv) and HATU (15 g, 0.039 mol, 1.0 equiv) in DCM (400 mL), was added DIPEA (20 mL, 3.0 equiv) and the resulting mixture was stirred 5 min. at room temperature and then (2,2-dimethyl-1,3-dioxan-5-yl)methanamine (4) (5.7 g, 0.039 mol, 1.0 equiv) was added. The mixture was stirred overnight at room temperature. The reaction mixture was then washed with Brine (100 mL×3), and dried with anhydrous sodium sulfate. After the filtration, the organic solvent was evaporated under vacuum and the residue was purified with ISCO (330 column), eluted with 0-100% MeOH in DCM, collected 18.2 g (91%) of the desired product 5.

(2,2-dimethyl-1,3-dioxan-5-yl)methyl methanesulfonate (7)

To the solution of (2,2-dimethyl-1,3-dioxan-5-yl)methanol (6) (20 g, 0.137 mol, 1.0 equiv) in DCM (400 mL), was added TEA (45.4 mL, 0.32 mol, 2.3 equiv), followed by the addition of MSCl (11.7 mL, 0.15 mol) with ice bath cooling. The resulting mixture was stirred for 2 h. at room temperature. The reaction mixture was washed with cold water (100 mL×3), dried with anhydrous magnesium sulfate. After the filtration, the organic solvent was evaporated under vacuum and collected 27 g of crude product (7) that was used for the next step without further purification.

5-(azidomethyl)-2,2-dimethyl-1,3-dioxane (8)

To the solution of (2,2-dimethyl-1,3-dioxan-5-yl)methyl methanesulfonate (7) (27 g, 0.12 mol) in DMF (100 mL) was added a solution of NaN$_3$ (11.7 g, 0.18 mol, 1.5 equiv) in water (100 mL). The resulting mixture was heated overnight at 80-90° C. After the reaction was cooled to room temperature, brine (400 mL) was added. Ether was used to extract organic material (200 mL×4) and the combined ether extracts were washed with brine (200 mL×2) and water (200 mL×2) and dried with anhydrous sodium sulfate. After filtration, the organic solvent was evaporated under vacuum and collected 15.7 g of crude product (8) that was used for the next step without further purification.

(2,2-dimethyl-1,3-dioxan-5-yl)methanamine (4)

To the solution of 5-(azidomethyl)-2,2-dimethyl-1,3-dioxane (8) (15.7 g) in MeOH (200 mL) was added Pd/C (10%, 4.5 g) and the resulting mixture was purged with H$_2$ gas three times and stirred under a H$_2$ balloon overnight. The reaction mixture was passed through a Celite pad, and the pad was washed with methanol. The filtrate was concentrated and collected 11.5 g desired product 4 that was used for the next step without further purification.

(E)-N-(3-hydroxy-2-(hydroxymethyl)propyl)-3-(1H-imidazol-4-yl)acrylamide (Target 308)

To the solution of (E)-N-((2,2-dimethyl-1,3-dioxan-5-yl)methyl)-3-(1-trityl-1H-imidazol-4-yl)acrylamide (5) (18.2 g) in DCM (50 mL) and MeOH (50 mL) was added AcOH (100 mL). The resulting reaction mixture was heated overnight at 70-80° C. The reaction solution was cooled to room temperature and concentrated under vacuum. MeOH (50 mL) was added into the residue and the pH was adjusted to 9-10 with 2M NaOH aqueous solution. After filtration, the filtrate was purified with by ISCO, 330 g C-18 column, eluted with 0-100% MeOH/H$_2$O, collected 3.9 g (48%) pure desired product (Target 308.)

Examples of mRNA-Poly(Phosphoester) Nanoparticles

Example 16. Production of Human Argininosuccinate Synthetase (hASS1) Poly(Phosphoester) Nanoparticles A portion of poly(phosphoseter) 086 was dissolved in water and the pH was adjusted to 6.5. The solution was treated with a 1 mL solution of hASS1 mRNA (1 mg) and mixed resulting in a nanoparticle formation (N/P=10) with an average particle size of 89 nm.

Example 17. Production of hASS1 Poly(Phosphoester) Nanoparticles

A portion of poly(phosphoseter) 087A was dissolved in water and the pH was adjusted to 6.5. The solution was treated with a 1 mL solution of hASS1 mRNA (1 mg) and mixed resulting in a nanoparticle formation (N/P=10) with an average particle size of 92 nm. Example 21. Production of hASS1 poly(phosphoester) nanoparticles A portion of poly(phosphoseter) 087B was dissolved in water and the pH was adjusted to 6.5. The solution was treated with a 1 mL solution of hASS1 mRNA (1 mg) and mixed resulting in a nanoparticle formation (N/P=10) with an average particle size of 90 nm.

Codon-Optimized Sequence for Human Argininosuccinate Synthetase (ASS1) mRNA:

[SEQ ID NO.: 1]
XAUGAGCAGCAAGGGCAGCGUGGUGCUGGCCUACAGCGGCGGCCUGGACAC
CAGCUGCAUCCUGGUGUGGCUGAAGGAGCAGGGCUACGACGUGAUCGCCUA
CCUGGCCAACAUCGGCCAGAAGGAGGACUUCGAGGAGGCCCGCAAGAAGGC
CCUGAAGCUGGGCGCCAAGAAGGUGUUCAUCGAGGACGUGAGCCGCGAGUU
CGUGGAGGAGUUCAUCUGGCCCGCCAUCCAGAGCAGCGCCCUGUACGAGGA
CCGCUACCUGCUGGGCACCAGCCUGGCCCGCCCCUGCAUCGCCCGCAAGCA
GGUGGAGAUCGCCCAGCGCGAGGGCGCCAAGUACGUGAGCCACGGCGCCAC
CGGCAAGGGCAACGACCAGGUGCGCUUCGAGCUGAGCUGCUACAGCCUGGC
CCCCCAGAUCAAGGUGAUCGCCCCCUGGCGCAUGCCCGAGUUCUACAACCG
CUUCAAGGGCCGCAACGACCUGAUGGAGUACGCCAAGCAGCACGGCAUCCC
CAUCCCCGUGACCCCCAAGAACCCCUGGAGCAUGGACGAGAACCUGAUGCA
CAUCAGCUACGAGGCCGGCAUCCUGGAGAACCCCAAGAACCAGGCCCCCCC
CGGCCUGUACACCAAGACCCAGGACCCCGCCAAGGCCCCCAACACCCCCGA
CAUCCUGGAGAUCGAGUUCAAGAAGGGCGUGCCCGUGAAGGUGACCAACGU
GAAGGACGGCACCACCCACCAGACCAGCCUGGAGCUGUUCAUGUACCUGAA
CGAGGUGGCCGGCAAGCACGGCGUGGGCCGCAUCGACAUCGUGGAGAACCG
CUUCAUCGGCAUGAAGAGCCGCGGCAUCUACGAGACCCCCGCCGGCACCAU
CCUGUACCACGCCCACCUGGACAUCGAGGCCUUCACCAUGGACCGCGAGGU
GCGCAAGAUCAAGCAGGGCCUGGGCCUGAAGUUCGCCGAGCUGGUGUACAC
CGGCUUCUGGCACAGCCCCGAGUGCGAGUUCGUGCGCCACUGCAUCGCCAA

GAGCCAGGAGCGCGUGGAGGGCAAGGUGCAGGUGAGCGUGCUGAAGGGCCA
GGUGUACAUCCUGGGCCGCGAGAGCCCCCUGAGCCUGUACAACGAGGAGCU
GGUGAGCAUGAACGUGCAGGGCGACUACGAGCCCACCGACGCCACCGGCUU
CAUCAACAUCAACAGCCUGCGCCUGAAGGAGUACCACCGCCUGCAGAGCAA
GGUGACCGCCAAGUGAY

5' and 3' UTR Sequences
X (5' UTR Sequence) =
[SEQ ID NO.: 2]
GGACAGAUCGCCUGGAGACGCCAUCCACGCUGUUUUGACCUCCAUAGAAGA
CACCGGGACCGAUCCAGCCUCCGCGGCCGGGAACGGUGCAUUGGAACGCGG
AUUCCCCGUGCCAAGAGUGACUCACCGUCCUUGACACG Y (3' UTR Sequence) =
[SEQ ID NO.: 3]
CGGGUGGCAUCCCUGUGACCCCUCCCCAGUGCCUCUCCUGGCCCUGGAAGU
UGCCACUCCAGUGCCCACCAGCCUUGUCCUAAUAAAAUUAAGUUGCAUCAA
GCU
OR
(SEQ ID NO.: 4)
GGGUGGCAUCCCUGUGACCCCUCCCCAGUGCCUCUCCUGGCCCUGGAAGUU
GCCACUCCAGUGCCCACCAGCCUUGUCCUAAUAAAAUUAAGUUGCAUCAAA
GCU While a number of embodiments of this invention have been described, it is apparent that the basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:

1. A polymer comprising a repeating unit that is

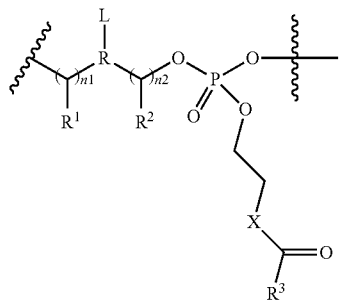

or a pharmaceutically acceptable salt thereof, wherein:
each instance of $R^1$ independently is —H or a $C_1$-$C_{20}$ aliphatic group;
each instance of $R^2$ independently is —H or a $C_1$-$C_{20}$ aliphatic group;
each instance of $R^3$ independently is —H or a $C_1$-$C_{20}$ aliphatic group;
X is independently S or O;
n1 is an integer from 1 to 6;
n2 is an integer from 1 to 6;
R is N or CH; and
L is $C_{1-6}$ alkyl or a protonatable group provided that when R is CH then L is a protonatable group, wherein the protonatable group comprises at least one 1° amino, 2° amino, 3° amino or imidazolyl group.

2. The polymer of claim 1, wherein $R^1$ independently is —H, —CH$_3$, or —CH$_2$CH$_3$.

3. The polymer of claim 1, wherein $R^2$ independently is —H, —CH$_3$, or —CH$_2$CH$_3$.

4. The polymer of claim 1, wherein $R^3$ independently is —H, —CH$_3$, —CH$_2$CH$_3$, —CH$_2$CH$_2$CH$_3$, CH(CH$_3$)$_2$, or C(CH$_3$)$_3$.

5. The polymer of claim 1, wherein X is independently O or S.

6. The polymer of claim 1, wherein the polymer is a homopolymer.

7. The polymer of claim 1, wherein the polymer is a copolymer.

8. The polymer of claim 7, wherein the polymer is an alternating copolymer.

9. The polymer of claim 7, wherein the polymer is a block copolymer.

10. The polymer of claim 1, wherein:
R is N; and L is $C_{1-6}$ alkyl;
R is CH; and L is a protonatable group; or
R is N; and L is a protonatable group.

11. The polymer of claim 1, wherein:
L is a protonatable group such that at least one conjugate acid of L-H has a pKa in water of about 4.5 to about 11.5.

12. The polymer of claim 1, comprising
a moiety T that is a targeting group.

13. A pharmaceutical composition comprising:
the polymer of claim 1; and
one or more polynucleotides.

14. The pharmaceutical composition of claim 13, wherein the one or more polynucleotides comprise RNA, wherein the RNA is selected from the group consisting of mRNA, siRNA, snoRNA, microRNA, gRNA, crRNA, and combinations thereof.

15. The pharmaceutical composition of claim 14, wherein the RNA is mRNA.

16. The pharmaceutical composition of claim 15, wherein the mRNA encodes a peptide, a polypeptide, or an enzyme.

17. The pharmaceutical composition of claim 15, wherein the mRNA encodes cystic fibrosis transmembrane conductance regulator (CFTR) protein for use in the delivery to or treatment of the lung of a subject or a lung cell.

18. The pharmaceutical composition of claim 15, wherein the mRNA encodes ornithine transcarbamylase (OTC) protein for use in the delivery to or treatment of the liver of a subject or a liver cell.

19. The pharmaceutical composition of claim 15, wherein the mRNA encodes a peptide or polypeptide for use in vaccine, and wherein the mRNA encodes an antigen.

20. A method of treating a disease in a subject, comprising administering to the subject an effective amount of the pharmaceutical composition of claim 13.

21. A polymer comprising a repeating unit that is

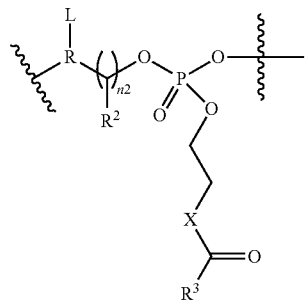

or a pharmaceutically acceptable salt thereof, wherein:
each instance of $R^1$ independently is —H or a $C_1$-$C_{20}$ aliphatic group;
each instance of $R^2$ independently is —H or a $C_1$-$C_{20}$ aliphatic group;
each instance of $R^3$ independently is —H or a $C_1$-$C_{20}$ aliphatic group;
X is independently S or O;
n2 is an integer from 1 to 6;
R is N or CH; and
L is $C_{1-6}$ alkyl or a protonatable group provided that when R is CH then L is a protonatable group, wherein the protonatable group comprises at least one 1° amino, 2° amino, 3° amino or imidazolyl group.

22. A homopolymer comprising a repeating group selected from the group consisting of:

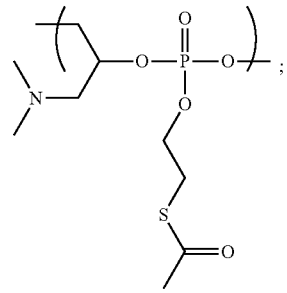

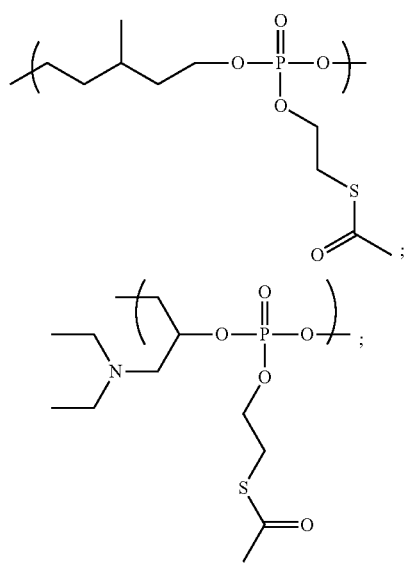
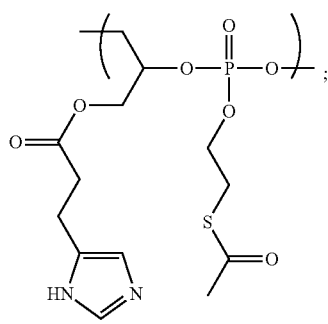
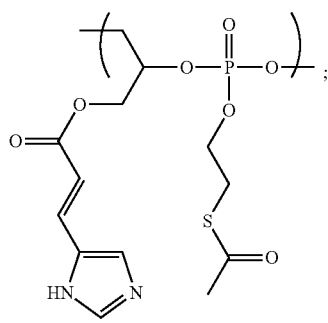
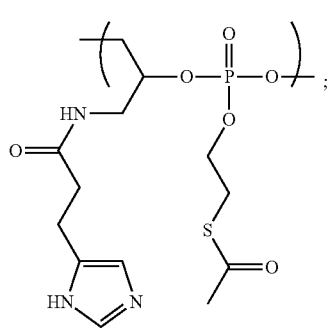
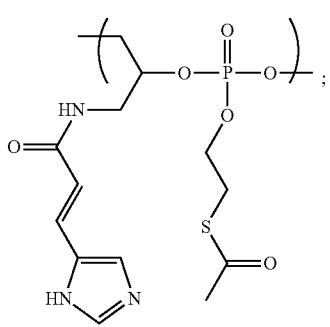
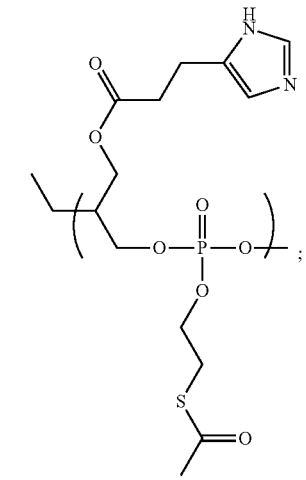
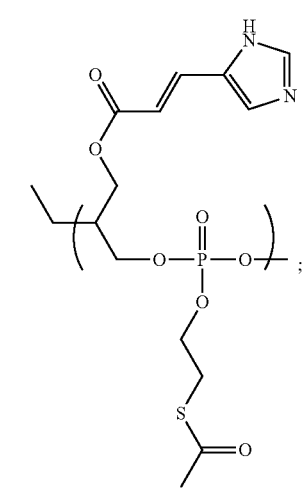

151
-continued
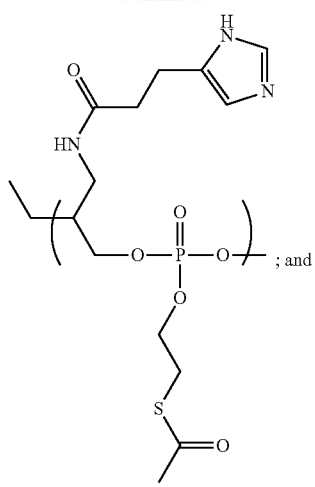
; and
152
-continued
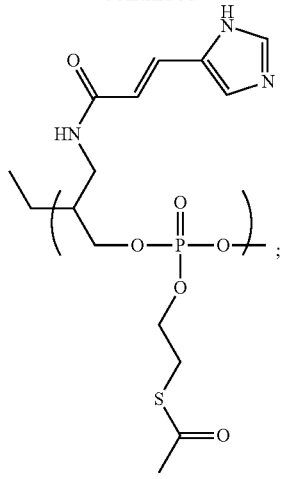
;
* * * * *